US008658207B2

(12) United States Patent
Eisenreich et al.

(10) Patent No.: US 8,658,207 B2
(45) Date of Patent: *Feb. 25, 2014

(54) EXTENDED RELEASE TABLET FORMULATIONS OF FLIBANSERIN AND METHOD FOR MANUFACTURING THE SAME

(75) Inventors: Wolfram Eisenreich, Ulm (DE);
Thomas Friedl, Ochsenhausen (DE);
Florian Sommer, Kisslegg (DE);
Nantharat Pearnchob, Biberach (DE);
Karl G. Wagner, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 860 days.

This patent is subject to a terminal disclaimer.

(21) Appl. No.: 11/837,959

(22) Filed: Aug. 13, 2007

(65) Prior Publication Data

US 2008/0038347 A1    Feb. 14, 2008

(30) Foreign Application Priority Data

Aug. 14, 2006 (EP) .................................. 06118896
Aug. 25, 2006 (EP) .................................. 06017754

(51) Int. Cl.
| | | |
|---|---|---|
| *A61K 9/22* | (2006.01) |
| *A61K 9/52* | (2006.01) |
| *A61K 9/26* | (2006.01) |
| *A61K 9/14* | (2006.01) |
| *A61P 25/24* | (2006.01) |
| *A61K 31/497* | (2006.01) |
| *A61K 31/50* | (2006.01) |
| *C07D 403/00* | (2006.01) |
| *C07D 235/00* | (2006.01) |
| *C07D 235/04* | (2006.01) |
| *C07D 235/24* | (2006.01) |

(52) U.S. Cl.
USPC .......... 424/468; 424/457; 424/470; 424/484; 424/485; 424/486; 424/487; 424/488; 514/17.6; 514/253.01; 514/295; 514/366; 514/370; 544/295; 544/366; 544/370; 548/304.4; 548/304.7; 548/306.4

(58) Field of Classification Search
None
See application file for complete search history.

(56) References Cited

U.S. PATENT DOCUMENTS

| | | |
|---|---|---|
| 3,096,248 A | 7/1963 | Rudzki |
| 3,406,178 A | 10/1968 | Crocker et al. |
| 3,472,854 A | 10/1969 | Archer |
| 4,200,641 A | 4/1980 | Vandenberk et al. |
| 4,367,217 A | 1/1983 | Gruber et al. |
| 4,737,500 A | 4/1988 | Sorg |
| 4,792,452 A | 12/1988 | Howard et al. |
| 4,797,399 A | 1/1989 | Ueda et al. |
| 4,859,692 A | 8/1989 | Bernstein et al. |
| 4,886,803 A | 12/1989 | Sueda et al. |
| 4,940,793 A | 7/1990 | Botrè et al. |
| 4,954,503 A | 9/1990 | Strupczewski et al. |
| 4,968,508 A | 11/1990 | Oren et al. |
| 5,002,948 A | 3/1991 | Perregaard et al. |
| 5,036,088 A | 7/1991 | Kitaura et al. |
| 5,225,417 A | 7/1993 | Dappen et al. |
| 5,405,642 A | 4/1995 | Gilis et al. |
| 5,407,686 A | 4/1995 | Patel et al. |
| 5,434,156 A | 7/1995 | Björk et al. |
| 5,492,907 A | 2/1996 | Pickar et al. |
| 5,552,412 A | 9/1996 | Cameron et al. |
| 5,576,318 A | 11/1996 | Bietti et al. |
| 5,591,743 A | 1/1997 | Patoiseau et al. |
| 5,854,290 A | 12/1998 | Arnsten et al. |
| 5,883,094 A | 3/1999 | Fliri et al. |
| 5,916,916 A | 6/1999 | Hauser et al. |
| 5,929,054 A | 7/1999 | Baker et al. |
| 5,977,106 A | 11/1999 | Patoiseau et al. |
| 6,068,846 A | 5/2000 | Cho et al. |
| 6,083,947 A | 7/2000 | Granger et al. |
| 6,165,513 A | 12/2000 | Dansereau et al. |
| 6,187,340 B1 | 2/2001 | Fukuta et al. |
| 6,281,218 B1 | 8/2001 | Cereda et al. |
| 6,284,757 B1 | 9/2001 | Sanner |
| 6,346,548 B1 | 2/2002 | Miller et al. |
| 6,426,087 B1 | 7/2002 | Saslawski et al. |
| 6,482,841 B1 | 11/2002 | Letelier et al. |

(Continued)

FOREIGN PATENT DOCUMENTS

| | | |
|---|---|---|
| BE | 904945 | 12/1986 |
| CA | 2455628 A1 | 2/2003 |
| CL | 1033-1999 | 5/1999 |
| CL | 2394-1999 | 10/1999 |
| CL | 1491-2001 | 6/2001 |

(Continued)

OTHER PUBLICATIONS

U.S. Appl. No. 08/039,002, filed Mar. 25, 1993, Bietti.
U.S. Appl. No. 11/956,949, filed Dec. 14, 2007, Lewis-D'Agostino, et al.
U.S. Appl. No. 12/390,665, filed Feb. 23, 2009, Wunderlich, et al.
U.S. Appl. No. 12/532,269, filed Dec. 14, 2009, Boeck, et al.

(Continued)

*Primary Examiner* — Robert A Wax
*Assistant Examiner* — Jeffrey T Palenik
(74) *Attorney, Agent, or Firm* — Michael P. Morris; Timothy X. Witkowski

(57) ABSTRACT

The present invention provides pharmaceutical release systems comprising an therapeutically effective amount of flibanserin and at least one pharmaceutically acceptable excipient, characterized in that said pharmaceutical release systems exhibit a pharmacokinetic profile that is characterized by an average maximum flibanserin plasma concentration $C_{max}$ lower than 300 ng/mL, preferably lower than 200 ng/mL after administration of a single dose to healthy volunteers in fasted state or directly after a meal.

6 Claims, 19 Drawing Sheets

(56) References Cited

U.S. PATENT DOCUMENTS

| | | |
|---|---|---|
| 6,521,623 B1 | 2/2003 | Cereda et al. |
| 6,586,435 B2 | 7/2003 | Cereda et al. |
| 6,627,646 B2 | 9/2003 | Bakale et al. |
| 6,680,071 B1 | 1/2004 | Johnson et al. |
| 7,151,103 B2 | 12/2006 | Borsini et al. |
| 7,183,410 B2 | 2/2007 | Bombarda et al. |
| 7,420,057 B2 | 9/2008 | Bombarda et al. |
| 2002/0001397 A1 | 1/2002 | Ishikawa et al. |
| 2002/0010216 A1 | 1/2002 | Rogosky et al. |
| 2002/0103208 A1 | 8/2002 | Cereda et al. |
| 2002/0151543 A1 | 10/2002 | Barberich et al. |
| 2003/0027823 A1 | 2/2003 | Cereda et al. |
| 2003/0060475 A1 | 3/2003 | Borsini |
| 2003/0083228 A1 | 5/2003 | Carpino et al. |
| 2003/0104980 A1* | 6/2003 | Borsini et al. .................... 514/2 |
| 2003/0119850 A1* | 6/2003 | Bombarda et al. ....... 514/254.06 |
| 2004/0023948 A1 | 2/2004 | Green et al. |
| 2004/0048877 A1 | 3/2004 | Friedl et al. |
| 2004/0116532 A1 | 6/2004 | Heacock et al. |
| 2004/0132697 A1 | 7/2004 | Thurlow et al. |
| 2004/0147581 A1 | 7/2004 | Taylor et al. |
| 2004/0180904 A1 | 9/2004 | Beck |
| 2004/0193452 A1 | 9/2004 | Berman |
| 2004/0235861 A1 | 11/2004 | Borsini |
| 2004/0258749 A1 | 12/2004 | Guldner et al. |
| 2005/0004105 A1 | 1/2005 | Leahy et al. |
| 2005/0037983 A1 | 2/2005 | Dinan et al. |
| 2005/0065158 A1 | 3/2005 | Naylor et al. |
| 2005/0095293 A1 | 5/2005 | Brauns et al. |
| 2005/0159430 A1 | 7/2005 | Bombarda et al. |
| 2005/0239798 A1 | 10/2005 | Pyke |
| 2005/0245539 A1 | 11/2005 | Mendla et al. |
| 2006/0014757 A1 | 1/2006 | Pyke |
| 2006/0025420 A1 | 2/2006 | Brauns et al. |
| 2006/0052391 A1 | 3/2006 | Dolsten |
| 2006/0160822 A1 | 7/2006 | Borsini |
| 2006/0199805 A1 | 9/2006 | Pyke et al. |
| 2006/0204486 A1 | 9/2006 | Pyke et al. |
| 2006/0211685 A1 | 9/2006 | Pyke et al |
| 2006/0252773 A1 | 11/2006 | Ceci |
| 2006/0258640 A1 | 11/2006 | Ceci et al. |
| 2006/0264511 A1 | 11/2006 | Pyke |
| 2006/0264512 A1 | 11/2006 | Pyke |
| 2007/0032654 A1 | 2/2007 | Bombarda et al. |
| 2007/0032655 A1 | 2/2007 | Bombarda et al. |
| 2007/0072872 A1 | 3/2007 | Borsini |
| 2007/0105869 A1 | 5/2007 | Pollentier et al. |
| 2007/0123540 A1 | 5/2007 | Ceci |
| 2007/0196473 A1 | 8/2007 | Friedl et al. |
| 2007/0265276 A1 | 11/2007 | Pollentier et al. |
| 2008/0038346 A1 | 2/2008 | Eisenreich et al. |
| 2008/0038347 A1 | 2/2008 | Eisenreich et al. |
| 2008/0069873 A1 | 3/2008 | Pearnchob et al. |
| 2008/0103155 A1 | 5/2008 | Mendla et al. |
| 2008/0119482 A1 | 5/2008 | Dolsten |
| 2008/0242678 A1 | 10/2008 | Ceci et al. |
| 2008/0242679 A1 | 10/2008 | Ceci |
| 2009/0023712 A1 | 1/2009 | Ferger et al. |
| 2009/0054458 A1 | 2/2009 | Bombarda et al. |
| 2009/0176698 A1 | 7/2009 | Baiker et al. |
| 2009/0239881 A1 | 9/2009 | Becker |
| 2009/0247546 A1 | 10/2009 | Ceci et al. |
| 2009/0312242 A1 | 12/2009 | Castro et al. |
| 2009/0318469 A1 | 12/2009 | Pyke et al. |

FOREIGN PATENT DOCUMENTS

| | | |
|---|---|---|
| CL | 2833-2001 | 11/2001 |
| CL | 418-2002 | 3/2002 |
| CL | 1706-2002 | 7/2002 |
| CL | 1878-2002 | 8/2002 |
| CL | 2389-2002 | 10/2002 |
| CL | 1751-2004 | 7/2004 |
| CL | 911-2005 | 4/2005 |
| CN | 1571670 A | 1/2005 |
| CN | 1655789 A | 8/2005 |
| DE | 3620643 A1 | 1/1987 |
| DE | 10209982.0 | 3/2002 |
| DE | 10138273 A1 | 2/2003 |
| EP | 0200322 A1 | 11/1986 |
| EP | 0376607 A1 | 7/1990 |
| EP | 0497985 A1 | 8/1992 |
| EP | 0526434 B1 | 2/1993 |
| EP | 0705832 A1 | 4/1996 |
| EP | 0816356 A1 | 1/1998 |
| EP | 0982030 A2 | 3/2000 |
| EP | 1256343 A1 | 11/2002 |
| EP | 1285658 | 2/2003 |
| EP | 1285658 A2 | 2/2003 |
| EP | 1014985 | 5/2003 |
| EP | 1518858 A1 | 3/2005 |
| EP | 1674102 | 6/2006 |
| GB | 2023594 A | 1/1980 |
| IE | 1992/1340 | 10/1992 |
| IL | 159151 B | 9/2009 |
| IL | 160389 B | 5/2010 |
| JP | 8-143476 | 6/1996 |
| RU | 93014306 A | 3/1995 |
| WO | WO 92/02215 | 2/1992 |
| WO | 92/03167 A1 | 3/1992 |
| WO | 92/19606 A1 | 11/1992 |
| WO | 93/03016 A1 | 2/1993 |
| WO | 95/01965 A1 | 1/1995 |
| WO | WO 95/19978 A1 | 7/1995 |
| WO | 95/34555 A1 | 12/1995 |
| WO | 96/05834 A1 | 2/1996 |
| WO | 96/16949 A1 | 6/1996 |
| WO | WO 9819668 A1 | 5/1998 |
| WO | 98/33784 A1 | 8/1998 |
| WO | 98/42344 A1 | 10/1998 |
| WO | 99/19302 A1 | 4/1999 |
| WO | WO 99/59584 A1 | 11/1999 |
| WO | WO 99/59593 | 11/1999 |
| WO | 00/28993 | 5/2000 |
| WO | WO 00/24383 A1 | 5/2000 |
| WO | WO 00/63193 A1 | 10/2000 |
| WO | 00/64441 A2 | 11/2000 |
| WO | WO 00/67735 A2 | 11/2000 |
| WO | WO 01/00224 A1 | 1/2001 |
| WO | 01/12170 A2 | 2/2001 |
| WO | 01/21593 A1 | 3/2001 |
| WO | WO 02/00654 A1 | 1/2002 |
| WO | 02/24662 A1 | 3/2002 |
| WO | WO 02/41894 A2 | 5/2002 |
| WO | WO 02/072586 A1 | 9/2002 |
| WO | 02/079143 A1 | 10/2002 |
| WO | WO 03/007949 A1 | 1/2003 |
| WO | 03/011396 A1 | 2/2003 |
| WO | 03/013539 A1 | 2/2003 |
| WO | 03/014079 A1 | 2/2003 |
| WO | 03/035072 A1 | 5/2003 |
| WO | WO 03074032 A1 | 9/2003 |
| WO | 03/097058 A1 | 11/2003 |
| WO | 2004/041259 A1 | 5/2004 |
| WO | 2004/045509 A2 | 6/2004 |
| WO | 2004/069339 A1 | 8/2004 |
| WO | 2005/007166 A1 | 1/2005 |
| WO | WO 2005/007166 A1 | 1/2005 |
| WO | 2005/044238 A1 | 5/2005 |
| WO | 2005/087207 A1 | 9/2005 |
| WO | 2005/102342 A1 | 11/2005 |
| WO | 2005/102343 A1 | 11/2005 |
| WO | 2006/010574 A1 | 2/2006 |
| WO | 2006/019715 A1 | 2/2006 |
| WO | WO 2006024471 A1 | 3/2006 |
| WO | 2006/096435 A1 | 9/2006 |
| WO | WO 2006/096434 A2 | 9/2006 |
| WO | 2006/125041 A1 | 11/2006 |
| WO | 2007/014929 A1 | 2/2007 |
| WO | WO 2007/023325 A2 | 3/2007 |
| WO | 2007/048803 A1 | 5/2007 |
| WO | WO 2007090091 A2 | 8/2007 |
| WO | WO 2008/006839 A2 | 1/2008 |

(56) References Cited

FOREIGN PATENT DOCUMENTS

| WO | WO 2008006838 A1 | 1/2008 |
|---|---|---|
| WO | WO 2008/022932 A2 | 2/2008 |
| WO | WO 2008019996 A2 | 2/2008 |
| WO | WO 2008116890 A2 | 10/2008 |

OTHER PUBLICATIONS

U.S. Appl. No. 12/675,231, filed Feb. 25, 2010, Hanes, et al.
U.S. Appl. No. 12/280,804, filed Aug. 27, 2008, Ceci.
U.S. Appl. No. 12/306,946, filed Dec. 29, 2008, Becker.
U.S. Appl. No. 12/306,945, filed Dec. 29, 2008, Pyke.
U.S. Appl. No. 12/306,878, filed Dec. 29, 2008, Castrol et al.
Anonymous, Hormone Patch may Provide Some Increase in Sexual Desire in Menopausal Women, Jul. 25, 2005, URL:http://pubs.ama-assn.org/media/2005a/0725.dtl, 2 pgs.
Bechard, et al., Int. J. Pharm., 1992, 87:133-139.
Braiman, Psychosexual disorders of young adulthood, Clin Obstetrics and Gynecology, 1970, 13(3):734-745.
Byrn, et al., Hydrates and Solvates, Solid State Chemistry & Drugs, 1999, Chpt. 11, pp. 233-247.
Buhrich, et al., Can fetishism occur in transexuals?, Arch Sex Behav, 1977, 6(3):223-235.
Butts, The relationship between sexual addiction and sexual dysfunction, J. Health Care Underserved, 1992, 3(1):128-35; discussion 136-7.
Buvat, et al., Role of hormones in sexual dysfunction, homosexuality, transsexualism, and paraphilia related disorders. Diagnostic and therapeutic consequences, Contracept Fertil Sex, 1996, 24(11):834-846-only English abstract.
Bymaster, et al., Fluoxetine, but not other selective serotonin uptake inhibitors, increases norepinephrine and dopamine extracellular levels in prefrontal cortex, Psychopharmacology, 2002, 160:353-361.
Chiao, et al., Remington Pharm 19$^{th}$ Ed., Panamerican Spain, 1988, pp. 2535-2537.
Cooper, et al., A female sex offender with multiple paraphilias: a psychologic, physiol ogic (laboratory sexual arousal) and endocrine case study, Can J Psychiatry, 1990, 35(4):334-7.
Grau, et al., Risk Factors, Outcome, and Treatment in Subtypes of Ischemic Stroke: The German Stroke Data Bank, Stroke, 2001; 32:2559-2566.
Guarraci, et al: Coffee, Tea and Me: Moderate doses of caffeine affect sexual behavior in female rats, Pharma Biochem and Behavior, Nov. 2005, 82(3):522-530. ISSN: 0091-3057 Elsevier, US, abstract.
Kafka, A Monoamine Hypothesis for the Pathophysiology of Paraphilic Disorders, Archives of Sex Behav, 1997, 26(4):343-58.
Marshall, et al., Unified Approach to the Analysis of Genetic Variation in Serotonergic Pathways, Am J. Med. Genetics Neurophychiatric Genetics, 1999, 88:621-627.
Moser, Lust, lack of desire and paraphilias: some thoughts and possible connections, Marital Ther, 1992, 18(1):65-9.
Mutschler, et al., The Effect of Drugs: Antidepressive Agents, Manual of Pharmacology and Toxicology, 8th Ed, 2001, pp. 171-172, Scientific Publishing Company PLC, Stuttgart.
Otsuka, et al., Chem. Pharm. Bull., 1999, 47(6):852.856.
Pharmacopia, 1995, p. 1843.
Schwartz, et al., Conceptual factors in the treatment of paraphilias: a preliminary rep., Maritial Ther, 1983, 9(2):3-18.
Semkova, et al., Neuroprotective effect of 5-HT1A receptor agonist, Bay x 3702, demonstrated in vitro and in vivo, Euro J Pharm, 1998, 359:251-260.
Singhal, et al., Advanced Drug Delivery Reviews, 2004, 56:335-347.
Soederberg, et al., Leptin Is a Risk Marker for First-Ever Hemorrhagic Stroke in a Population-Based Cohort, Stroke, Jl of the Am Heart Assoc., 1999; 30:328-337.
Stedman's Medical Dictionary definition "Anxiety", 28$^{th}$ Ed., 2006, p. 114, Lippincott Williams & Wilkins, Baltimore MD.
Thrombolytic Therapy: MedlinePlus Medical Encyclopedia, http://www.nlm.nih.gov/medlineplus/ency/article/007089.htm, accessed Dec. 17, 2009, pp. 1-4.
Vippagunta, Acv. Drug Del. Rev., 2001, 48:3-26.
Welsh, et al., Effect of Lactacidosis on Pyridine Nucleotide Stability During Ischemia in Mouse Brain, J Neurochemistry, 1987, 49(3):846-851.
Zverina, et al., The occurrence of atypical sexual experience among various female groups, Arch Sex Behav, 1987, 16(4):321-6.
Alexander et al., J. of Am. Acad. Of Nurse Practitioners, 2007, 19:152-163.
Guilleminault et al., Atypical Sexual Behavior During Sleep, Phychosomatic Med., 2002, 64:328-336.
Basson et al., Sexual psychophysiology and effects of sildenafil citrate in oestrogenised women with acquired genital arousal disorder and impaired orgasm: a randomised controlled trial, BJOG: an International Journal of Obstetrics and Gyn., Nov. 2003, 110:1014-1024.
Basson et al., Efficacy and Safety of Sildenafil Citrate in Women with Sexual Dysfunction Associated with Female Sexual Arousal Disorder, J Women's Health & Gender-Based Medicine, Nov. 4, 2002 11:367-77.
Black et al., Inappropriate sexual behaviors in dementia, J of Geriatric Psychiatry & Neurology, Sep. 2005, 18(3):155-162.
Clayton, Epidemiology and Neurobiology of Femal Sexual Dysfunction, J Sex Med., Nov. 4, 2007, Suppl 4:260-8.
Clayton et al., Burden of phase-specific sexual dysfunction with SSRIs, J Affect Disord., Mar. 2006, 91(1):27-32.
Clayton et al., Prevalence of Sexual Dysfunction Among Newer Antidepressants, J. Clin. Psychiatry, 2002, 63(4):357-366.
CMU Pharmaceutical polymorphism, http://www.andrew.cmu.edu/user/suter/polymorph.html, internet p. 1-3 (2002): obtained Feb. 11, 2009.
Sexual Dysfunction and Hypotestosteronemia in Patients With Obstructive Sleep Apnea Syndrome and Its Effects With CPAP Therapy, http:..clinicaltrials.gov/ct2/show/NCT00832065, obtained Apr. 1, 2009, 4pgs.
Doelker et al., Crystalline modifications and polytnorphism changes during drug manufacturing, Annales Pharmaceutiques Francaises, 2002, 60(3):161-169.
Doelker et al., Physicochemical behavior or active substances. Consequences for the feasibility and stability of pharmaceutical forms, S.T.P. Pharma Pratiques, 1999, 9(5):399-409.
Engleson, Concise Encyclopedia Chemistry, 1993, pp. 872-873.
Giraldi et al., Physiology of Female Sexual Function: Animal Models, J Sex Med, 2004, 1(3):237-253.
Girgis et al., A double-blind trial of clomipramine in premature ejaculation, Andrologia, Jul.-Aug. 1982, 14(4):364-8.
Goldfischer et al., Selected 2008 Abstracts from the International Society for the Study of Women's Sexual Health, J. Sex. Med., 2008, 5(suppl. 3):159-160.
Goodman, An assessment of clomipramine (Anafranil) in the treatment of premature ejaculation, J Int Med Res., 1980; 8(Suppl 3):53-9.
Haensel et al., Fluoxetine and premature ejaculation: A double-blind, crossover, placebo-controlled study, J Clin Psychopharmacology, 1998, 18:72-77.
Haensel et al., Clomipramine and sexual function in men with premature ejaculation and controls, J Urology, Oct. 1996, 156(B193):1310-1315.
Jain et al., Polymorphism in Pharmacy, Indian Drugs, 1986, 23(6):315-329.
Kandeel et al., Male Sexual Function and its Disorders: Physiology, Pathophysiology, Clinical investigation, and Treatment, Endocrine Reviews, 2001, 22(3):342-388 at 370.
Kennedy et al., Antidepressant-Induced Sexual Dysfunction During Treatment with Moclobemide, Paroxetine, Sertraline, and Venlafaxine, J Clin Psychiatry, 2000; 61:276-81.
Kennedy et al., Sexual dysfunction before antidepressant therapy in major depression, J. Affective Disorders, 1999, 56:201-208.
Konarski et al., Effects of Acute Flibanserin on FDG-PET Brain Glucose Metabolism in Men with Major Depressive Disorder, Aug. 2008 Barcelona meeting of the European College of Nueropsychopharmacology, 3 pgs. (poster-abstract).
McKenna, Neural Circuitry Involved in Sexual Function, J Spinal Cord Med., 2001, 24:148-154.

(56) References Cited

OTHER PUBLICATIONS

McMahon et al., Efficacy of type-5 phosphodiesterase inhibitors in the drug treatment of premature ejaculation: a systematic review, BJU Int., 2006, 98:259-72.
Montejo-Gonzales et al., SSRI-induced sexual dysfunction: fluoxetine, paroxetine, sertraline, and fluvoxamine in a prospective, multicenter, and descriptive clinical study of 344 patients, J Sex Marital, 1997 Fall; 23(3):176-94.
Muzaffar et al., J. Pharmacy, 1979, 1(1):59-66.
Nurnberg et al., Sildenafil for Sexual Dysfunction in Women Taking Antidepressants, Am J Psychiatry, Oct.—Letters to the Editor, 1999, 156(10):1664.
Nurnberg et al., Sildenafil Treatment of Women with Antidepressant-Associated Sexual Dysfunction, JAMA, Jul. 2008, 300(4):395-404.
Pfaus et al., What can animal models tell us about human sexual response?, Annu Rev Sex Res, 2003, 14:1-63.
Porter, Remingtons, 1990, Chpt 90, pp. 1666-1675.
Pryor et al., Efficacy and tolerability of dapoxetine in treatment of premature ejaculation: an integrated analysis of two double-blind, randomized controlled trials, Lancet, 2006, 368(9539):929-37.
Pyke et al., Flibanserin: A Novel Centrally Acting Agent that is not an Effective Antidepressant but has Potential to Treat Decreased Sexual Desire in Women, APA, May 2008, 1 pg. (accepted poster).
Pyke et al., Flibanserin: A Novel Centrally Acting Agent that is not an Effective Antidepressant but has Potential to Treat Decreased Sexual Desire in Women, APA, May 2008, 1 pg. (accepted abstract).
Rapkin, General Gynecology, 2007, 196:97-106.
Rendell et al., Sildenafil for Treatment of Erectile Dysfunction in Men with Diabetes, JAMA, 1999, 281:421-426.
Rosen et al., Effects of SSRIs on sexual function: a critical review, J Clin Psychopharmacol., Feb. 1999 19(1):67-85.
Rosen et al., PDE-5 inhibition and sexual response: Pharmacological mechanisms and clinical outcomes, Annual Review of Sex Res, 2002, pp. 36-88.
Rosen, Sexual pharmacology in the 21st century, J Gend Specif Med., Jul.-Aug. 2000, 3(5):45-52.
Rowland, Neurobiology of Sexual Response in Men and Women, I:CNS Spectr., Aug. 2006, 11(8 Suppl 9):6-12.
Rubenstein, Pharmaceutics: The Science of Dosage Form Design, ed. Aulton, 1988, pp. 304-321.
Martin, Sexsomnia, http://lakesidepress.com/pulmonary/Sleep/sexsomnia.html, obtianed Apr. 1, 2009, 5pgs.
Stearns et al., J. of Clin. Oncology, 2002, 20(6):1436-1438.
Stedman's Medical Dictionary definition "Prevention," 2000, 28th Ed., 3 pgs., Lippincott Williams & Wilkins.
Stoleru et al., Brain processing of visual sexual stimuli in men with hypoactive sexual desire disorder, Psychiatry Res.: Neuroimaging, 2003, 124(2):67-86.
Clayton et al., Validation of the Decreased Sexual Desire Screener (DSDS): A Brief Diagnostic Instrument for Generalized, Acquired Hypoactive Sexual Desire Disorder in Women, International Society for the Study of Womens Sexual Health (ISSWSH) annual meeting, 2007, 2 pgs. (poster and abstract).
Wunderlich et al., Using e-Diaries to Measure Sexual Desire in Women with Hypoactive Sexual Desire Disorder, International Society for the Study of Womens Sexual Health (ISSWH) annual meeting, 2007, 11 pgs. (Oral Presentation).
Clayton et al., Validation of the Sexual Interest and Desire Inventory-Female (SIDI-F) in North American Women, International Society for the Study of Womens Sexual Health (ISSWH) annual meeting, 2007, 3 pgs. (poster and abstract).
Clayton et al., Validity of Sexual Distress Scales vs Electronic Diary in Women with Decreased Sexual Desire , American College of Obstetrics and Gynecologists (ACOG) annual meeting, 2007, 1 pg. (abstract only).
Clayton et al., Validating the Sexual Interest and Desire Inventory (SIDI-F) in North American Women , American College of Obstetrics and Gynecologists (ACOG) annual meeting, 2007, 1 pg. (abstract only).
Clayton et al., Validation of the Sexual Interest and Desire Inventory-Female (SIDI-F) in North American Women, American Psychiatric Association (APA) annual meeting, 2007, 2 pgs. (poster and abstract).
Tignol et al., Using e-Diaries to Measure Sexual Desire in Women with Hypoactive Sexual Desire Disorder, European Society for Sexual Medicine (ESSM) annual meeting, 2007, 9 pgs. (oral presentation).
Clayton, Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 10 pgs. (oral presentation).
Clayton et al., Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 1 pgs. (abstract).
Clayton et al., Baseline characteristics of patients enrolled in three Phase III North American trials of flibanserin in premenopausal women with Hypoactive Sexual Desire Disorder, International Society for the Study of Womens Sexual Health (ISSWSH) annual meeting 2009, poster, 2 pgs. (poster and abstract).
Clayton et al., Validation of the Decreased Sexual Desire Screener (DSDS): A Brief Diagnostic Instrument for Generalized Acquired Female Hypoactive Sexual Desire Disorder (HSDD); J. Sex Med., 2009, pp. 1-9. (epub ahead of print).
Dean, Decreased Sexual Desire Screener © (DSDS © ) for Diagnosis of Hypoactive Sexual Desire Disorder in Women, WONCA Europe conference, 2008, 8 pgs. (oral presentation).
Dean et al., Decreased Sexual Desire Screener © (DSDS © ) for Diagnosis of Hypoactive Sexual Desire Disorder in Women, WONCA Europe conference, 2008, 1 pg. (abstract).
Derogatis et al., Validation of Sexual Distress Scales and Electronic Diary in Women with Hypoactive Sexual Desire Disorder, International Society for the Study of Womens Sexual Health (ISSWSH) annual meeting, 2007, 3 pgs. (poster and abstract).
Derogatis et al., Validation of Sexual Distress Scales and Electronic Diary in Women with Hypoactive Sexual Desire Disorder. American Psychiatric Association (APA) annual meeting, 2007, 2 pgs. (poster and abstract).
Derogatis et al., Content Validity of the Female Sexual Distress Scale-Revised (FSDS-R) in Women with Hypoactive Sexual Desire Disorder (HSDD), Joint Congress of the European and International Societies of Sexual Medicine (ESSM/ISSM) 2008, 5 pgs. (poster, oral presentation and abstract).
Derogatis et al., Validation of the Female Sexual Distress Scale Revised (FSDS-R) for assessing distress in women with Hypoactive Sexual Desire Disorder (HSDD), J Sex Med., 2008, 5:357-364.
Dennerstein et al., Differentiating Four Cognitive-Behavioral Types of Women with Low Sexual Desire, International Society for the Study of Womens Sexual Health (ISSWSH) annual meeting, 2007, 9 pgs. (Oral Presentation).
Dennerstein et al., Differentiating Four Cognitive-Behavioral Types of Women with Decreased Sexual Desire, International Society for the Study of Womens Sexual Health (ISSWSH) annual meeting, 2007, 2 pgs. (abstract).
Dennerstein et al., Differentiating Four Cognitive-Behavioral Types of Women with Decreased Sexual Desire, American Psychiatric Association (APA) annual meeting, 2007, 3 pgs. (poster and abstract).
Dennerstein et al., Differentiating Four Cognitive-Behavioral Types of Women with Decreased Sexual Desire, European Society for Sexual Medicine (ESSM) annual meeting, 2007, 3 pgs. (poster and abstract).
Dennerstein, Differentiating Four Cognitive-Behavioral Types of Women with Low Sexual Desire, European Society for Sexual Medicine (ESSM) annual meeting, 2007, 10 pgs. (oral presentation).
Dennerstein et al., Attitudes Towards Partner Interactions of Women With Characteristics of HSDD: Preliminary Results of a Multinational Study of 1,402 Women. International Society for the Study of Womens Sexual Health (ISSWSH) annual meeting, 2008, 12 pgs. (oral presentation and abstract).

(56) References Cited

OTHER PUBLICATIONS

Goldfischer et al., Validation of the Decreased Sexual Desire Screener (DSDS): a Brief Diagnostic Instrument for Generalized, Acquired Hypoactive Sexual Desire Disorder in Women, American Psychiatric Association (APA) annual meeting, 2007, 2 pgs. (poster and abstract).
Pyke et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (poster).
Goldfischer et al., Efficacy of Continued Flibanserin Treatment on Sexual Desire and Satisfying Sexual Events in Premenopausal Women With HSDD: Results From the ROSE Study, International Society for the Study of Womens Sexual Health (ISSWSH) annual meeting, 2008, 1 pgs. (abstract).
Goldfischer et al., Efficacy of Continued Flibanserin Treatment on Distress Associated with Sexual Dysfunction in Premenopausal Women With HSDD: Results From the ROSE Study, International Society for the Study of Womens Sexual Health (ISSWSH) annual meeting, 2008, 2 pgs. (poster and abstract).
Goldfischer et al., Efficacy of Continued Flibanserin Treatment on Sexual Functioning in Premenopausal Women With HSDD: Results From the ROSE Study, International Society for the Study of Womens Sexual Health (ISSWSH) annual meeting, 2008, oral presentation, 1 pg. (abstract only).
Goldfischer et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 1 pg. (abstract only).
Goldfischer et al., The ROSE Study: Placebo-controlled Randomized Withdrawal Trial of Flibanserin for Hypoactive Sexual Desire Disorder in Premenopausal Women. European Federation of Sexology (EFS), 2008, 7 pgs. (oral presentation and abstract).
Goldfischer et al., Decreased Sexual Desire Screener (DSDS) for Diagnosis of Hypoactive Sexual Desire Disorder in Women, American College of Obstetrics and Gynecologists (ACOG) annual meeting, 2008, 2 pgs. (poster and abstract).
Goldfischer et al., Efficacy of Continued Flibanserin Treatment in Premenopausal Women with Hypoactive Sexual Desire Disorder: Results from the ROSE Study, International Academy of Sex Research (IASR) annual meeting, 2008, 3 pgs. (poster and abstract).
Goldfischer et al., Safety and Tolerability of Flibanserin in Premenopausal Women with Hypoactive Sexual Desire Disorder: Results from the ROSE Study, International Academy of Sex Research (IASR) annual meeting, 2008, 3 pgs. (poster and abstract).
Goldfischer et al., Efficacy and Safety of Flibanserin in Premenopausal Women with Hypoactive Sexual Desire Disorder: Results from the Randomized Withdrawal ROSE Study, Institute on Psychiatric Services (IPS) annual meeting, 2008, 2 pgs. (poster and abstract).
Goldfischer et al., Decreased Sexual Desire Screener (DSDS) for Diagnosis of Hypoactive Sexual Desire Disorder in Women, Sexual Medicine Society of North America (SMSNA) annual meeting, 2008, 3 pgs. (poster and abstract).
Goldfischer et al., Efficacy and Safety of Flibanserin in Premenopausal Women with Hypoactive Sexual Desire Disorder: Results From the Randomized Withdrawal ROSE Study, Sexual Medicine Society of North America (SMSNA) annual meeting, 2008, 3 pgs. (poster and abstract).
Goldfischer, Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 10 pgs. (oral presentation).
Goldfischer et al., Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (abstract).
Goldfischer et al., Safety and Tolerability of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (poster and abstract).
Goldstein et al., Differences in Patient-Physician Communication Regarding Hypoactive Sexual Desire Disorder (HSDD), Sexual Medicine Society of North America (SMSNA) annual meeting, 2007, 3 pgs. (poster and abstract).
Goldstein et al., Emotions Related to Distress in Patients with Hypoactive Sexual Desire Disorder: Results of Patient and Physician Interviews, Sexual Medicine Society of North America (SMSNA) annual meeting, 2007, 3 pgs. (poster and abstract).
Jolly et al., Design of Phase III Pivotal Trials of Flibanserin in Female Hypoactive Sexual Desire Disorder (HSDD), European Federation of Sexology (EFS), 2008, 2 pgs. (poster and abstract).
Nappi et al., Validation of the Sexual Interest and Desire Inventory-Female (SIDI-F) in European Women, European Federation of Sexology (EFS), 2008, 2 pgs. (poster and abstract).
Nappi, Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 8 pgs. (oral presentation).
Nappi et al., Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 1 pg. (abstract).
Nappi et al., Decreased Sexual Desire Screener (DSDS) For Diagnosis of Hypoactive Sexual Desire Disorder (HSDD) in European Women, International Society for the Study of Womens Sexual Health (ISSWSH) annual meeting, 2009, oral presentation, 8 pgs. (oral presentation).
Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 1 pg. (abstract).
Pyke et al., Using e-Diaries to Measure Sexual Desire in Women with Hypoactive Sexual Desire Disorder, American Psychiatric Association (APA) annual meeting, 2007, 2 pgs. (poster and abstract).
Pyke et al., The ROSE Study: Placebo-Controlled Randomized Withdrawal Trial of Flibanserin for Hypoactive Sexual Desire Disorder in Premenopausal Women (Study Design Only), Institute on Psychiatric Services (IPS) annual meeting, 2007, 2 pgs. (poster and abstract).
Pyke et al., Safety and Tolerability of Flibanserin in Premenopausal Women With Hypoactive Sexual Desire Disorder (HSDD): Results From the ROSE Study, American Psychiatric Association (APA) annual meeting, 2008, 2 pgs. (poster and abstract).
Pyke et al., Flibanserin: a Novel Centrally Acting Agent That is not an Effective Antidepressant but has Potential to Treat Decreased Sexual Desire in Women, American Psychiatric Association (APA) annual meeting, 2008, 2 pgs. (poster and abstract).
Rosen et al., The Predictors of Sexual Distress in Women With Low Sexual Desire, International Society for the Study of Womens Sexual Health (ISSWSH) annual meeting, 2009, oral presentation, 15 pgs. (oral presentation and abstract).
Shifren et al., Sexual Problems and Distress in United States Women: Prevalence and Correlates, Obstet. Gynecology, Nov. 2008, 112(5):970-978.
Shifren et al., Treatment-seeking Behavior of U.S. Women with Hypoactive Sexual Desire Disorder (HSDD), American College of Obstetrics and Gynecologists (ACOG) annual meeting, 2008, 2 pgs. (poster and abstract).
Pyke et al., Validation of the Sexual Interest and Desire Inventory-Female (SIDI-F) in European Women, International Society for the Study of Womens Sexual Health (ISSWSH) annual meeting, 2007, 20 pgs. (oral presentation).
Nappi et al., Validation of the Sexual Interest and Desire Inventory-Female (SIDI-F) in European Women, European Society for Sexual Medicine (ESSM) annual meeting, 2007, 19 pgs. (oral presentation).

(56) References Cited

OTHER PUBLICATIONS

Sand et al., The Female Sexual Function Index (FSFI): A Potential "Gold Standard" Measure for Assessing Therapeutically-Induced Change in Female Sexual Function, ASRM, 2009, Oct. 17-21, 2009, Atlanta, Georgia, 2 pgs. (poster and abstract).
Smith et al., Pharmacokinetics of Flibanserin in Premenopausal Women With Hypoactive Sexual Desire Disorder Including Effects on the Female Sexual Function Index, ESSM, 2009, Nov. 2009, 2 pgs., Lyon. (poster and abstract).
Clayton et al., Efficacy of Flibanserin As a Potential Treatment for Hypoactive Sexual Desire Disorder in North American Premenopausal Women: Results From the Dahlia Trial, ESSM, 2009, Nov. 2009, 2 pgs., Lyon. (poster and abstract).
Thorp et al., Efficacy of Flibanserin As a Potential Treatment for Hypoactive Sexual Desire Disorder in North American Premenopausal Women: Results From the Daisy Trial, ESSM, 2009, Nov. 2009, 3 pgs., Lyon. (poster and abstract).
Jolly et al., Design of Randomized Controlled Trials of Flibanserin in Premenopausal Women With Hypoactive Sexual Desire Disorder, ESSM 2009, Nov. 2009, 3 pgs., Lyon. (poster and abstract).
Revicki et al., Content Validity of the Female Sexual Function Index in Pre- and Postmenopausal Women With Hypoactive Sexual Desire Disorder, ESSM 2009, Nov. 2009, 2 pgs., Lyon. (poster and abstract).
Aubert et al., Comparison of Flibanserin With the 5-Ht1a Agonist (+)-8-Oh-Dpat in Affecting Interactions Between Male-Female Marmoset Pairs, ESSM 2009, Nov. 2009, 2 pgs., Lyon (poster and abstract).
Rosen et al., Criterion Validity of the Sexual Desire Domain of the Female Sexual Function Index (Fsfi): Identifying a Diagnostic Cut-Point for Differentiating Women With and Without Hsdd, ESSM 2009, Nov. 2009, 3 pgs., Lyon. (poster and abstract).
Rosen et al., Validation of the FSFI Sexual Desire Domain Diagnostic Cut-Point in Predicting Hsdd in Women: Independent Replication and Confirmation, ESSM 2009, Nov. 2009, 2 pgs., Lyon. (poster and abstract).
Nappi, Efficacy of Flibanserin As a Potential Treatment for Hypoactive Sexual Desire Disorder in European Premenopausal Women: Results From the Orchid Trial; ESSM 2009, Nov. 2009, 12 pgs., Lyon. (oral presentation).
Nappi et al., Efficacy of Flibanserin As a Potential Treatment for Hypoactive Sexual Desire Disorder in European Premenopausal Women: Results From the Orchid Trial; ESSM 2009, Nov. 2009, 1 pg., Lyon. (abstract).
Holstege et al., Differences in Brain Activity in Premenopausal Women With Hypoactive Sexual Desire Disorder (Hsdd) Compared to Women Without Sexual Dysfunction, ESSM 2009, Nov. 2009, 2 pgs., Lyon. (abstract only).
Holstege et al., Brain activation and de-activation caused by erotic movies is lower in HSDD-than in non-HSDD volunteers, ESSM 2009, 8 pgs. (oral presentation).
Jolly, Efficacy of Flibanserin 100 Mg Qhs As a Potential Treatment for Hypoactive Sexual Desire Disorder in Premenopausal Women, ESSM 2009, Nov. 2009, 12 pgs., Lyon. (oral presentation).
Jolly et al., Efficacy of Flibanserin 100 Mg Qhs As a Potential Treatment for Hypoactive Sexual Desire Disorder in Premenopausal Women, ESSM 2009, Nov. 2009, 1 pgs., Lyon. (abstract).
Jolly et al., Efficacy of Flibanserin 100 Mg Qhs As a Potential Treatment for Hypoactive Sexual Desire Disorder in North American Premenopausal Women, ESSM 2009, Nov. 2009, 2 pgs., Lyon. (poster and abstract).
Clayton, Safety and Tolerability of Flibanserin in Premenopausal Women With Hypoactive Sexual Desire Disorder, ESSM 2009, Nov. 2009, 12 pgs., Lyon. (oral presentation).
Jolly et al., Safety and Tolerability of Flibanserin in Premenopausal Women With Hypoactive Sexual Desire Disorder, ESSM 2009, Nov. 2009, 1 pg., Lyon. (abstract).
Jolly et al., Efficacy of Flibanserin As a Potential Treatment for Hypoactive Sexual Desire Disorder in North American Premenopausal Women: Results From the Violet Trial, ESSM 2009, Nov. 2009, 3 pgs., Lyon. (poster and abstract).
Fuchs, Baseline Characteristics of Patients Enrolled in Three Phase III North American Trials of Flibanserin in Premenopausal Women With Hypoactive Sexual Desire Disorder, FIGO 2009, Oct. 2009, 10 pgs., Cape Town, South Africa. (oral presentation).
Goldfischer, Efficacy and Safety of Flibanserin in a Randomized Withdrawal Study of Premenopausal Women With Hypoactive Sexual Desire Disorder, FIGO2009, Oct. 2009, 12 pgs., Cape Town, South Africa. (oral presentation).
Goldfischer et al., Efficacy and Safety of Flibanserin in a Randomized Withdrawal Study of Premenopausal Women With Hypoactive Sexual Desire Disorder, FIGO2009, Oct. 2009, 1 pgs., Cape Town, South Africa. (abstract).
Revicki et al., Content Validity of the Female Sexual Function Index in Pre- and Postmenopausal Women With Hypoactive Sexual Desire Disorder, ICSM 2009, Jul. 2009, 2 pgs., Paris. (poster and abstract).
Revicki et al., Content Validity of the Female Sexual Function Index in Pre-Menopausal Women With Hypoactive Sexual Desire Disorder, ICSM 2009, Jul. 2009, 2 pgs., Paris. (poster and abstract).
Rosen et al., Criterion Validity of the Sexual Desire Domain of the Female Sexual Function Index (Fsfi): Identifying a Diagnostic Cut-Point for Differentiating Women With and Without Hsdd, ICSM 2009, Jul. 2009, 2 pgs., Paris. (poster and abstract).
Rosen et al., Validation of the Fsfi Sexual Desire Domain Diagnostic Cut-Point in Predicting Hsdd: Independent Replication and Confirmation, ICSM 2009, Jul. 2009, 2 pgs., Paris. (poster and abstract).
Sand et al., The Female Sexual Function Index (Fsfi): A Potential "Gold Standard" Measure for Assessing Sexual Function in Women, ICSM 2009, Jul. 2009, 2 pgs., Paris. (poster and abstract).
Jayne, Results From the Dahlia (511.70) Trial: A Prospective Study of Flibanserin for the Treatment of Hypoactive Sexual Desire Disorder in North American Premenopausal Women, SMSNA 2009, Nov. 2009, 3 pgs., San Diego, USA (oral presentation).
Jayne et al., Results From the Dahlia (511.70) Trial: A Prospective Study of Flibanserin for the Treatment of Hypoactive Sexual Desire Disorder in North American Premenopausal Women, SMSNA 2009, Nov. 2009, 2 pgs., San Diego, USA (abstract and poster).
Sand et al., Efficacy of Flibanserin in North American Premenopausal Women With Hypoactive Sexual Desire Disorder: Results From the Daisy Trial, SMSNA 2009, Nov. 2009, 2 pgs., San Diego, USA. (poster and abstract).
Sand, Efficacy of Flibanserin in North American Premenopausal Women With Hypoactive Sexual Desire Disorder: Results From the Daisy Trial, SMSNA 2009, Nov. 2009, 2 pgs., San Diego, USA. (oral presentation).
Sand et al., The Female Sexual Function Index (Fsfi) Is a Potential "Gold Standard" Measure for Assessing Sexual Function in Pre- and Post-Menopausal Women: A Systematic Review, SMSNA 2009, Nov. 2009, 2 pgs., San Diego, USA. (poster and abstract).
Sand et al., Efficacy of Flibanserin 100 Mg Qhs As a Potential Treatment for Hypoactive Sexual Desire Disorder in North American Premenopausal Women, SMSNA 2009, Nov. 2009, 2 pgs., San Diego, USA. (poster and abstract).
Sand, Efficacy of Flibanserin 100 Mg Qhs As a Potential Treatment for Hypoactive Sexual Desire Disorder in North American Premenopausal Women, SMSNA 2009, Nov. 2009, 2 pgs., San Diego, USA. (oral presentation).
Holstege et al., Differences in Brain Activity in Premenopausal Women With Hypoactive Sexual Desire Disorder (Hsdd) Compared to Women Without Sexual Dysfunction, SMSNA 2009, Nov. 2009, 2 pgs., San Diego, USA (abstract only).
Holstege et al., Brain activation and de-activation caused by erotic movies is lower in HSDD-than in non-HSDD volunteers, SMSNA, 2009, 4 pgs (poster & oral presentation).
Sand et al., Pooled Clinical Trail Analysis of Flibanserin Safety and Tolerability in Premenopausal Women with Hypoactive Sexual Desire Disorder, SMSNA, 2009, 2 pgs. (poster and abstract).
Sand, Pooled Clinical Trail Analysis of Flibanserin Safety and Tolerability in Premenopausal Women with Hypoactive Sexual Desire Disorder, SMSNA, 2009, 2 pgs. (oral presentation).
Sand et al., Effacacy of Flibanserin in North American Premenopausal Women with Hypoactive Sexual Desire Disorder: Results from the Violet Trial, SMSNA, 2009, 3 pgs. (poster and abstract).

(56) References Cited

OTHER PUBLICATIONS

Sand, Effacacy of Flibanserin in North American Premenopausal Women with Hypoactive Sexual Desire Disorder: Results from the Violet Trial, SMSNA, 2009, 2 pgs. (oral presentation).
Meston, The Female Sexual Function Index (FSFI) is a Potential "Gold Standard" Measure for Assessing Sexual Function in Pre- and post-menopausal Women: a Systematic Review, SMSNA, 2009, 3 pgs. (oral presentation).
Goldfischer, Efficacy and Safety of Flibanserin in a Randomized Withdrawal Study of Premenopausal Women With Hypoactive Sexual Desire Disorder, WAS, 2009, 12 pgs. (oral presentation).
Goldfischer et al., Efficacy and Safety of Flibanserin in a Randomized Withdrawal Study of Premenopausal Women With Hypoactive Sexual Desire Disorder, WAS, 2009, 1 pgs. (abst.).
Clayton et al., Baseline Characteristics of Patients Enrolled in Three Phase III North American Trials of Flibanserin in Premenopausaul Women with Hypoactive Sexual Desire Disorder, WAS, 2009, 2 pgs. (poster and abstract).
Clayton, Baseline Characteristics of Patients Enrolled in Three Phase III North American Trials of Flibanserin in Premenopausaul Women with Hypoactive Sexual Desire Disorder, WAS, 2009, 4 pgs. (oral presentation).
Derogatis et al., Content Validity of the Female Sexual Distress Scale-Revised in Women With Hypoactive Sexual Desire Disorder, WAS, 2009, 1 pg. (abstract only).
Dennerstein et al., Attitudes Toward and Frequency of Partner Interactions Among Women Reporting Decreased Sexual Desire, J. Sex Med., 2009, 6:1668-1673.
Goldstein et al., National Differences in Patient-Clinician Communication Regarding Hypoactive Sexual Desire Disorder, J. Sex Med., 2009, 6:1349-1357.
Johannes et al., Distressing Sexual Problems in United States Women Revisited: Prevalence After Accounting for Depression, J. Clin. Psych., 2009, 70(12):1698-1706.
Pfaus, Pathways of Sexual Desire, J. Sex Med., 2009, 6:1506-1533.
Rosen et al., Correlates of Sexually Related Personal Distress in Women with Low Sexual Desire, J. Sex Med., 2009, 6:1549-1560.
Lewis-D'Agostino et al., Validating the Sexual Interest and Desire Inventory (SIDI-F) in North American Women, American College of Obstetricians and Gynecologists (ACOG) annual meeting, 2007, 1 pg. (poster).
Shifren et al., Help-Seeking Behavior of Women with Self-Reported Distressing Sexual Problems, J. of Women's Health, 2009, 18(4):461-468.
Wunderlich et al., Validity of Sexual Distress Scales vs Electronic Diary in Women with Decreased Sexual Desire, American College of Obstetricians and Gynecologists (ACOG) annual meeting, 2007, 1 pg. (poster).
Clayton et al., Using e-Diaries to Measure Sexual Desire in Women with Hypoactive Sexual Desire Disorder, European Society for Sexual Medicine (ESSM) annual meeting, 2007, 2 pgs. (abstract).
Van Lunsen et al., Validation of the Sexual Interest and Desire Inventory-Female (SIDI-F) in European Women, European Society for Sexual Medicine (ESSM) annual meeting, 2007, 1 pg. (abstract).
Clayton et al., Using e-Diaries to Measure Sexual Desire in Women with Hypoactive Sexual Desire Disorder, International Society for the Study of Womens Sexual Health (ISSWSH) annual meeting, 2007, 2 pgs. (abstract).
Van Lundsen, Validation of the Sexual Interest and Desire Inventory-Female (SIDI-F) in European women, ISSWSH, 2007, 2 pgs. (abstract).
Goldfischer et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (abstract).
Krychman et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 6 pgs. (poster and oral presentation).
Clayton et al., Baseline Characteristics of Patients Enrolled in Three Phase III North American Trials of Flibanserin in Premenopausal Women With Hypoactive Sexual Desire Disorder, FIGO 2009, Oct. 2009, 1 pg., Cape Town, South Africa. (abstract).
Scandroglio et al., Ex Vivo binding of Flibanserin to Serotonin-5-HT1A and 5-HT2A Receptors, Pharm. Res., 2001, 43(2):179-183.
D'Aquila et al., Anti-anhedonic actions of the novel serotonergic agent flibanserin, a potential rapidly-acting antidepressant, Euro. J. Pharm., 1997, 340:121-132.
Flik et al., Assessment of serotonin and catecholamine levels in the female rat brain following acute and chronic administration with flibanserin, a potential novel treatment for hypoactive sexual desire disorder: an in vivo microdialysis study, presented at Neuroscience 2009, Feb. 3, 2010, http://www.abstractsonline.com/Plan/AbstractPrintView.aspx?mID=2285&sKey=65206 . . . , 2 pgs.
Banfi et al., Benzimidazolone Derivatives: a new class of putative antidepressant agents, 13th Int. Symp. On Medicinal Chemistry, Sep. 19-23, 1994, p. 102. (abstract).
Borsini et la., BIMT 17, a 5-HT1A receptor agonist/5-HT2A receptor antagonist, directly activates portsynaptic 5-HT inhibitory responses in the rat cerebral cortex, Naunyn-Schmiedeberg's Arch Pharm., 1995, 352:283-290.
Boehringer Ingelheim, Flibanserin BIMT-17, Drugs of the Future, 1999, 24(1):91.
Podhorna et al., Flibanserin has anxiolytic effects without locomotor side effects in the infant rat ultrasonic vocalization model of anxiety, Workshop on Depression Anxiety Spectrum Disorders: from Neurobiology to Novel Pharm. Treatmts, Int. Acad. For Biomed. and Drug Res., Abstract-Book, Milan, Sep. 6-7, 2000, 1 pg.
Vaccarino et al., Flibanserin, a 5-HT1A agonist/5-HT2A antagonist, decreases sucrose intake in operant and non-operant paradigms in rats, Soc. Neurosci. Abstr., 2000, 26:394:Abstr 144.9, 30th Ann. Mtg. of Soc. For Neurosci, New Orleans, Nov. 4-9, 1000, 1 pg.
Borsini et al., Further characterisation of potential antidepressant action of flibanserin, Psychopharm., 2001, 159:64-69.
Rueter et al., In Vivo Electrophysiological Assessment of the Agonistic Properties of Flibanserin at Pre- and Postsynaptic 5-HT1A Receptors in the Rat Brain, Synapse, 1998, 29:392-405.
Cervo et al., Involvement of 5-HT1A receptors in flibanserin discriminative stimulus in female rats, Neurosci 2009, Feb. 3, 2010, http://www.abstractsonline.com/Plan/AbstratPrintView.aspx?mID=2285&sKey=65206 . . . , 2pgs.
Cervo et al., Involvement of 5-HT1A receptors in flibanserin discriminative stimulus in female rats, Dept. CNS Diseases, Prog. No. 465.20, 2009 Neurosci., Oct. 19, 2009, 1 pg. (poster).
Ferger et al., Neurochemical characterization of Flibanserin a phase III drug for treatment of hypoactive sexual desire disorder (HSDD) in women, Neurosci 2009, Feb. 3, 2010, http://www.abstractsonline.com/Plan/AbstractPrintView.aspx?mIK=2285&sKey=65206 . . . , 2pgs.
Flik et al., Assessment of serotonin and catecholamine levels in the female rat brain following acute and chronic administration with flibanserin, a potential novel treatment for hypoactive sexual desire disorder: An in vivo microdialysis study, SFN, 2009, 1 pg. (poster).
Ferger et al., Neurochemical characterization of Flibanserin a phase III drug for treatment of hypoactive sexual desire disorder (HSDD) in women, SFN, 2009, 1 pg. (poster).
Evans et al., The Effects of Flibanserin on Amphetamine Withdrawal-Induced hypolocomotion in Rats, Soc. Neurosci Abstr., Nov. 7-12, 1998, 24:2133:Abstr 848.5, 28th Ann. Mtg. of the Soc. For Neurosci, Los Angeles, 1 pg.
Advisory Action dated Dec. 27, 2005, U.S. Appl. No. 10/272,603, filed Oct. 16, 2002 now US Pat. No. 7151103, issued Dec. 19, 2006, 3 pgs.
Examiner's Interview dated Jun. 23, 2006, U.S. Appl. No, 10/272,603, filed Oct. 16, 2002 now US Pat. No. 7151103, issued Dec. 19, 2006, 2 pgs.
Examiner's Interview dated Oct. 20, 2005, U.S. Appl. No. 10/272,603, filed Oct. 16, 2002 now US Pat. No. 7151103, issued Dec. 19, 2006, 1 pg.
Final Office Action dated Jun. 2, 2005, U.S. Appl. No. 10/272,603, filed Oct. 16, 2002 now US Pat. No. 7151103, issued Dec. 19, 2006, 9 pgs.

(56) References Cited

OTHER PUBLICATIONS

Notice of Allowance dated Jun. 23, 2006, U.S. Appl. No. 10/272,603, filed Oct. 16, 2002 now US Pat. No. 7151103, issued Dec. 19, 2006, 7 pgs.
Notice of Appeal/Amendment dated Nov. 8, 2005, U.S. Appl. No. 10/272,603, filed Oct. 16, 2002 now US Pat. No. 7151103, issued Dec. 19, 2006, 9 pgs.
Office Action dated Oct. 14, 2004, U.S. Appl. No. 10/272,603, filed Oct. 16, 2002 now US Pat. No. 7151103, issued Dec. 19, 2006, 8 pgs.
RCE/Supp. Amendment dated Jun. 8, 2006, U.S. Appl. No. 10/272,603, filed Dec. 16, 2002 now US Pat. No. 7151103, issued Dec. 19, 2006, 29 pgs.
Reply dated Feb. 14, 2005, U.S. Appl. No. 10/272,603, filed Oct. 16, 2002 now US Pat. No. 7151103, issued Dec. 19, 2006, 20 pgs.
Examiner's Search Strategy dated Jun. 20, 2006, U.S. Appl. No. 10/272,603, filed Oct. 16, 2002 now US Pat. No. 7151103, issued Dec. 19, 2006, 2 pgs.
Examiner's Search Strategy dated Jun. 21, 2006, U.S. Appl. No. 10/272,603, filed Oct. 16, 2002 now US Pat. No. 7151103, issued Dec. 19, 2006, 20 pgs.
Examiner's Search Strategy dated Sep. 22, 2004, U.S. Appl. No. 10/272,603, filed Oct. 16, 2002 now US Pat. No. 7151103, issued Dec. 19, 2006, 83 pgs.
Examiner's Search Strategy dated Sep. 28, 2004, U.S. Appl. No. 10/272,603, filed Oct. 16, 2002 now US Pat. No. 7151103, issued Dec. 19, 2006, 117 pgs.
Examiner's Search Strategy dated Sep. 29, 2004, U.S. Appl. No. 10/272,603, filed Oct. 16, 2002 now US Pat. No. 7151103, issued Dec. 19, 2006, 1 pg.
Examiner's Search Strategy dated Oct. 14, 2004, U.S. Appl. No. 10/272,603, filed Oct. 16, 2002 now US Pat. No. 7151103, issued Dec. 19, 2006, 3pgs.
Final Office Action dated Oct. 5, 2005, U.S. Appl. No. 10/210,474, filed Aug. 1, 2002 now US Pat. No. 7183410, issued Feb. 27, 2007, 6 pgs.
Notice of Allowance dated Jan. 30, 2006, U.S. Appl. No. 10/210,474, filed Aug. 1, 2002 now US Pat. No. 7183410, issued Feb. 27, 2007, 7 pgs.
Notice of Allowance dated Jul. 12, 2006, U.S. Appl. No. 10/210,474, filed Aug. 1, 2002 now US Pat. No. 7183410, issued Feb. 27, 2007, 7 pgs.
Office Action dated Mar. 16, 2005, U.S. Appl. No. 10/210,474, filed Aug. 1, 2002 now US Pat. No. 7183410, issued Feb. 27, 2007, 9 pgs.
Office Action dated Jul. 26, 2004, U.S. Appl. No. 10/210,474, filed Aug. 1, 2002 now US Pat. No. 7183410, issued Feb. 27, 2007, 7 pgs.
Response to Final Office Action dated Dec. 15, 2005, U.S. Appl. No. 10/210,474, filed Aug. 1, 2002 now US Pat. No. 7183410, issued Feb. 27, 2007, 9 pgs.
Reply dated Jan. 26, 2005, U.S. Appl. No. 10/210,474, filed Aug. 1, 2002 now US Pat. No. 7183410, issued Feb. 27, 2007, 24 pgs.
Amendment dated Jul. 11, 2005, U.S. Appl. No. 10/210,474, filed Aug. 1, 2002 now US Pat. No. 7183410, issued Feb. 27, 2007, 13 pgs.
Examiner's Search Strategy dated Mar. 10, 2005, U.S. Appl. No. 10/210,474, filed Aug. 1, 2002 now US Pat. No. 7183410, issued Feb. 27, 2007, 36 pgs.
Examiner's Search Strategy dated Sep. 30, 2005, U.S. Appl. No. 10/210,474, filed Aug. 1, 2002 now US Pat. No. 7183410, issued Feb. 27, 2007, 6 pgs.
Reply with Amendment dated Mar. 8, 2005, U.S. Appl. No. 10/210,474, filed Aug. 1, 2002 now US Pat. No. 7183410, issued Feb. 27, 2007, 10 pgs.
Supplemental Amendment dated Jan. 19, 2006, U.S. Appl. No. 10/210,474, filed Aug. 1, 2002 now US Pat. No. 7183410, issued Feb. 27, 2007, 6 pgs.
Examiner's Interview dated Nov. 19, 2007, U.S. Appl. No. 11/546,303, filed Oct. 12, 2006, 3 pgs.
Final Office Action dated Sep. 14, 2007, U.S. Appl. No. 11/546,303, filed Oct. 12, 2006, 4 pgs.
Office Action dated Jan. 5, 2007, U.S. Appl. No. 11/546,303, filed Oct. 12, 2006, 7 pgs.
Response dated Jul. 5, 2007, U.S. Appl. No. 11/546,303, filed Oct. 12, 2006, 6 pgs.
Examiner's Search Strategy dated Mar. 10, 2005, U.S. Appl. No. 11/546,303, filed Oct. 12, 2006, 36 pgs.
Examiner's Interview Summ. Dated Jan. 17, 2008, U.S. Appl. No. 11/546,304, filed Oct. 12, 2006 now US Pat No. 7420057 issued Sep. 2, 2008, 3 pgs.
Notice of Allowance dated Apr. 30, 2008, U.S. Appl. No. 11/546,304, filed Oct. 12, 2006 now US Pat No. 7420057 issued Sep. 2, 2008, 8 pgs.
Office Action dated Jan. 3, 2007, U.S. Appl. No. 11/546,304, filed Oct. 12, 2006 now US Pat No. 7420057 issued Sep. 2, 2008, 7 pgs.
Office Action dated Jul. 18, 2007, U.S. Appl. No. 11/546,304, filed Oct. 12, 2006 now US Pat No. 7420057 issued Sep. 2, 2008, 4 pgs.
Response dated Jan. 17, 2008, U.S. Appl. No. 11/546,304, filed Oct. 12, 2006 now US Pat No. 7420057 issued Sep. 2, 2008, 24 pgs.
Response dated Apr. 3, 2007, U.S. Appl. No. 11/546,304, filed Oct. 12, 2006 now US Pat No. 7420057 issued Sep. 2, 2008, 7 pgs.
Supp. Response dated Mar. 19, 2008, U.S. Appl. No. 11/546,304, filed Oct. 12, 2006 now US Pat No. 7420057 issued Sep. 2, 2008, 13 pgs.
Supp. Response dated Mar. 24, 2008, U.S. Appl. No. 11/546,304, filed Oct. 12, 2006 now US Pat No. 7420057 issued Sep. 2, 2008, 14 pgs.
2nd Supp. Response dated Apr. 23, 2008, U.S. Appl. No. 11/546,304, filed Oct. 12, 2006 now US Pat No. 7420057 issued Sep. 2, 2008, 14 pgs.
Final Office Action dated Apr. 23, 2007, U.S. Appl. No. 11/079,070 filed Mar. 14, 2005, 11 pgs.
Notice of Allowance dated Sep. 14, 2007, U.S. Appl. No. 11/079,070, filed Mar. 14, 2005, 6 pgs.
Office Action dated Jan. 11, 2008, U.S. Appl. No. 11/079,070, filed Mar. 14, 2005, 8 pgs.
Office Action dated Sep. 13, 2006, U.S. Appl. No. 11/079,070, filed Mar. 14, 2005, 5 pgs.
Response to Final Office Action dated Jul. 23, 2007, U.S. Appl. No. 11/079,070, filed Mar. 14, 2005, 7 pgs.
RCE dated Nov. 2, 2007, U.S. Appl. No. 11/079,070, filed Mar. 14, 2005, 4 pgs.
Response dated Jan. 16, 2007, U.S. Appl. No. 11/079,070, filed Mar. 14, 2005, 8 pgs.
Examiner Search Strategy dated Jan. 3, 2008, U.S. Appl. No. 11/079,070, filed Mar. 14, 2005, 20 pgs.
Examiner's Search Strategy dated Jul. 21, 2006, U.S. Appl. No. 11/079,070, filed Mar. 14, 2005, 106 pgs.
Advisory Action dated Jul. 2, 2009, U.S. Appl. No. 11/278,551, filed Apr. 4, 2006, 3 pgs.
Final Office Action dated Apr. 13, 2009, U.S. Appl. No. 11/278,551, filed Apr. 4, 2006, 9 pgs.
Office Action dated Jun. 1, 2007, U.S. Appl. No. 11/278,551, filed Apr. 4, 2006, 9 pgs.
Office Action dated Jul. 6, 2006, U.S. Appl. No. 11/278,551, filed Apr. 4, 2006, 8 pgs.
Office Action dated Jul. 9, 2008, U.S. Appl. No. 11/278,551, filed Apr. 4, 2006, 12 pgs.
Office Action dated Dec. 28, 2009, U.S. Appl. No. 11/278,551, filed Apr. 4, 2006, 9 pgs.
Responsive Amendment to Final Office Action, dated Jun. 12, 2009, U.S. Appl. No. 11/278,551, filed Apr. 4, 2006, 63 pgs.
RCE and Responsive Amendment to Final Office Action, dated Oct. 7, 2009, U.S. Appl. No. 11/278,551, filed Apr. 4, 2006, 14 pgs.
Response dated Jan. 9, 2009, U.S. Appl. No. 11/278,551, filed Apr. 4, 2006, 64 pgs.
Response dated Nov. 30, 2007, U.S. Appl. No. 11/278,551, filed Apr. 4, 2006, 25 pgs.
Response dated Dec. 19, 2006, U.S. Appl. No. 11/278,551, filed Apr. 4, 2006, 4 pgs.
Examiner's Search Strategy dated Apr. 13, 2009, U.S. Appl. No. 11/278,551, filed Apr. 4, 2006, 2 pgs.
Examiner's Search Strategy dated Jun. 1, 2007, U.S. Appl. No. 11/278,551, filed Apr. 4, 2006, 10 pgs.
Examiner's Search Strategy dated Jun. 26, 2006, U.S. Appl. No. 11/278,551, filed Apr. 4, 2006, 19 pgs.

(56) References Cited

OTHER PUBLICATIONS

Examiner's Search Strategy dated Jul. 9, 2008, U.S. Appl. No. 11/278,551, filed Apr. 4, 2006, 6 pgs.
Examiner's Search Strategy dated Dec. 28, 2009, U.S. Appl. No. 11/278,551, filed Apr. 4, 2006, 3 pgs.
Final Office Action dated Sep. 12, 2008, U.S. Appl. No. 11/381,590, filed Apr. 4, 2006, 10 pgs.
Office Action dated Apr. 3, 2007, U.S. Appl. No. 11/381,590, filed Apr. 4, 2006, 8 pgs.
Office Action dated Dec. 27, 2007, U.S. Appl. No. 11/381,590, filed Apr. 4, 2006, 8 pgs.
Response dated Jun. 26, 2008, U.S. Appl. No. 11/381,590, filed Apr. 4, 2006, 7 pgs.
Amendment and Reply dated Oct. 3, 2007, U.S. Appl. No. 11/381,590, filed Apr. 4, 2006, 8 pgs.
Examiner's Search Strategy dated Mar. 30, 2007, U.S. Appl. No. 11/381,590, filed Apr. 4, 2006, 48 pgs.
Office Action dated Mar. 23, 2009, U.S. Appl. No. 11/383,796, filed May 17, 2006; 11 pgs.
Examiner's Search Strategy dated Mar. 23, 2009, U.S. Appl. No. 11/383,796, filed May 17, 2006; 2 pgs.
Office Action dated Mar. 19, 2009, U.S. Appl. No. 11/383,793, filed May 17, 2006, 12 pgs.
Examiner's Search Strategy dated Mar. 19, 2009, U.S. Appl. No. 11/383,793, filed May 17, 2006, 3 pgs.
Advisory Action dated Feb. 10, 2009, U.S. Appl. No. 11/381,130, filed May 2, 2006, 3 pgs.
Final Office Action dated Jul. 18, 2008, U.S. Appl. No. 11/381,130, filed May 2, 2006, 17pgs.
Office Action dated Oct. 9, 2007, U.S. Appl. No. 11/381,130, filed May 2, 2006, 13 pgs.
Response to Final Office Action dated Jan. 21, 2009, U.S. Appl. No. 11/381,130, filed May 2, 2006, 13 pgs.
Response dated Apr. 9, 2008, U.S. Appl. No. 11/381,130, filed May 2, 2006, 36 pgs.
Office Action dated Jun. 1, 2009, U.S. Appl. No. 11/364,306, filed Feb. 28, 2006, 18 pgs.
Examiner's Search Strategy dated Jun. 1, 2009, U.S. Appl. No. 11/364,306, 3 pgs.
Final Office Action dated Sep. 4, 2008, U.S. Appl. No. 11/364,153, filed Feb. 28, 2006, 12 pgs.
Office Action dated Nov. 29, 2007, U.S. Appl. No. 11/364,153, filed Feb. 28, 2006, 11 pgs.
Response dated May 29, 2008, U.S. Appl. No. 11/364,153, filed Feb. 28, 2006, 62 pgs.
Office Action dated Apr. 29, 2009, U.S. Appl. No. 11/364,785, filed Feb. 28, 2006, 23 pgs.
Examiner's Search Strategy dated Apr. 29, 2009, U.S. Appl. No. 11/364,785, filed Feb. 28, 2006, 19 pgs.
Office Action dated Apr. 9, 2009, U.S. Appl. No. 12/170,884, filed Jul. 10, 2008, 10 pgs.
Response dated Oct. 9, 2009, U.S. Appl. No. 12/170,884, filed Jul. 10, 2008, 3 pgs.
Examiner's Search Strategy dated Feb. 19, 2010, U.S. Appl. No. 12/170,884, filed Jul. 10, 2008, 26 pgs.
Examiner's Interview Summary dated Feb. 19, 2010, U.S. Appl. No. 12/170,884, filed Jul. 10, 2008, 4 pgs.
Notice of Allowance dated Feb. 19, 2010, U.S. Appl. No. 12/170,884, filed Jul. 10, 2008, 5 pgs.
Office Action dated Mar. 5, 2009, U.S. Appl. No. 11/740,959, filed Apr. 27, 2007, 30 pgs.
Response dated Sep. 3, 2009, U.S. Appl. No. 11/740,959, filed Apr. 27, 2007, 12 pgs.
Examiner's Search Strategy dated Mar. 5, 2009, U.S. Appl. No. 11/740,959, filed Apr. 27, 2007, 12 pgs.
Final Office Action dated Jan. 20, 2010; U.S. Appl. No. 11/740,959, filed Apr. 27, 2007, 33 pgs.
Examiner's Search Strategy dated Jan. 20, 2010, U.S. Appl. No. 11/740,959, filed Apr. 27, 2007, 6 pgs.
Office Action dated Apr. 13, 2009, U.S. Appl. No. 11/097,939, filed Apr. 4, 2005, 12 pgs.
Amendment and Response dated Sep. 14, 2009, U.S. Appl. No. 11/097,939, filed Apr. 4, 2005, 8 pgs.
Examiner's Search Strategy dated Apr. 13, 2009, U.S. Appl. No. 11/097,939, filed Apr. 4, 2005, 3 pgs.
Final Office Action dated Feb. 17, 2010, U.S. Appl. No. 11/097,939, filed Apr. 4, 2005, 16 pgs.
Examiner's Search Strategy dated Feb. 17, 2010, U.S. Appl. No. 11/097,939, filed Apr. 4, 2005, 2 pgs.
Office Action dated Mar. 19, 2009, U.S. Appl. No. 11/554,855, filed Oct. 31, 2006, 11 pgs.
Response dated Aug. 19, 2009, U.S. Appl. No. 11/554,855, filed Oct. 31, 2006, 7 pgs.
Examiner's Search Strategy dated Mar. 19, 2009, U.S. Appl. No. 11/554,855, filed Oct. 31, 2006, 3 pgs.
Office Action dated Dec. 4, 2009, U.S. Appl. No. 11/554,855, filed Oct. 31, 2006, 15 pgs.
Examiner's Search Strategy dated Dec. 4, 2009, U.S. Appl. No. 11/554,855, filed Oct. 31, 2006, 3 pgs.
Office Action dated Mar. 19, 2009, U.S. Appl. No. 11/745,515, filed May 8, 2007, 11 pgs.
Office Action dated Dec. 4, 2009, U.S. Appl. No. 11/745,515, filed May 8, 2007, 16 pgs.
Examiner's Search Strategy dated Mar. 19, 2009, U.S. Appl. No. 11/745,515, filed May 8, 2007, 3 pgs.
Response dated Aug. 19, 2009, U.S. Appl. No. 11/745,515, filed May 8, 2007, 8 pgs.
Examiner's Search Strategy dated Dec. 4, 2009, U.S. Appl. No. 11/745,515, filed May 8, 2007, 3 pgs.
Office Action dated Oct. 11, 2005, U.S. Appl. No. 10/882,613, filed Jul. 1, 2004, 7 pgs.
Examiner's Search Strategy dated Oct. 2, 2005, U.S. Appl. No. 10/882,613, filed Jul. 1, 2004, 17 pgs.
Advisory Action dated Mar. 16, 2007, U.S. Appl. No. 10/444,892, filed May 22, 2003, 2 pgs.
Advisory Action dated Mar. 29, 2007, U.S. Appl. No. 10/444,892, filed May 22, 2003, 3 pgs.
Examiner's Interview Summ. Dated Oct. 4, 2007, U.S. Appl. No. 10/444,892, filed May 22, 2003, 2 pgs.
Final Office Action dated Aug. 29, 2006, U.S. Appl. No. 10/444,892, filed May 22, 2003, 7 pgs.
Office Action dated Mar. 1, 2006, U.S. Appl. No. 10/444,892, filed May 22, 2003, 5 pgs.
Amendment After Final dated Feb. 28, 2007, U.S. Appl. No. 10/444,892, filed May 22, 2003, 8 pgs.
Amendment dated Jun. 27, 2006, U.S. Appl. No. 10/444,892, filed May 22, 2003, 5 pgs.
Office Action dated Jul. 2, 2007, U.S. Appl. No. 11/110,449, filed Apr. 20, 2005, 11 pgs.
Examiner's Search Strategy dated Jun. 20, 2007, U.S. Appl. No. 11/110,449, filed Apr. 20, 2005, 7 pgs.
Office Action dated Jun. 29, 2009, U.S. Appl. No. 11/960,957, filed Oct. 20, 2007, 12 pgs.
Response dated Dec. 29, 2009, U.S. Appl. No. 11/960,957, filed Oct. 20, 2007, 10 pgs.
Examiner's Search Strategy dated Jun. 29, 2009, U.S. Appl. No. 11/960,957, filed Oct. 20, 2007, 1 pgs.
Notice of Non-Compliant Amendment dated Mar. 10, 2010, U.S. Appl. No. 11/960,957, filed Oct. 20, 2007, 2 pgs.
Amendment and Response to Notice of Non-Compliant Amendment dated Apr. 9, 2010, U.S. Appl. No. 11/960,957, filed Oct. 20, 2007, 5 pgs.
Office Action dated Jan. 26, 2007, U.S. Appl. No. 11/178,716, filed Jul. 11, 2005, 8 pgs.
Office Action dated Apr. 14, 2006, U.S. Appl. No. 11/178,716, filed Jul. 11, 2005, 8 pgs.
Amendment dated Jul. 25, 2006, U.S. Appl. No. 11/178,716, filed Jul. 11, 2005, 5 pgs.
Examiner's Search Strategy dated Jan. 21, 2007, U.S. Appl. No. 11/178,716, filed Jul. 11, 2005, 1 pg.
Examiner's Search Strategy dated Mar. 30, 2006, U.S. Appl. No. 11/178,716, filed Jul. 11, 2005, 15 pgs.

(56) References Cited

OTHER PUBLICATIONS

Examiner's Search Strategy dated Apr. 11, 2006, U.S. Appl. No. 11/178,716, filed Jul. 11, 2005, 1 pg.
Final Office Action dated May 18, 2007, U.S. Appl. No. 11/218,107, filed Sep. 1, 2005, 11 pgs.
Office Action dated Aug. 15, 2006, U.S. Appl. No. 11/218,107, filed Sep. 1, 2005, 8 pgs.
Response dated Feb. 14, 2007, U.S. Appl. No. 11/218,107, filed Sep. 1, 2005, 4 pgs.
Examiner's Search Strategy dated Jun. 30, 2006, U.S. Appl. No. 11/218,107, filed Sep. 1, 2005, 8 pgs.
Examiner's Search Strategy dated Aug. 11, 2006, U.S. Appl. No. 11/218,107, filed Sep. 1, 2005, 2 pgs.
Office Action dated Aug. 26, 2008, U.S. Appl. No. 11/940,655, filed Nov. 15, 2007, 7 pgs.
Office Action dated Sep. 28, 2009, U.S. Appl. No. 11/997,567, filed Mar. 21, 2008, 7 pgs.
Examiner's Search Strategy dated Sep. 28, 2009, U.S. Appl. No. 11/997,567, filed Mar. 21, 2008, 43 pgs.
Response dated Feb. 19, 2010, U.S. Appl. No. 11/997,567, filed Mar. 21, 2008, 10 pgs.
Office Action dated Jan. 25, 2010, U.S. Appl. No. 11/837,957, filed Aug. 13, 2007, 11 pgs.
Examiner's Search Strategy dated Jan. 25, 2010, U.S. Appl. No. 11/837,957, 6 pgs.
Ferger et al., Flibanserin, a drug intended for treatment of hypoactive sexual desire disorder in pre-menopausal women, affects spontaneous motor activity and brain neurochemistry in female rates, Naunyn Schmiedebergs Arch Pharmacol., Apr. 27, 2010, pp. 1-17 (epub ahead of print).
Aubert et al., Comparison of Flibanserin With the 5-Ht1a Agonist (+)-8-Oh-Dpat in Affecting Interactions Between Male-Female Marmoset Pairs, J. Sex Med., May 2010, 7(s3):118. (abstract).
Aubert et al., Initial PET Assessment of Flibanserin-induced Neural Changes in Female Marmoset Monkeys, J. Sex Med., May 2010, 7(s3):131. (abstract).
Aubert et al., Chronic Treatment of Female Marmoset Monkeys with (+)-8-OH-DPAT or Flibanserin Differentially Alters Response of the Hypothalamic-Pituitary-Adrenal Axis to Restraint and Acute Serotonergic Challenge, J. Sex Med., May 2010, 7(s3):131. (abstract).
Gelez et al., Chronic Flibanserin Treatment Increases Solicitations in the Female Rat, J. Sex Med., May 2010, 7(s3):118. (abstract).
Allers et al., Acute and Repeated Flibanserin Administration in Female Rats Modulates Monoamines Differentially Across Brain Areas: A Microdialysis Study, J. Sex Med., Feb. 2010, 33 pgs. (Epub ahead of print).
Goldfischer et al., Efficacy of Continued Flibanserin Treatment on Sexual Desire, Satisfying Sexual Events and Sexual Functioning in Premenopausal Women With HSDD: Results From the Researching Outcomes on Sustained Efficacy (ROSE) Study, International Society for the Study of Womens Sexual Health (ISSWSH) annual meeting, 2008, 17 pgs. (oral presentation).
Final Office Action dated May 21, 2010, U.S. Appl. No. 11/997,567, filed Mar. 21, 2008, 7 pgs.
Final Office Action dated May 27, 2010, U.S. Appl. No. 11/278,551, filed Apr. 4, 2006, 8 pgs.
Examiner's Search Strategy dated May 27, 2010, U.S. Appl. No. 11/278,551, filed Apr. 4, 2006, 3 pgs.
Response dated Jun. 4, 2010, U.S. Appl. No. 11/554,855, filed Oct. 31, 2006, 10 pgs.
Response dated Jun. 4, 2010, U.S. Appl. No. 11/745,515, filed May 8, 2007, 8 pgs.
Restriction Requirement dated May 24, 2004 U.S. Appl. No. 10/210,474, filed Aug. 1, 2002 now US Pat. No. 7183410, issued Feb. 27, 2007, 6 pgs.
Response to Restriction Requirement dated Jun. 9, 2004 U.S. Appl. No. 10/210,474, filed Aug. 1, 2002 now US Pat. No. 7183410, issued Feb. 27, 2007, 2 pgs.
Restriction Requirement dated Aug. 20, 2008, U.S. Appl. No. 11/097,939, filed Apr. 4, 2005, 8 pgs.
Response to Restriction Requirement dated Feb. 12, 2009, U.S. Appl. No. 11/097,939, filed Apr. 4, 2005, 2 pgs.
Restriction Requirement dated Feb. 8, 2007, U.S. Appl. No. 11/110,449, filed Apr. 20, 2005, 8 pgs.
Response to Restriction Requirement dated Jun. 7, 2007, U.S. Appl. No. 11/110,449, filed Apr. 20, 2005, 2 pgs.
Restriction Requirement dated Dec. 23, 2008, U.S. Appl. No. 11/187,422, filed Jul. 22, 2005, 11 pgs.
Restriction Requirement dated May 23, 2007, U.S. Appl. No. 11/364,153, filed Feb. 28, 2006, 7 pgs.
Response to Restriction Requirement dated Sep. 24, 2007, U.S. Appl. No. 11/364,153, filed Feb. 28, 2006, 2 pgs.
Restriction Requirement dated Dec. 18, 2006, U.S. Appl. No. 11/381,590, filed Apr. 4, 2006, 7 pgs.
Response to Restriction Requirement dated Mar. 9, 2007, U.S. Appl. No. 11/381,590, filed Apr. 4, 2006, 2 pgs.
Restriction Requirment dated Aug. 18, 2008; U.S. Appl. No. 11/740,959, filed Apr. 27, 2007, 9 pgs.
Response to Restriction Requirment dated Nov. 18, 2008; U.S. Appl. No. 11/740,959, filed Apr. 27, 2007, 6 pgs.
Restriction Requirement dated Aug. 21, 2009, U.S. Appl. No. 11/837,957, filed Aug. 13, 2007, 7 pgs.
Response to Restriction Requirement dated Sep. 21, 2009, U.S. Appl. No. 11/837,957, filed Aug. 13, 2007, 2 pgs.
Restriction Requirement dated Jun. 21, 2010, U.S. Appl. No. 11/956,949, filed Dec. 14, 2007, 7 pgs.
Restriction Requirement dated Feb. 5, 2009, U.S. Appl. No. 11/960,957, filed Oct. 20, 2007, 8 pgs.
Response to Restriction Requirement dated Mar. 4, 2009, U.S. Appl. No. 11/960,957, filed Oct. 20, 2007, 2 pgs.
Restriction Requirement dated Jun. 30, 2009, U.S. Appl. No. 11/997,567, filed Mar. 21, 2008, 7 pgs.
Response to Restriction Requirement dated Jul. 23, 2009, U.S. Appl. No. 11/997,567, filed Mar. 21, 2008, 2 pgs.
Restriction Requirement dated May 4, 2010, U.S. Appl. No. 12/279,589, filed Sep. 26, 2008, 9 pgs.
RCE dated May 19, 2010, U.S. Appl. No. 12/170,884, filed Jul. 10, 2008, 3 pgs.
Examiner's Interview dated Apr. 15, 2009, U.S. Appl. No. 11/524,268, filed Sep. 21, 2006, 4pgs.
Examiner's Interview dated Oct. 23, 2007, U.S. Appl. No. 11/524,268, filed Sep. 21, 2006, 1 pg.
Notice of Allowance dated Jan. 11, 2010, U.S. Appl. No. 11/524,268, filed Sep. 21, 2006, 7 pgs.
Office Action dated Feb. 11, 2008, U.S. Appl. No. 11/524,268, filed Sep. 21, 2006, 15 pgs.
Office Action dated May 2, 2007, U.S. Appl. No. 11/524,268, filed Sep. 21, 2006, 10 pgs.
Office Action dated Dec. 1, 2008, U.S. Appl. No. 11/524,268, filed Sep. 21, 2006, 16 pgs.
Amendment dated Jun. 1, 2009, U.S. Appl. No. 11/524,268, filed Sep. 21, 2006, 64 pgs.
Response dated Aug. 11, 2008, U.S. Appl. No. 11/524,268, filed Sep. 21, 2006, 15 pgs.
Response dated Nov. 2, 2007, U.S. Appl. No. 11/524,268, filed Sep. 21, 2006, 32 pgs.
Examiner's Search Strategy dated Jan. 11, 2010, U.S. Appl. No. 11/524,268, filed Sep. 21, 2006, 5 pgs.
Examiner's Search Strategy dated Dec. 1, 2008, U.S. Appl. No. 11/524,268, filed Sep. 21, 2006, 4 pgs.
RCE dated Apr. 9, 2010, U.S. Appl. No. 11/524,268, filed Sep. 21, 2006, 2 pgs.
Office Action dated Jan. 11, 2010, U.S. Appl. No. 11/837,962, filed Aug. 13, 2007, 17 pgs.
Examiner's Search Strategy dated Jan. 11, 2010, U.S. Appl. No. 11/837,962, filed Aug. 13, 2007, 8 pgs.
Response dated Jun. 11, 2010 U.S. Appl. No. 11/837,962, filed Aug. 13, 2007, 16 pgs.
Restriction Requirement dated Sep. 9, 2009, U.S. Appl. No. 11/837,962, filed Aug. 13, 2007, 10 pgs.

(56) References Cited

OTHER PUBLICATIONS

Response to Restriction Requirement dated Sep. 25, 2009, U.S. Appl. No. 11/837,962, filed Aug. 13, 2007, 2 pgs.
Office Action dated Jan. 14, 2010, U.S. Appl. No. 12/091,848, filed Apr. 28, 2008, 5 pgs.
Examiner's Search Strategy dated Jan. 14, 2010, U.S. Appl. No. 12/091,848, filed Apr. 28, 2008, 47 pgs.
Response dated Jun. 14, 2010 U.S. Appl. No. 12/091,848, filed Apr. 28, 2008, 5 pgs.
Restriction Requirement dated Oct. 7, 2009, U.S. Appl. No. 12/091,848, filed Apr. 28, 2008, 5 pgs.
Response to Restriction Requirement dated Nov. 9, 2009, U.S. Appl. No. 12/091,848, filed Apr. 28, 2008, 9 pgs.
Notice of Non-Compliant Amendment dated Jun. 22, 2010 U.S. Appl. No. 12/091,848, filed Apr. 28, 2008, 2 pgs.
Response to Notice of Non-Compliant Amdmt dated Jun. 23, 2010 U.S. Appl. No. 12/091,848, filed Apr. 28, 2008, 6 pgs.
Final Office Action dated Jul. 9, 2010; U.S. Appl. No. 11/960,957, filed Dec. 20, 2007, 9 pgs.
Response to Final Office Action dated Jul. 20, 2010; U.S. Appl. No. 11/740,959, filed Apr. 27, 2007, 14 pgs.
Response to Office Action dated Jul. 26, 2010; U.S. Appl. No. 11/837,957, filed Aug. 13, 2007, 11 pgs.
Restriction Requirement dated Oct. 4, 2005; U.S. Appl. No. 10/444,892, filed May 22, 2003, 7 pgs.
Response to Restriction Requirement dated Dec. 1, 2003; U.S. Appl. No. 10/444,892, filed May 22, 2003, 2 pgs.
RCE dated Jul. 20, 2010; U.S. Appl. No. 11/740,959, filed Apr. 27, 2007, 3 pgs.
Response to Final Office Action dated Aug. 17, 2010; U.S. Appl. No. 11/097,939, filed Apr. 4, 2005, 22 pgs.
RCE dated Aug. 17, 2010; U.S. Appl. No. 11/097,939, filed Apr. 4, 2005, 3 pgs.
Freeman et al., Differential Response to Antidepressants in Women With Premenstrual Syndrome/Premenstrual Dysphoric Disorder, Arch Gen Phych, 1999, 56:932-939.
Richelson, Pharmacology of Antidepressants, Mayo Clin Proc., 2001, 76:511-527.
U.S. Appl. No. 13/131,926, May 31, 2011, Mazurek et al.
Eriksson, Serotonin reuptake inhibitors for the treatment of premenstrual dysphoria, Intl. Clin. Psychopharm, 1999, 14Supp2:S27-S33.
Steiner et al., Seretonin re-uptake inhibitors in the treatment of premenstrual dysphoria: Current status of knowledge, 1997, 1:241-247.
Advisory Action dated Feb. 17, 2011; U.S. Appl. No. 11/837,957, filed Aug. 13, 2007, 3 pgs.
Notice of Appeal dated Feb. 22, 2011; U.S. Appl. No. 11/745,515, filed May 8, 2007, 1 pgs.
Notice of Appeal dated Feb. 22, 2011; U.S. Appl. No. 11/554,855, filed Oct. 31, 2006, 1 pgs.
Advisory Action dated Mar. 2, 2011; U.S. Appl. No. 11/745,515, filed May 8, 2007, 3 pgs.
Advisory Action dated Mar. 2, 2011; U.S. Appl. No. 11/554,855, filed Oct. 31, 2006, 3 pgs.
RCE dated Mar. 7, 2011; U.S. Appl. No. 11/837,957, filed Aug. 13, 2007, 2 pgs.
Response to Final Office Action dated Mar. 7, 2011; U.S. Appl. No. 11/837,957, filed Aug. 13, 2007, 9 pgs.
Response to Office Action dated Mar. 14, 2011; U.S. Appl. No. 11/097,939, filed Apr. 4, 2005, 20 pgs.
Interview Summary dated Mar. 15, 2011; U.S. Appl. No. 11/097,939, filed Apr. 4, 2005, 4 pgs.
Interview Summary dated Apr. 6, 2011; U.S. Appl. No. 11/997,567, filed Mar. 21, 2008, 3 pgs.
Response/Amendment dated Apr. 12, 2011; U.S. Appl. No. 11/997,567, filed Mar. 21, 2008, 9 pgs.
Final Office Action dated Apr. 19, 2011, U.S. Appl. No. 11/278,551, filed Apr. 4, 2006, 9 pgs.
Response to Office Action dated May 2, 2011; U.S. Appl. No. 12/390,665, filed Feb. 23, 2009, 11 pgs.
Office Action dated May 27, 2011, U.S. Appl. No. 12/170,884, filed Jul. 10, 2008, 6 pgs.
Office Action dated May 31, 2011; U.S. Appl. No. 11/097,939, filed Apr. 4, 2005, 15 pgs.
Final Office Action dated Jun. 16, 2011; U.S. Appl. No. 11/956,949, filed Dec. 14, 2007, 7 pgs.
Final Office Action dated Jun. 23, 2011; U.S. Appl. No. 11/997,567, filed Mar. 21, 2008, 7 pgs.
Restriction Requirement dated Jun. 29, 2011, U.S. Appl. No. 12/306,945, filed Feb. 9, 2009, 7 pgs.
Berge et al., Pharmaceutical Salts, J Pharm Sci., 1977, 66(1):1-19.
Kumar et al., An Overview of Automated Systems Relevant in Pharmaceutical Salt Screening; Drug Discovery Today, 2007, 12(23-24):1046-1053.
Stahl et al., Handbook of Pharmaceutical Salts: Selection and Use, Helvetica Chim. Acta, 2002, pp. 1-7.
FDA (U.S. Food and Drug Administration); Reproductive Health Drugs Advisory Committee Meeting Announcement; URL: http://www.fda.gov/AdvisoryCommittees/Calendar/ucm210886.htm; Jun. 18, 2010; 1 pg.
Background Document for Meeting of Advisory Committee for Reproductive Health Drugs (Jun. 8, 2010); NDA 22-526 Flibanserin; Boehringer Ingelheim; May 20, 2010; 80 pgs.
Briefing Document; Flibanserin (BIMT 17 BS); Boehringer Ingelheim; May 14, 2010; 248 pgs.
FDA (U.S. Food and Drug Administration); Reproductive Health Drugs Advisory Committee Meeting; Draft Agenda; Jun. 18, 2010; 1 pg.
FDA (U.S. Food and Drug Administration); Reproductive Health Drugs Advisory Committee Meeting; Draft Questions to the Committee; Jun. 18, 2010; 1 pg.
FDA (U.S. Food and Drug Administration); Reproductive Health Drugs Advisory Committee Meeting; Draft Meeting Roster; Jun. 18, 2010; 2 pgs.
Advisory Committee for Reproductive Health Drugs—2010 Members; Jun. 2010; 2 pgs.
FDA (U.S. Food and Drug Administration); Reproductive Health Drugs Advisory Committee Meeting; Agenda; Jun. 18, 2010; 2 pgs.
FDA (U.S. Food and Drug Administration); Reproductive Health Drugs Advisory Committee Meeting; Questions to the Committee; Jun. 18, 2010; 1 pg.
FDA (U.S. Food and Drug Administration); Reproductive Health Drugs Advisory Committee Meeting; Meeting Roster; Jun. 18, 2010; 2 pgs.
(Slides) Division of Reproductive and Urologic Drug Products Advisory Committee Meeting; Flibanserin (NDA-22526); Boehringer Ingelheim; Jun. 18, 2010; 110 pgs.
Press Release May 19, 2010; women with hypoactive sexual desire disorder (HSDD) report that fibanserin increased their sexual desire and reduced associated distress; http://www.boehringer-ingelheim.com/news/news releases/press releases/2010/19 May 2010; 4 pgs.
Press Release Jun. 17, 2010; Key Facts on HSDD and Flibanserin; http://us.boerhinger-ingelheim.com/news events/press releases/press release archive/2010; 2 pgs.
Press Release Jun. 18, 2010; Boehringer Ingelheim comments on Jun. 18 FDA Advisory Committee Meeting; http://us.boehringer-ingelheim.com/news events/press releases; press release archive/2010; 2 pgs.
FDA (U.S. Food and Drug Administration); Transcript of Advisory Committee for Reproductive Health Drugs; Jun. 18, 2010; 293 pgs.
Anderson et al., Guidelines for choice of selective serotonin reuptake inhibitor in depressive illness, Adv. Psychia. Treatment, 2001, 7:170-180.
Werneke et al., Antidepressants and sexual dysfuntion, Acta Psychia. Scand, 2005, 114:384-397.
U.S. Appl. No. 12/987,388, filed Jan. 10, 2011, Pyke.
Anonymous, Gel significantly increases sexual-activity in surgically menopausal women, Online, Nov. 1, 2004, XP002455243, Retrieved from the Internet: URL:http/www.news-medical.net/print_article.asp?id=5960>[retrieved on Oct. 17, 2007] 8 pgs.
Yekimov, Sex toys and devices in sexual dysfunction therapy, www.mosmedclinic.ru/conf_library/2002/2/130/, 2002, 6 pgs.

(56) References Cited

OTHER PUBLICATIONS

Response to Final Office Action dated Sep. 27, 2010 U.S. Appl. No. 11/278,551, filed Apr. 4, 2006, 8 pgs.
Interview Summary dated Jul. 19, 2010; U.S. Appl. No. 11/740,959, filed Apr. 27, 2007, 3pgs.
Final Office Action dated Aug. 20, 2010 U.S. Appl. No. 11/745,515, filed May 8, 2007, 7 pgs.
Final Office Action dated Aug. 30, 2010 U.S. Appl. No. 11/554,855, filed Oct. 31, 2006, 10 pgs.
Notice of Missing Requirements dated Aug. 24, 2010 U.S. Appl. No. 12/675,231, filed Feb. 25, 2010, 2 pgs.
Interview Summary dated Aug. 25, 2010 U.S. Appl. No. 11/278,551, filed Apr. 4, 2006, 3 pgs.
Final Office Action dated Sep. 13, 2010, U.S. Appl. No. 11/837,962, filed Aug. 13, 2007, 20 pgs.
Office Action dated Sep. 14, 2010; U.S. Appl. No. 11/097,939, filed Apr. 4, 2005, 18 pgs.
Notice of Allowance dated Sep. 20, 2010 U.S. Appl. No. 12/091,848, filed Apr. 28, 2008, 7 pgs.
Final Office Action dated Oct. 6, 2010; U.S. Appl. No. 11/837,957, filed Aug. 13, 2007, 10 pgs.
Response to Final Office Action dated Oct. 12, 2010; U.S. Appl. No. 11/960,957, filed Dec. 20, 2007, 16 pgs.
Interview Summary dated Oct. 19, 2010; U.S. Appl. No. 11/997,567, filed Mar. 21, 2008, 3 pgs.
Response to Final Office Action dated Oct. 21, 2010; U.S. Appl. No. 11/997,567, filed Mar. 21, 2008, 8 pgs.
RCE dated Oct. 21, 2010; U.S. Appl. No. 11/997,567, filed Mar. 21, 2008, 2 pgs.
Interview Substance dated Oct. 21, 2010; U.S. Appl. No. 11/997,567, filed Mar. 21, 2008, 1 pg.
Office Action dated Oct. 26, 2010, U.S. Appl. No. 11/278,551, filed Apr. 4, 2006, 10 pgs.
Office Action dated Nov. 5, 2010; U.S. Appl. No. 11/956,949, filed Dec. 14, 2007, 10 pgs.
Advisory Action dated Nov. 8, 2010; U.S. Appl. No. 11/960,957, filed Dec. 20, 2007, 3 pgs.
Acknowledgment of Priority Document dated Nov. 4, 2010; U.S. Appl. No. 12/091,848, filed Apr. 28, 2008, 1 pg.
Office Action dated Nov. 12, 2010; U.S. Appl. No. 11/997,567, filed Mar. 21, 2008, 7 pgs.
Notice of Allowance dated Nov. 15, 2010; U.S. Appl. No. 12/091,848, filed Apr. 28, 2008, 4 pgs.
RCE dated Dec. 20, 2010; U.S. Appl. No. 12/091,848, filed Apr. 28, 2008, 3 pgs.
Office Action dated Dec. 30, 2010; U.S. Appl. No. 12/390,665, filed Feb. 23, 2009, 9 pgs.
Response to Final Office Action dated Jan. 20, 2011; U.S. Appl. No. 11/745,515, filed May 8, 2007, 7 pgs.
Response to Final Office Action dated Jan. 20, 2011; U.S. Appl. No. 11/554,855, filed Oct. 31, 2006, 9 pgs.
Response to Office Action dated Jan. 28, 2011, U.S. Appl. No. 11/278,551, filed Apr. 4, 2006, 7 pgs.
Response to Final Office Action dated Feb. 7, 2011; U.S. Appl. No. 11/837,957, filed Aug. 13, 2007, 9 pgs.
RCE dated Feb. 15, 2011; U.S. Appl. No. 11/837,962, filed Aug. 13, 2007, 2 pgs. (62).
Response to Final Office Action dated Feb. 15, 2011; U.S. Appl. No. 11/837,962, filed Aug. 13, 2007, 15 pgs. (62).
Notice of Allowance dated Feb. 16, 2011; U.S. Appl. No. 12/091,848, filed Apr. 28, 2008, 8 pgs. (35).
Aizenberg et al, "Cyproheptadine Treatment of Sexual Dysfunction Induced by Serotonin Reuptake Inhibitors," Clinical Neuropharmacology, vol. 18, No. 4, pp. 320-324, 1995 Lippincott-Raven Publishers, Philadelphia.
Archer, T.; "5-HT, Pain and Anxiety" Behavioural Pharmacology of 5-HT, pp. 299-300 (1989).
Chemical Abstract 88-98788c (Apr. 10, 1978),Awouters et al, "Oxatomide, a new orally active drug which inhibits both the release and the effects of allergic mediators,".

Backhauss et al., "A Mouse Model of Focal Cerebral Ischemia for Screening Neuroprotective Drug Effects," Journal of Pharmacological Methods 27, 1992, pp. 27-32.
Basson, R. et al; "Report of the international consensus development conference on female sexual dysfunction: definitions and classifications;" The Journal of Urology; vol. 163 pp. 888-893, Mar. 2000.
Baxter,G., "5-$HT_2$ Receptor Subtypes: a family re-united?", Trends in Pharmacological Sciences, Elsevier, Hayworth, GB, vol. 16, No. 3, Mar. 1995, pp. 105-110.
Beers, M.H. et al; The Merck Manual of Diagnosis and Therapy; 17th Ed., 1999, pp. 1595-1598.
Bernstein, J. et al; "Concomitant Polymorphs"; Angewandte Chemie, Int. Ed., 1999, pp. 3441-3461.
Bevan et al; "5-HT and sexual behaviour" Behavioural Pharmacology of 5-HT, pp. 33-34, 87-88 (1989).
Borsini, F. et al; Behavioral Effects of Flibanserin (BIMT 17), Sep. 1999, Pharmacology, Biochemistry and Behavior, vol. 64, Issue 1, abstract.
Borsini, F. et al; Behavioral Effects of Flibanserin (BIMT 17), Sep. 1999, Pharmacology Biochemistry and Behavior, vol. 64, Issue 1, pp. 137-146.
Borsini, F. et al; "Flibanserin," Drugs of the future, (1998) vol. 23 (1) pp. 9-16.
Borsini, F. et al; "BIMT 17, a 5-$HT_{2A}$ receptor antagonist and 5-$HT_{1A}$ receptor full agonist in rat cerebral cortex"; Naunyn-Schmiedeberg's Archives of Pharm., 1995, 352 pp. 276-282.
Borsini, F. et al; "Lack of interaction between flibanserin and antidepressants in inducing serotonergic syndrome in rats" International Journal of Neuropsychopharmacology (2001) pp. 9-15, vol. 4, No. 1, University Press, Cambridge, GB.
Borsini, F. et al, "Mechanism of action of flibanserin in the learned helplessness paradigm in rats," European Journal of Pharmacology 433:81-89 (2001).
Borsini, F. et al; "Pharmacology of Flibanserin" CNS Drug Reviews 2002; vol. 8, No. 2, pp. 117-142.
Borsini, F. et al., "BIMT 17: a putative antidepressant with a fast onset of action?" Psychopharmacology (1997) 134:378-386.
Brambilla et al., "Effect of Flibanserin (BIMT 17), fluoxetine 8-OH-DPAT and busprione on serotonin synthesis in rat brain," Europ. Neuropsychopharmacology, Vo. 10, No. 1, 1999, pp. 63-67.
Carey, John, "Viagra for Women?" Business Week.com (Dec. 28, 2006).
R. Cesana et al; "The effect of MIMT 17, a new potential antidepressant, in the forced swimming test in mice" Behavioral Pharmacology (1995) pp. 688-694, vol. 6. Rapid Science Publishers, GB.
Chalmers et al; "Corticotrophin-releasing factor receptors: from molecular biology to drug design" TiPS vol. 17 pp. 166-72, Apr. 1996.
Chemical Abstracts Service, Columbus 1978, Damir et al., "Hemodynamic effects of pharmacological block during acute overload of the heart" Database accession # 1978:591197 XP-002436715.
Chemical Abstract: Database, Collino, F. et al; accession No. 98:16650: "Mannich bases of bensimidazoles, benzotriazoles and other analogous compounds, with pharmacological activity."-XP 002197885, dated 1983.
Cloninger, C.R.; "A systematic method for clinical description and classification of personality variants" Arch. Gen. Psychiatry, vol. 44 pp. 573-588 (Jun. 1987).
Cools, A.R.; "Depression and psychosis" Behavioural Pharmacology of 5-HT, pp. 153-155 (1989).
Cremers and Boehm, "Non Erectile Dysfunction Application of Sildenafil", Herz, vol. 28, No. 4, pp. 325-333, 2003.
Crook, T. and Larkin, M.; "Effects of ondansertron in age-associated memory impairment" The role of ondansetron, a novel 5-HT3 antagonist, in the treatment of psychiatric disorders, 5th World Congress of Biochemical Psychiatry, pp. 21-23 (1991).
Cyr, Monica et al; "Nefazodone: Its place among antidepressants," Annals of Pharmacotherapy, vol. 30 No. 9 pp. 1006-1012; 1996.
Chemical Abstract 118-124537e Damour et al, "Preparation and formulation of 1[(4-phenylpiperazino)alkyl]benzimidazolin-2-ones and analogs as serotonin $S_2$ antagonists"( Mar. 29, 1993).

(56) References Cited

OTHER PUBLICATIONS

Darlington, C.; "Flibanserin Boehringer Ingelheim Corp."; Current Opinion in CPNS investigational drugs vol. 1, No. 4, 1999, pp. 510-513; Pharma Press Ltd, London, GB.

De Vry, J.;"5-$HT_{1A}$ receptors in psychopathology and the mechanism of action of clinically effective therapeutic agents" Drug News and Perspectives 1996, vol. 9 No. 5 pp. 270-280.

Deangelis, L.; "5-$HT_{2A}$ antagonists in psychiatric disorders;" Current Opinion in Investigational Drugs 2002; vol. 3 No. 1 pp. 106-112; ISSN: 1472-4472.

Dimmock, P. et al; "Efficacy of selective serotonin-reuptake inhibitors in premenstrual syndrome: A systematic review" The Lancet, vol. 356, No. 9236 pp. 1131-1136, Sep. 30, 2000.

Fourcroy, Jean L. ; "Female sexual dysfunction: potential for pharmaotherapy" Drugs 2003, vol. 63 No. 14 pp. 1445-1457.

Frampton, et al; "Pentoxifylline ( Oxpentifyiline) A Review of its Therapeutic Efficacy in the Management of Peripheral Vascular and Cerebrovascular Disorders;" (Drug Evaluation) Drugs and Aging 7 (6) pp. 480-503, 1995.

Fujikura et al; "Effects of naftidrofuryl oxalate, a 5-HT2 antagonist, on neuronal damage and local cerebral blood flow following transient cerebral ischemia in gerbils;" Brain Research 636 (1994) pp. 103-106.

Geyer, M.; "5-$HT_2$ antagonists increase tactile startle habituation in an animal model of habituation deficit in schizophrenia" Behavioural Pharmacology of 5-HT, pp. 243-246 (1989).

Giron, D; "Thermal analysis and calorimetric methods in the characterisation of polymorphs and solvates"; Thermochimica ACTA, Elsevier Science; 248; 1995; pp. 1-59.

Goa, et al; "Buspirone. A preliminary review of its pharmacological properties and therapeutic efficacy as an anxiolytic;" Drugs 1986 vol. 32 pp. 114-129.

Gonzales, "Natural Compound May Offer New Treatment for Chronic Pain" NIDA Notes, vol. 16, No. 3-Aug. 2001, www.nida.nih.gov/NIDA_Notes/NNVol16N3/Natural.htm.

Gould;"Salt selection for basic drugs;" International Journal of Pharmaceutics; vol. 33, Issue 1-3, pp. 201-217, Nov. 1986.

Greene, T.; "Protective groups in organic synthesis:", Harvard University pp. 10-17 (1981), Wiley-Interscience Publication).

Hansenne, M. et al; "Harm avoidance dimension of the tridimensional personality questionnaire and serotonin-1A activity in depressed patients;" Biol. Psychiatry 1997, vol. 42 pp. 959-961.

Invernizzi et al,"Flibanserin, a potential antidepressant drug, lowers 5-HT and raises dopamine and noradrenaline in the rat prefrontal cortex dialysate: role of 5-$HT_{1A}$ receptors"; British Journal of Pharmacology, vol. 139 pp. 1281-1288, Jun. 2003.

Kleven, M., "Modification of behavioral effects of 8-hydroxy-2-(di-n-propylamino) tetralin following chronic ethanol consumption in the rat: evidence for the involvement of 5-$HT_{1A}$ receptors in ethanol dependence.", European Journal of Pharmacology, 1995, vol. 281, No. 3, pp. 219-228.

CAPLUS abstract 1999:285050, Koba, "Involvement of peripheral 5-$HT_{2A}$ receptor activation in pain behavior evoked by formalin paw injection in the rat," Kyushu Shika Gakkai Zaahi 53(1):253-60 (1999).

Lammers, GJ. et al; "Ritanserin, a 5-$HT_2$ receptor blocker, as add on treatment in narcolepsy;" Sleep 1991, vol. 14, No. 2 pp. 130-132.

Leonard, B.E.; "Sub-types of serotonin receptors: biochemical changes and pharmacological consequences" International Clinical Psychopharmacology 7, pp. 13-21 (1992).

Lyrer, "Neue Ansatze in der Akutbehandlung des zerebrovaskularen Insultes(New Approaches in the Acute Treatment of Cerebrovascular Insult)" Schweiz. Med. Wochenschr. vol. 124 No. 45 pp. 2005-2012 (1994).

Marazziti, Donatella et al; "Region-dependent effects of flibanserin and buspirone on adenylyl cyclase activity in the human brain" Int'l Journal of Neuropsychopharmacology, Jun. 2002, p. 131-140, vol. 5, No. 2.

Martindale: "Anxiolytic Sedatives Hypnotics and Antipsychotics" The complete drug reference, 1999, p. 635, Pharmaceutial Press, London 32.

McCall, RB. et al; "Role of serotonin 1A and serotonin 2 receptors in the central regulation of the cardiovascular system;" Pharmacological Reviews 1994, vol. 46 No. 3 pp. 231-243.

Merriam Webster New Collegiate Dictionary, definition of Diagnosis, 1981, p. 311.

Meston and Gorzalka, "Psychoactive Drugs and Human Sexual Behavior: The Role of Serotonergic Activity," Journal of Psychoactive Drugs, vol. 24(1), Jan.-Mar. 1992 pp. 1-40.

"The Merck Manual of diagnosis and therapy", Merck Research Laboratories, USA 1999, p. 1410, col. 1-p. 1413, col. 2, paragraph 1; p. 1412, tables 173-2 XP-002439435.

Miranda, et al., Dexketoprofen-Induced antinociception in animal models of acute pain: Synergy with morphine and paracetamol; Neuropharmacology 52 (2007) 291-296.

Moynihan, R., "The making of disease: female sexual dysfunction" British Medical Journal, 2003. vol. 326, pp. 45-47.

Nadeson, et al., "Antinociceptive role of 5-$HT_{1A}$ receptors in rat spinal cord" Laboratory Investigations, British Journal of Anaesthesia 88(5):679-84 (2002).

Okamoto et al., "5-HT2A receptor subtype in the peripheral branch of sensory fibers is involved in the potentiation of inflammatory pain in rats," Pain 99 (2002) 133-143.

Petkov, V.D. et al; "Participation of different 5-HT receptors in the memory process in rats and its modulation by the serotonin depletory p-chlorophenylalanine;" Acta Neurobiol. Exp. 1995 vol. 55 pp. 243-252.

Philips & Slaughter; "Depression and Sexual Desire," American Family Physician, vol. 62/No. 4, Aug. 15, 2000.

Podhorna, J. et al; "Flibanserin has anxiolytic effects without locomotor side effects in the infant rat ultrasonic vocalization model of anxiety;" British Journal of Pharacology (2000) vol. 130 No. 4 pp. 739-746.

Prehn et al; "Neuroprotective properties of 5-HT1A receptor agonists in rodent models of focal and global cerebral ischemia;" European Journal of Pharmacology, 203 (1991) 213-222.

Prehn et al., "Effects of serotonergic drugs in experimental brain ischemia: evidence for a protective role of serotonin in cerebral ischemia;" Brain Research 630 (1993) pp. 10-20.

Riekkinen et al; "The effects of increased serotonergic and decreased cholinergic activities on spatial navigation performance in rats" Pharmacology Biochemistry & Behavior, vol. 39 pp. 25-29 (1991).

Rueter, L.E. et al; "Electrophysiological examination of the effects of sustained flibanserin administration on serotonin receptors in rat brain;" British J. of Pharm, 1999, vol. 126, No. 3, pp. 627-638.

Risch, S. Craig et al; "Neurochemical alterations of serotonergic neuronal systems in depression;" J. Clin. Psychiatry 1992, vol. 53 No. 10 Suppl. 3-7.

Robinson, D.S. "Serotonin receptor subtypes and affective disorders;" Clinical Neuropharmacology 1993, vol. 16 No. Suppl. 3 pp. S1-S5.

Rosland et al., "The formalin test in mice: effect of formalin concentration," Pain 42 (1990) 235-242.

Shibata et al., "Ischemia-induced impairment of 2-deoxyglucose uptake and CA1 field potentials in rat hippocampal slices: protection by 5-HT1A receptor agonists and 5-HT2 receptor antagonists;" European Journal of Pharmacology, 229 (1992) pp. 21-29.

Shipton, B. et al., "Valvular heart disease: review and update," American Family PhysicianJun. 1, 2001, vol. 63 # 11, pp. 2201-2208.

Sietsema, D. et al, "From Taboo to Treatment?" Good Clinical Practice Journal, Jan. 2005, vol. 12, # 1, pp. 23-27.

Spine-health.com, Types of Back Pain: Acute Pain, Chronic Pain and Neuropathic Pain, www.spine-health.com/topics/cd/chronic_pain/chronicpain02.html, Oct. 2, 2007.

Steiner, M., Recognition of Premenstrual Dysphoric Disorder and Its Treatment; The Lancet, vol. 356, No. 9236, Sep. 30, 2000, pp. 1126-1127.

Vandenberk et al; Piperazine and piperidine derivatives, Chemical Abstract 88-50920n (Jan. 30, 1978).

(56) References Cited

OTHER PUBLICATIONS

Walsh K. et al., "Sexual dysfunction in the older women and overview of the current understanding and management" Drugs and Aging, 2004, vol. 21, # 10 pp. 655-675.

Zajecka, John et al; "Sexual function and satisfaction in the treatment of chronic major depression with nefazodone, psychotherapy, and their combination;" Journal Clin. Psychiatry, vol. 63 No. 8 pp. 709-716, Aug. 2002.

U.S. Appl. No. 11/956,949, filed Dec. 14, 2007, D. Lewis-D'Agostino et al.

U.S. Appl. No. 11/960,957, filed Dec. 20, 2007, Klaus Mendla et al.

U.S. Appl. No. 11/940,655, filed Nov. 15, 2007; Dolsten, Mikael.

U.S. Appl. No. 11/997,567, filed Feb. 1, 2008, Ceci, Angelo.

\* cited by examiner step b)

Step c)

step d)

step e)

step f)

Step d)

step e)

step f)

step b)

Step c)

step d)

step e)

EXTENDED RELEASE TABLET FORMULATIONS OF FLIBANSERIN AND METHOD FOR MANUFACTURING THE SAME

This application claims the benefit of priority to EP 06 118 896, filed Aug. 14, 2006, and EP 06 017 754, filed Aug. 25, 2006, the contents of which are incorporated herein by reference in its entirety.

FIELD OF THE INVENTION

The present invention is directed to pharmaceutical release systems, particularly for oral administration of flibanserin, and a method for the production thereof.

BACKGROUND OF THE INVENTION

The invention relates to novel pharmaceutical release systems for basic drugs with pH-dependent water solubility such as flibanserin. Flibanserin is a known benzimidazolon derivative having the summation formula $C_{20}H_{21}F_3N_4O$ represented by the chemical indication 1,3-dihydro-1-[2-[4-[3-(trifluoromethyl)phenyl]-1-piperazinyl]ethyl]-2H-benzimidazole-2-one which was already disclosed in 1992 in form of its hydrochloride in EP-A-526 434 and has the following chemical formula:

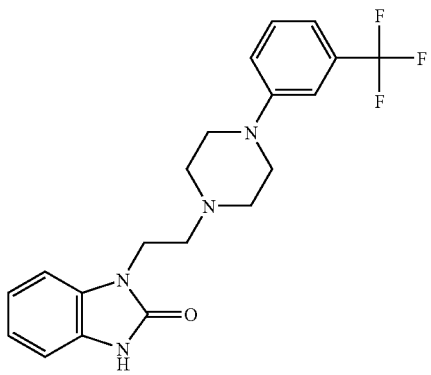 [SMILES: O=c1[nH]c2ccccc2n1CCN1CCN(c2cccc(C(F)(F)F)c2)CC1]

Flibanserin is a known post-synaptic full serotonin (5-HT$_{1A}$) agonist and 5-HT$_{2A}$ antagonist. It is therefore a promising therapeutic agent for the treatment of a variety of diseases, for instance depression, schizophrenia, and anxiety. Immediate release tablets containing flibanserin (e.g. as described in WO 03/097058) are well tolerated, but patient compliance would be much improved if a once-daily regimen were possible and if side effects could further be reduced. Such a pharmaceutical release system of flibanserin would have not only the advantage of a higher patient compliance but would also be advantageous in having a reduced potential to cause undesirable side effects by reducing the average maximum flibanserin plasma concentration $C_{max}$.

In acidic environment compounds such as flibanserin are usually very well water soluble whereas in neutral or basic environment these drugs can be practically insoluble. For example, flibanserin shows a solubility of 6.2 mg/ml in 0.1 N HCl and a solubility of 0.002 mg/ml in 0.05 M phosphate buffer pH 6.8. These physicochemical properties of basic compounds make it difficult to develop extended release dosage forms. There is a natural pH gradient from the acidity of the stomach where the pH of physiological fluids are typically around 1-2, through the weakly acidic duodenum to the virtually neutral environment of the small intestine where the pH is in the range of 5-8.

The drug release of flibanserin from conventional systems containing only pH-independent swelling polymers would be much faster in the stomach compared to the slower or even incomplete drug release in the small intestine and the colon. Formulations containing only pH-dependent retarding polymers would not allow for drug release over an extended period of time because these polymers loose their retarding effect above a certain pH. For example, Eudragit® L 100-55 forms an insoluble and impermeable film below pH 5.5, but dissolves above this pH, Carbomers form an insoluble barrier in the stomach but a more permeable gel layer in the intestine and alginic acids form an insoluble gel layer in acidic environment, but are converted to the soluble sodium alginates at a higher pH. As a result it is also difficult to find out functional excipients which would provide an improved bioavailability over the whole gastrointestinal tract for basic drugs with pH-dependent water solubility.

In prior art a number of approaches are described which provide release systems:

For example U.S. Pat. No. 4,792,452 describes a controlled release pharmaceutical formulation from which a pharmaceutical of a basic character is released at a controlled rate irrespective of the pH of the environment, consisting essentially of a pharmaceutical of a basic character, a pH-dependent polymer which is a salt of alginic acid, in an amount of from about 15 to about 45% by weight of the formulation, said salt of alginic acid having a viscosity of within the range from about 4 to about 500 centipoises in 1% solution at 25° C.; a pH-independent hydrocolloid gelling agent having a viscosity within the range of from about 50 to about 100,000 centipoises in 2% solution at 20° C., in an amount within the range of from about 3 to about 35% by weight of the formulation, and binder, whereby said formulation being free of calcium ion. The drug used is preferably a calcium channel blocker such as verapamil usually formulated in form of its hydrochloride.

As already explained after oral administration the alginates present in the controlled release pharmaceutical formulation are converted to alginic acid in the stomach and form an insoluble gel layer around the tablet particularly in the presence of calcium ions. Therefore, calcium ions are expressly excluded, which provides a very limited usability of the proposed formulation.

Furthermore, U.S. Pat. No. 4,968,508 is directed to a sustained release matrix formulation in tablet unit dosage form comprising from about 0.1% by weight to about 90% by weight of cefaclor, from about 5% by weight to about 29% by weight of a hydrophilic polymer, and from about 0.5% by weight to about 25% by weight of an acrylic polymer which dissolves at a pH in the range of about 5.0 to about 7.4, with the proviso that the total weight of the hydrophilic polymer and said acrylic polymer is less than 30% by weight of the formulation. The active substance is an antimicrobial agent, namely cefaclor, i.e. the proposed formulation is especially designed for zwitterions having both an acidic and a basic functional group having very specific requirements.

It is therefore an object of the present invention to provide improved pharmaceutical release systems which avoid the disadvantages of the prior art, and allow to provide a pH-independent release profile in order to improve the bioavailability of flibanserin and which exhibit the desirable pharmacokinetic profiles (e.g. by allowing once-daily dosing regimen and/or reducing side effects). Furthermore a method of manufacturing the same shall be provided.

DESCRIPTION OF THE INVENTION

The present invention relates to pharmaceutical release systems, preferably for oral administration, that are suitable for administration once per day, providing reduced maximum plasma concentrations compared to an immediate release formulation while still maintaining a therapeutically appropriate exposure of the active ingredient.

Surprisingly it has been found that a pharmaceutical release system comprising a therapeutically effective amount of flibanserin and at least one pharmaceutically acceptable excipient, characterized in that said pharmaceutical release system exhibits a pharmacokinetic profile that is characterized by an average maximum flibanserin plasma concentration $C_{max}$ lower than 300 ng/mL after administration of a single dose to healthy volunteers in fasted state or directly after a meal, allows a once-daily dosing regimen and reduces side effects.

Therefore, the present invention provides pharmaceutical release systems, preferably orally deliverable, comprising an therapeutically effective amount of flibanserin and at least one pharmaceutically acceptable excipient, characterized in that said pharmaceutical release systems exhibit a pharmacokinetic profile that is characterized by an average maximum flibanserin plasma concentration $C_{max}$ lower than 300 ng/mL, preferably lower than 200 ng/mL after administration of a single dose to healthy volunteers in fasted state or directly after a meal.

In another embodiment, the present invention provides pharmaceutical release systems, preferably orally deliverable, comprising a therapeutically effective amount of flibanserin and at least one pharmaceutically acceptable excipient, characterized in that said pharmaceutical release systems exhibit a pharmacokinetic profile that is characterized by an average maximum flibanserin plasma concentration $C_{max}$ lower than 300 ng/mL, preferably lower than 200 ng/mL and an average total systemic exposure between 500 and 5000 ng·h/mL after administration of a single dose to healthy volunteers in fasted state or directly after a meal.

In another embodiment, the present invention provides pharmaceutical release systems, preferably orally deliverable, comprising a therapeutically effective amount of flibanserin and at least one pharmaceutically acceptable excipient, characterized in that said pharmaceutical release systems exhibit a pharmacokinetic profile that is characterized by an average maximum flibanserin plasma concentration $C_{max}$ lower than 300 ng/mL, preferably lower than 200 ng/mL and an average total systemic exposure between 1300 and 3000 ng·h/mL after administration of a single dose to healthy volunteers in fasted state or directly after a meal.

In another embodiment, the present invention provides pharmaceutical release systems, preferably orally deliverable, comprising a therapeutically effective amount of flibanserin and at least one pharmaceutically acceptable excipient, characterized in that said pharmaceutical release systems exhibit a pharmacokinetic profile that is characterized by an average maximum flibanserin plasma concentration $C_{max}$ lower than 300 ng/mL, preferably lower than 200 ng/mL and an average total systemic exposure between 1500 and 2500 ng·h/mL after administration of a single dose to healthy volunteers in fasted state or directly after a meal.

Still further, the release formulations of the invention are characterized by having an in vitro dissolution profile (example 3) such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3.

In a preferred embodiment, the release formulations of the invention are characterized by having an in vitro dissolution profile such that at least 1% w/w and no more than 50% w/w of the flibanserin is released at 1 hour; at least 5% w/w and up to 60% w/w of the flibanserin is released at 4 hours; at least 35% w/w and up to 95% w/w of the flibanserin is released at 12 hours, when dissolution is measured as described in the last paragraph.

The pharmacokinetic and dissolution profiles given above expressly include all the numerical values, both whole numbers and fractions, within the range specified.

Pharmaceutical formulations being in conformance with the above mentioned in vitro dissolution profiles provide pharmacokinetic profiles according to the present invention.

Accordingly, the present invention provides pharmaceutical release systems, preferably orally deliverable, comprising a therapeutically effective amount of flibanserin and at least one pharmaceutically acceptable excipient, characterized by having an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3.

Furthermore, the present invention provides pharmaceutical release systems, preferably orally deliverable, comprising a therapeutically effective amount of flibanserin and at least one pharmaceutically acceptable excipient, characterized by having an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3 and characterized in that said pharmaceutical release systems exhibit a pharmacokinetic profile that is characterized by an average maximum flibanserin plasma concentration $C_{max}$ lower than 300 ng/mL, preferably lower than 200 ng/mL after administration of a single dose to healthy volunteers in fasted state or directly after a meal.

Furthermore, the present invention provides pharmaceutical release systems, preferably orally deliverable, comprising a therapeutically effective amount of flibanserin and at least one pharmaceutically acceptable excipient, characterized by having an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3 and characterized in that said pharmaceutical release systems exhibit a pharmacokinetic profile that is characterized by an average maximum flibanserin plasma concentration $C_{max}$ lower than 300 ng/mL, preferably lower than 200 ng/mL and an average total systemic exposure between 500 and 5000 ng·h/mL after administration of a single dose to healthy volunteers in fasted state or directly after a meal.

Furthermore, the present invention provides pharmaceutical release systems, preferably orally deliverable, comprising a therapeutically effective amount of flibanserin and at least one pharmaceutically acceptable excipient, characterized by having an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3 and characterized by an average maximum flibanserin plasma concentration $C_{max}$ lower than 300 ng/mL, preferably lower than 200 ng/mL and an average total systemic exposure between 1300 and 3000 ng·h/mL after administration of a single dose to healthy volunteers in fasted state or directly after a meal.

Furthermore, the present invention provides pharmaceutical release systems, preferably orally deliverable, comprising a therapeutically effective amount of flibanserin and at least one pharmaceutically acceptable excipient, characterized by having an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3 and characterized by an average maximum flibanserin plasma concentration $C_{max}$ lower than 300 ng/mL, preferably lower than 200 ng/mL and an average total systemic exposure between 1500 and 2500 ng·h/mL after administration of a single dose to healthy volunteers in fasted state or directly after a meal.

Furthermore the present invention provides for a method of treatment of a subject having a condition or disorder for which flibanserin is indicated, the method comprising administering to the subject once daily, preferably orally, one of the above and below described release systems.

Furthermore the present invention relates to the use of any of the above and below defined pharmaceutical release systems for the manufacture of a medicament for the treatment of a subject having a condition or disorder for which flibanserin is indicated.

A therapeutically effective amount or pharmaceutically effective amount of flibanserin within the meaning of the present invention is a daily dosage amount that provides therapeutic benefit in treatment of a condition or disorder for which flibanserin is indicated.

The term "average maximum flibanserin plasma concentration $C_{max}$" within the present invention is defined as geometric mean maximum plasma concentration of flibanserin calculated from individual maximum plasma concentrations as determined from plasma concentration time profiles.

The term "average total systemic exposure" within the present invention is defined as geometric mean total area under the flibanserin plasma concentration time profile ($AUC_{0-\infty}$) calculated from individual values obtained according to the following formulae:

$$AUC_{0-\infty} = AUC_{0-tz} + \frac{C'_{tz}}{\lambda_z}$$

$C'_{tz}$=predicted concentration at the time $t_z$ (last time point with a plasma concentration above the quantification limit)

$\lambda_z$=apparent terminal rate constant estimated from a regression of ln(C) versus time over the terminal log-linear drug disposition portion of the concentration-time profiles $AUC_{0-tz}$=Area under the concentration-time curve from the time point 0 until the last quantifiable drug plasma concentration as calculated by the linear up/log down method.

The particular pharmaceutical release system selected for flibanserin is not critical so long as it achieves a pharmacokinetic profile as defined herein.

Flibanserin may be administered by any route like oral, sublingual, topical or rectal. However, oral administration is preferred. Suitable pharmaceutical release system for administering flibanserin include for example patches, tablets, capsules, pills, pellets, dragees, powders, troches, suppositories and the like. Preferably, the pharmaceutical release systems of the present invention are tablets, more preferably matrix tablets, bilayer tablets and pellets.

However, as already described above, the physicochemical properties of basic compounds like flibanserin make it difficult to develop extended release dosage forms fulfilling the above described pharmacokinetic criteria as the solubility of those compounds in vivo is strongly influenced by the different pH-values in the stomach and intestine.

Surprisingly, it has been found that a specific combination of three functional excipients provides an extended release system having a pH-independent release profile for a pharmaceutical flibanserin formulation.

Therefore, the present invention provides a pharmaceutical extended release system, particularly for oral administration, of a pH-dependent water-soluble active substance, comprising or essentially consisting of
  a) a therapeutically effective amount of flibanserin or a pharmaceutically acceptable derivative thereof as active substance;
  b) one or more pharmaceutically acceptable pH-dependent polymers;
  c) one or more pharmaceutically acceptable pH-independent polymers;
  d) one or more pharmaceutically acceptable acids; and
  e) optionally one or more additives.

It is therefore provided an extended release system, particularly for oral administration, of flibanserin which guarantees largely pH-independent bioavailability of the active substance. Therefore, the extended release formulations of flibanserin of the present invention provide a pH-independent drug release behavior, particularly in the range from pH 1-5. These formulations contain organic acid(s) and a combination of pH-dependent as well as pH-independent retarding polymers as functional excipients.

The inventors of the present invention have found out that the proper combination of pH-dependent and pH-independent polymers can level out the effect of the decreasing solubility of the drug, particularly flibanserin, in the lower parts of the gastrointestinal tract while maintaining sufficiently slow release in the stomach. As a result, the difficulty to establish a suitable balance between the different parts of the gastrointestinal tract with different pH environment has been surprisingly managed.

Further, enhancement of drug release such as flibanserin in release media of elevated pH can be achieved by the addition of organic acid(s) which creates an acidic pH in the microenvironment within the extended release system and thus improves the solubility of the drug.

Accordingly, the present invention provides an pharmaceutical extended release system, characterized in that said composition exhibits a pharmacokinetic profile that is characterized by an average maximum flibanserin plasma concentration $C_{max}$ lower than 300 ng/mL, preferably lower than 200 ng/mL, after administration of a single dose to healthy volunteers in fasted state or directly after a meal; and comprises or essentially consists of
  a) a therapeutically effective amount of flibanserin or a pharmaceutically acceptable derivative thereof as active substance;
  b) one or more pharmaceutically acceptable pH-dependent polymers;

c) one or more pharmaceutically acceptable pH-independent polymers;
d) one or more pharmaceutically acceptable acids; and
e) optionally one or more additives.

Furthermore, the present invention provides an pharmaceutical extended release system, characterized in that said composition exhibits a pharmacokinetic profile that is characterized by an average maximum flibanserin plasma concentration $C_{max}$ lower than 300 ng/mL, preferably lower than 200 ng/mL, and an average total systemic exposure between 500 and 5000 ng·h/mL after administration of a single dose to healthy volunteers in fasted state or directly after a meal; and comprises or essentially consists of
  a) a therapeutically effective amount of flibanserin or a pharmaceutically acceptable derivative thereof as active substance;
  b) one or more pharmaceutically acceptable pH-dependent polymers;
  c) one or more pharmaceutically acceptable pH-independent polymers;
  d) one or more pharmaceutically acceptable acids; and
  e) optionally one or more additives.

Furthermore, the present invention provides an pharmaceutical extended release system, characterized in that said composition exhibits a pharmacokinetic profile that is characterized by an average maximum flibanserin plasma concentration $C_{max}$ lower than 300 ng/mL, preferably lower than 200 ng/mL, and an average total systemic exposure between 1300 and 3000 ng·h/mL after administration of a single dose to healthy volunteers in fasted state or directly after a meal; and comprises or essentially consists of
  a) a therapeutically effective amount of flibanserin or a pharmaceutically acceptable derivative thereof as active substance;
  b) one or more pharmaceutically acceptable pH-dependent polymers;
  c) one or more pharmaceutically acceptable pH-independent polymers;
  d) one or more pharmaceutically acceptable acids; and
  e) optionally one or more additives.

Furthermore, the present invention provides an pharmaceutical extended release system, characterized in that said composition exhibits a pharmacokinetic profile that is characterized by an average maximum flibanserin plasma concentration $C_{max}$ lower than 300 ng/mL, preferably lower than 200 ng/mL, and an average total systemic exposure between 1500 and 2500 ng·h/mL after administration of a single dose to healthy volunteers in fasted state or directly after a meal; and comprises or essentially consists of
  a) a therapeutically effective amount of flibanserin or a pharmaceutically acceptable derivative thereof as active substance;
  b) one or more pharmaceutically acceptable pH-dependent polymers;
  c) one or more pharmaceutically acceptable pH-independent polymers;
  d) one or more pharmaceutically acceptable acids; and
  e) optionally one or more additives.

Furthermore, the present invention provides an pharmaceutical extended release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; and comprises or essentially consists of
  a) a therapeutically effective amount of flibanserin or a pharmaceutically acceptable derivative thereof as active substance;
  b) one or more pharmaceutically acceptable pH-dependent polymers;
  c) one or more pharmaceutically acceptable pH-independent polymers;
  d) one or more pharmaceutically acceptable acids; and
  e) optionally one or more additives.

Furthermore, the present invention provides an pharmaceutical extended release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; a pharmacokinetic profile that is characterized; by an average maximum flibanserin plasma concentration $C_{max}$ lower than 300 ng/mL, preferably lower than 200 ng/mL; and comprises or essentially consists of
  a) a therapeutically effective amount of flibanserin or a pharmaceutically acceptable derivative thereof as active substance;
  b) one or more pharmaceutically acceptable pH-dependent polymers;
  c) one or more pharmaceutically acceptable pH-independent polymers;
  d) one or more pharmaceutically acceptable acids; and
  e) optionally one or more additives.

Furthermore, the present invention provides an pharmaceutical extended release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; a pharmacokinetic profile that is characterized; by an average maximum flibanserin plasma concentration $C_{max}$ lower than 300 ng/mL, preferably lower than 200 ng/mL, and an average total systemic exposure between 500 and 5000 ng·h/mL after administration of a single dose to healthy volunteers in fasted state or directly after a meal; and comprises or essentially consists of
  a) a therapeutically effective amount of flibanserin or a pharmaceutically acceptable derivative thereof as active substance;
  b) one or more pharmaceutically acceptable pH-dependent polymers;
  c) one or more pharmaceutically acceptable pH-independent polymers;
  d) one or more pharmaceutically acceptable acids; and
  e) optionally one or more additives.

Furthermore, the present invention provides an pharmaceutical extended release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; a pharmacokinetic profile that is characterized; by an average maximum flibanserin plasma concentration $C_{max}$ lower than 300 ng/mL, preferably lower than 200 ng/mL, and an average total systemic exposure between 1300 and 3000 ng·h/mL after administration of a single dose to healthy volunteers in fasted state or directly after a meal; and comprises or essentially consists of
   a) a therapeutically effective amount of flibanserin or a pharmaceutically acceptable derivative thereof as active substance;
   b) one or more pharmaceutically acceptable pH-dependent polymers;
   c) one or more pharmaceutically acceptable pH-independent polymers;
   d) one or more pharmaceutically acceptable acids; and
   e) optionally one or more additives.

Furthermore, the present invention provides an pharmaceutical extended release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; a pharmacokinetic profile that is characterized; by an average maximum flibanserin plasma concentration $C_{max}$ lower than 300 ng/mL, preferably lower than 200 ng/mL, and an average total systemic exposure 1500 and 2500 ng·h/mL after administration of a single dose to healthy volunteers in fasted state or directly after a meal; and comprises or essentially consists of
   a) a therapeutically effective amount of flibanserin or a pharmaceutically acceptable derivative thereof as active substance;
   b) one or more pharmaceutically acceptable pH-dependent polymers;
   c) one or more pharmaceutically acceptable pH-independent polymers;
   d) one or more pharmaceutically acceptable acids; and
   e) optionally one or more additives.

The term "system" as used for the expression "extended release system" having said three functional excipients as described above should be understood in its broadest meaning comprising any type of formulation, preparation or pharmaceutical dosage form, which is particularly suitable for oral administration. The extended release system may be in form of a pellet, tablet, matrix tablet, bilayer tablet or mini tablet. The system may be administered directly, e.g. in form of a tablet, or may be filled in another dosage form such as a capsule. The extended release system according to the present invention is preferably provided in form of a tablet or a bilayer tablet.

In the context of the present invention the term "extended release" should be understood in contrast to "immediate release". The active ingredient is gradually, continuously liberated over time, sometimes slower or faster, but virtually independent from the pH value. In particular, the term indicates that the system does not release the full dose of the active ingredient immediately after oral dosing and that the formulation allows a reduction in dosing frequency.

In the following the extended release systems of the present invention are described in more detail.

The organic acids of the extended release systems are not limited according to the frame of the present invention but any acid usable in pharmaceuticals may be employed. The organic acid is not necessarily used in the form of a solid or mixture of solids but it may be employed in form of a liquid or mixtures of liquids, for example, by firstly adhering or coating the organic acid onto a carrier or carrier particles. For instance, the adhering or coating can be carried out by a conventional coating method which is usually used in the manufacturing of pharmaceutical preparations, such as fluidized bed coating, pan coating, or the like. The inert carrier may include particles of a carrier substance, such as sucrose, lactose, starches, crystalline cellulose, colloidal silicon dioxide, and the like.

The pharmaceutically acceptable organic acids may be preferably selected from the group consisting of acetic acid, adipic acid, ascorbic acid, arginine, asparagines, aspartic acid, benzenesulphonic acid (besylate), benzoic acid, p-bromophenylsulphonic acid, camphorsulphonic acid, carbonic acid, gamma-carboxyglutamic acid, citric acid, cysteine, ethanesulphonic acid, fumaric acid, particularly cis-fumaric acid and/or trans-fumaric acid, gluconic acid, glutamic acid, glutaric acid, l-glutamine, hydrobromic acid, hydrochloric acid, hydroiodic acid, isethionic acid, isoleucine, lactic acid, l-leucine, lysine, maleic acid, malic acid, malonic acid, mandelic acid, methanesulphonic acid (mesylate), methionine, mucinic acid, nitric acid, omithine, oxalic acid, pamoic acid, pantothenic acid, phosphoric acid, serine, succinic acid, sulphuric acid, tartaric acid, p-toluenesulphonic acid, tyrosine glutamic acid, valine and derivatives and mixtures thereof. The above listing is not intended to be of limitative character, the skilled person is familiar with further examples. Particularly preferred are adipic acid, ascorbic acid, aspartic acid, citric acid, fumaric acid, lactic acid, malic acid, succinic acid and tartaric acid, preferably succinic acid, tartaric acid and fumaric acid.

The organic acid(s) is (are) preferably present in an amount of 0.25-40% by weight, more preferably 0.5-35% by weight, most preferably 1-30% by weight, particularly 5-30% by weight.

It should be noted that the ranges of values given herein expressly include all the numerical values, both whole numbers and fractions, within the ranges as specified.

The pH-independent polymer of the extended release systems is not limited according to the present invention; it may be used any pharmaceutically acceptable polymer which has a solubility characteristic being independent from the pH value of the environment.

The one or more pH-independent polymers of the present invention comprise alkylcelluloses, such as, methylcellulose, ethylcelluloses; hydroxyalkyl celluloses, for example, hydroxymethyl cellulose, hydroxyethyl cellulose, hydroxypropyl cellulose and hydroxybutyl cellulose; hydroxyalkyl alkylcelluloses, such as hydroxyethyl methylcellulose and hydroxypropyl methylcellulose; carboxyalkylcellulose esters; other natural, semi-synthetic, or synthetic di-, oligo- and polysaccharides such as galactomannans, tragacanth, agar, guar gum, and polyfructans; ammonio methacrylate copolymers; polyvinylalcohol; polyvinylpyrrolidone, copolymers of polyvinylpyrrolidone with vinyl acetate; combinations of polyvinylalcohol and polyvinylpyrrolidone; polyalkylene oxides such as polyethylene oxide and polypropylene oxide; copolymers of ethylene oxide and propylene oxide as well as derivatives and mixtures thereof; preferably cellulose ether derivatives such as hydroxypropyl methylcellulose and hydroxypropyl cellulose, most preferred hydroxypropyl methylcellulose, for example Methocel ethers.

The term "derivatives" according to the present invention is meant to include any compound derived from the mentioned compounds as basic system, for example by substitution with one or more functional groups. This belongs to the general knowledge of the skilled person.

The pH-independent polymer may be used alone or in combination of two or more pH-independent polymers. The pH-independent polymer(s) may be present in an amount of 0.5-75% by weight, preferably 1-70% by weight, more preferably 2-65% by weight, particularly 5-50% by weight and most preferably 15-30% by weight.

Also the pH-dependent polymer of the extended release systems is not limited according to the present invention. Any pharmaceutically acceptable polymer may be used which has a pH-dependent solubility, preferably a polymer which has a high solubility in high pH medium and a low solubility in low pH medium in the sense that the solubility of the polymer is preferably better in high pH medium (pH about more than 4) compared with low pH medium (pH about 1-2).

The pH-dependent polymer(s) of the present invention comprises acrylic acid polymerisate, methacrylic acid copolymers, alginates, carrageenans, acacia, xanthan gum, chitin derivates such as chitosan, carmellose sodium, carmellose calcium, phthalate such as hydroxypropyl methyl cellulose phthalate, cellulose acetate phthalate, polyvinyl acetate phthalate, trimellitate such as cellulose acetate trimellitate, shellac and derivatives and mixtures thereof, preferably methacrylic acid copolymers such as poly(methacrylic acid, ethylacrylate) 1:1 (Eudragit® L 100-55), poly(methacrylic acid, methyl methacrylate) 1:1 (Eudragit® L 100), poly(methacrylic acid, methyl methacrylate) 1:2 (Eudragit® S), and alginates (such as Protanal®), most preferably used are Eudragit® L and Protanal®.

The pH-dependent polymer may be used alone or in combination of two or more pH-dependent polymers. The pH-dependent polymer(s) may be present in an amount of 0.25-25% by weight, more preferably 1-20% by weight, most preferably 2-15% by weight, particularly 3-10% by weight.

The term "one or more" or "at least one" as used in the present invention stands for 1, 2, 3, 4, 5, 6, 7, 8, 9, 10 compounds or even more. Preferred embodiments comprise 1, 2, or 3 such compounds. More preferred embodiments comprise 1 or 2 such compounds and even more preferred are embodiments comprising one of such compounds.

The pharmaceutically active substance which is contained in the extended release system of the present invention is flibanserin. Flibanserin can be used in form of the free base, or in form of any known pharmacologically acceptable derivative thereof such as its pharmaceutically acceptable acid addition salts and/or optionally in form of the hydrates and/or solvates thereof. Suitable acid addition salts include for example those of the acids selected from succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularly the hydrochloride, are preferred.

If flibanserin is used in form of the free base, it is preferably used in form of flibanserin polymorph A which represents the free base of flibanserin in a specific polymorphic form. Polymorph A and a process for its preparation are disclosed in WO 03/014079 A1, the whole disclosure thereof being incorporated by reference into the present specification.

Flibanserin is contained in an amount suitable for exhibiting the desired pharmacological activities of each medicament, which are known and varies in accordance with the type of medication. Flibanserin is preferably present in a pharmaceutically effective amount (0.01 mg to 200 mg, preferably from 0.1 to 100 mg or 0.1 to 50 mg), which, however, may depend from a number of factors for example the age and body weight of the patient, and the nature and stage of the disease. This is deemed to be within the capabilities of the skilled man, and the existing literature on the components can be consulted in order to arrive at the optimum dose. The dosis range applicable per day is between 0.1 to 400, preferably between 1.0 to 300, more preferably between 2 to 200 mg.

The pharmaceutical release systems of the present invention are administered to the patient preferably once daily. However, if necessary the formulations of the invention may be administered either two or more times daily consecutively over a period of time.

For example, the dose can be administered to a patient in the morning and the evening, more preferably once in the morning (25 or 50 mg of flibanserin) and once in the evening (25 or 50 mg of flibanserin), most preferably once in the evening only (50 or 100 mg of flibanserin) consecutively over a period of time.

In the extended release system of the present invention the flibanserin content is preferably in an amount of not more than 50% by weight, more preferably not more than 45% by weight, most preferably not more than 40% by weight. The range is preferably from 2.5-50% by weight, preferably from 5-45% by weight, more preferably from 10-40% by weight and most preferably from 15-30% by weight.

The doses given above expressly include all the numerical values, both whole numbers and fractions, within the range specified.

The term "conditions or disorder for which flibanserin is indicated" includes all known indications thereof, preferably in the treatment of patients suffering from central nervous system disorders, in particular in affective disorders (e.g. depression like major depressive disorder, childhood depression, dysthymia, seasonal affective disorder, dysthymic disorder and minor depressive disorder; bipolar disorders), anxiety (incl. panic disorder with or without agoraphobia, agoraphobia without history of panic disorder, specific phobia (simple phobia), social phobia (social anxiety disorder), obsessive-compulsive disorder (OCD), post-traumatic stress disorder, acute stress disorder, generalized anxiety disorder and anxiety disorder not otherwise specified), sleep and sexual disorders (e.g. Hypoactive Sexual Desire Disorder, premenstrual disorders like premenstrual dysphoria, premenstrual syndrome, premenstrual dysphoric disorder; sexual aversion disorder, sexual arousal disorder, orgasmic disorder, sexual pain disorders like dyspareunia, vaginismus, noncoital sexual pain disorder; sexual dysfunction due to a general medical condition and substance-induced sexual dysfunction), psychosis, schizophrenia (including the disorganized type, the catatonic type, the paranoid type, the undifferentiated type, the residual type of schizophrenia, schizoaffective disorder, schizophreniform disorder, delusional disorder, brief psychotic disorder, shared psychotic disorder, psychotic disorder due to a general medical condition, substance-induced psychotic disorder, and psychotic disorder not otherwise specified), personality disorders, mental organic disorders, mental disorders in childhood, aggressiveness, age associated memory impairment, for neuroprotection, the treatment and/or prevention of neurodegenerative diseases as well as cerebral ischaemia of various origins (e.g. epilepsy, hypoglycaemia, hypoxia, anoxia, brain trauma, brain oedema, amyotropic lateral sclerosis, Huntington's disease, Alzheimer's disease, hypotension, cardiac infarct, brain pressure (elevated intracranial pressure), ischaemic and haemorrhagic stroke (stroke), global cerebral ischaemia during stoppage of the heart, diabetic polyneuropathy, tinnitus, perinatal asphyxia, cardiac hypertrophia (thickening of the heart muscle) and cardiac insufficiency (weakness of the heart muscle); anorexia nervosa (incl. binge-eating/purging type of anorexia nervosa and the restricting type of anorexia nervosa), Attention Deficit Hyperactivity Disorder (ADHD) (incl. ADHD predominantly combined type, ADHD predominantly inattentive type, and ADHD predominantly hyperactive-impulsive type), obesity (incl. exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity), urinary incontinence (incl. overactive bladder syndrome, urgency, urge urinary incontinence, stress urinary incontinence, mixed urinary incontinence), chronic pain (incl. neuropathic pain, diabetic neuropathy, post-herpetic neuralgia (PHN), carpal tunnel syndrome (CTS), HIV neuropathy, phantom limb pain, complex regional pain syndrome (CPRS), trigeminal neuralgia/trigeminus neuralgia/tic douloureux, surgical intervention (e.g. post-operative analgesics), diabetic vasculopathy, capillary resistance or diabetic symptoms associated with insulitis, pain associated with angina, pain associated with menstruation, pain associated with cancer, dental pain, headache, migraine, trigeminal neuralgia, temporomandibular joint syndrome, myofascial pain muscular injury, fibromyalgia syndrome, bone and joint pain (osteoarthritis), rheumatoid arthritis, rheumatoid arthritis and edema resulting from trauma associated with burns, sprains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain and geriatric pain), Valvular Heart Disease (incl. valvular stenosis, valvular regurgitation, atresia of one of the valves, mitral valve prolapse), preferably Hypoactive Sexual Desire Disorder (HSDD).

The selection of polymers for the extended release systems of the present invention, at least one pH-dependent and at least one pH-independent, have an influence on the release of the flibanserin in order to establish the desired release profiles. Although the active substance present has a pH-dependent solubility the release profile of the extended release system according to the present invention is almost independent from the pH value resulting in an improved bioavailability. In fact, the combination of different retarding polymers and the addition of organic acid(s) lead to a widely pH-independent drug release (in the range of pH 1-5) of the pH-dependent water soluble flibanserin.

Therefore, the aforementioned extended release system of the present invention comprises or essentially consists of flibanserin, pH-dependent and pH-independent retarding polymers, organic acid(s), optionally in combination with additives suitable in pharmaceutical formulations such as excipients, carriers, technological adjuvants and the like. Preferred additives are for example fillers, lubricants, glidants, solubilizers, dyes, binders and the like.

According to a preferred embodiment the extended release system of the present invention consists of

| | |
|---|---|
| flibanserin or a pharmaceutically acceptable derivative thereof | 5-50% by weight |
| pH-dependent polymer(s) | 0.25-25% by weight |
| pH-independent polymer(s) | 0.5-75% by weight |
| organic acid(s) | 0.25-40% by weight |
| lubricant(s) | 0.1-4% by weight |
| additional additives | ad 100% by weight |

According to a more preferred embodiment the extended release system of the present invention consists of

| | |
|---|---|
| flibanserin or a pharmaceutically acceptable derivative thereof | 5-50% by weight |
| pH-dependent polymer(s) | 1-20% by weight |
| pH-independent polymer(s) | 1-70% by weight |
| organic acid(s) | 0.5-35% by weight |
| lubricant(s) | 0.2-3.5% by weight |
| additional additives | ad 100% by weight |

According to an even more preferred embodiment the extended release system of the present invention consists of

| | |
|---|---|
| flibanserin or a pharmaceutically acceptable derivative thereof | 5-50% by weight |
| pH-dependent polymer(s) | 2-15% by weight |
| pH-independent polymer(s) | 2-65% by weight |
| organic acid(s) | 1-30% by weight |
| lubricant(s) | 0.25-3% by weight |
| additional additives | ad 100% by weight |

According to an even more preferred embodiment the extended release system of the present invention consists of

| | |
|---|---|
| flibanserin or a pharmaceutically acceptable derivative thereof | 5-50% by weight |
| pH-dependent polymer(s) | 3-10% by weight |
| pH-independent polymer(s) | 5-50% by weight |
| organic acid(s) | 5-30% by weight |
| lubricant(s) | 1-3% by weight |
| additional additives | ad 100% by weight |

According to a particularly preferred embodiment the extended release system of the present invention consists of

| | |
|---|---|
| flibanserin or a pharmaceutically acceptable derivative thereof | 5-50% by weight |
| pH-dependent polymer(s) | 3-10% by weight |
| pH-independent polymer(s) | 15-30% by weight |
| organic acid(s) | 5-30% by weight |
| lubricant(s) | 1-3% by weight |
| additional additives | ad 100% by weight |

Unless otherwise stated, percentages specified are always percent by weight.

Therefore, additives e.g. excipients, carriers, technological adjuvants may be present in the extended release systems such as lubricants, glidants, granulating agents, anti-caking agents, agglomeration inhibitors, antiadherents, anti-tacking agent, anti-sticking agent, flavors, aromatiziers, dyes or colorants, preservatives, plastizers, wetting agents, sweeteners, chelating agents, stabilizers, solubilizers, antioxidants, fillers, diluents and the like. These pharmaceutically acceptable formulating agents are e.g. present in order to promote the manufacture, compressibility, appearance and/or taste of the preparation. Other conventional additives known in the art can also be included. The above listing is not intended to be of limitative character, the skilled person is familiar with further examples.

A lubricant or agglomeration inhibitor can be used to enhance release of the dosage form from the apparatus on which it is formed, for example by preventing adherence to the surface of an upper punch ("picking") or lower punch ("sticking"). These materials may also possess antiadherent or glidant properties. Preferable lubricants are for example stearic acid as well as salts thereof including sodium stearate, calcium stearate, zinc stearate, magnesium stearate, glyceryl monostearate, particularly magnesium stearate, polyethylene glycols (all types at different molecular weights of PEGs), fumaric acid, glycerides such as glyceryl behenate (Compritol® 888), Dynasan® 118 or Boeson® VP.

An anti-tacking agent, anti-sticking agent or glidant or an agent to improve flowability can be used to improve powder flow properties prior to and during the manufacturing process and to reduce caking. Among this group of excipients may be exemplarily mentioned silicon dioxide, particularly colloidal silicon dioxide (e.g. Aerosil®, Cab-O-Sil®), stearic acid as well as salts thereof including sodium stearate, calcium stearate, zinc stearate, magnesium stearate, magnesium silicate, calcium silicate, magnesium trisilicate and talc. Preferably glidants are colloidal silicon dioxide and talc.

As binder, it is possible to use any binder usually employed in pharmaceuticals. Exemplarily mentioned are naturally occurring or partially or totally synthetic polymers selected from acacia, agar, alginic acid, carbomers, carmellose sodium, carrageenan, cellulose acetate phthalate, ceratonia, chitosan, confectionar's sugar, copovidone, povidone, cottonseed oil, dextrate, dextrin, dextrose, polydextrose, maltodextrin, maltose, cellulose and derivatives thereof such as microcrystalline cellulose, methylcellulose, ethylcellulose, hydroxyethyl cellulose, hydroxyethyl methylcellulose, hydroxypropyl celluloses, carboxymethylcelluloses, hypromelloses (cellulose hydroxypropyl methyl ether), starch and derivatives thereof, such as pregelatinized starch, hydroxypropylstarch, corn starch, gelatin, glyceryl behenate, tragacanth, guar gum, hydrogenated vegetable oils, inulin, lactose, glucose, magnesium aluminium silicate, poloxamer, polycarbophils, polyethylene oxide, polyvinylpyrrolidone, copolymers of N-vinylpyrrolidone and vinyl acetate, polymethacrylates, polyethylene glycols, alginates such as sodium alginate, gelatin, sucrose, sunflower oil, zein as well as derivatives and mixtures thereof.

Particularly preferred binders are acacia, hydroxypropyl celluloses, hydroxypropyl methylcelluloses, methylcelluloses, hydroxyethyl celluloses, carboxymethylcelluloses, polyvinylpyrrolidone, the copolymers of N-vinylpyrrolidone and vinyl acetate, or combinations of these polymers. The above listing is not intended to be of limitative character, the skilled person is familiar with further examples.

As further additives which may be present the following non limitative groups are given
- preservatives, preferably antimicrobial preservatives such as benzalkonium chloride, benzoic acid, methyl parahydroxybenzoate, propyl parahydroxybenzoate, sodium benzoate and sorbic acid;
- sweetening agents such as acesulfame potassium, alitame, aspartame, compressible sugar, confectioner's sugar, dextrose, erythritol, fructose, glycerin, inulin, isomalt, lactitol, liquid glucose, maltitol, maltitol solution, maltose, mannitol, neospheridin dihydrochalcone, polydextrose, saccharin, saccharin sodium, sodium cyclamate, sorbitol, sucralose, sucrose, thaumatin, trehalose, xylitol;
- solubilizers such as benzalkonium chloride, benzethonium chloride, benzyl alcohol, benzyl benzoate, cetylpyridinium chloride, cyclodextrins, lecithin, meglumine, poloxamers, polyethylene alkyl ethers, polyoxyethylene alkyl ethers, polyoxyethylene castor oil derivatives, polyoxyethylen sorbitan fatty acid esters, polyoxyethylene stearates, povidone, 2-pyrrolidone, sodium bicarbonate, sorbitan esters, stearic acid, sulfobutylether β-cyclodextrin, sodium dodecyl sulphate (SDS) and vitamin E-TPGS;
- separating agents such as e.g. talc, magnesium stearate or silicic acid serves to prevent the particles from aggregating during the manufacturing process; and
- plasticizers are preferably not present in the extended release system which is usually free of plasticizer; however in some rare cases the plasticizers may be selected from e.g. citrates such as acetyltributyl citrate, acetyltriethyl citrate, tributyl citrate, triethyl citrate, benzyl benzoate, castor oil, phthalates such as cellulose acetate phthalate, dibutyl phthalate, diethyl phthalate, dimethyl phthalate, hypromellose phthalate, polyvinyl acetate phthalate, dimeticon, fractionated coconut oil, chlorbutanol, dextrin, sebacate such as dibutyl sebacate, glycerin, glycerin derivatives such as glycerol monostearate, glycerol triacetate (triacetin), acetylated monoglyceride, mannitol, mineral oil, lanolin alcohols, palimitic acid, 2-pyrrolidone, sorbitol, stearic acid, triethanolamin, polyethyleneglycols (all types at different molecular weights of PEGs), and propylene glycol, and derivatives and mixtures thereof,
- pigments which are especially useful are titanium dioxide, indigo carmine, iron oxide pigments such as iron oxides red and yellow, and some of the aluminium lakes as well as pigment black, pigment white, pigment yellow, sunset yellow, sunset yellow lake, quinoline yellow lake and the like.

The extended release systems of the present inventions additionally comprise one or more excipient(s) with diluting or filling properties (fillers or diluents). Fillers or diluents are inert compounds designed to make up the required bulk of the dosage form when the drug dosage itself is inadequate to produce this bulk.

Suitable fillers or diluents may be selected from, for example, lactose, in particular lactose monohydrate, talc, starches and derivatives such as pregelatinized starch, corn starch, wheat starch, rice starch, potato starch, sterilizable maize, sodium chloride, calcium carbonate, calcium phosphate, particularly dibasic calcium phosphate, calcium sulphate, dicalcium or tricalcium phosphate, magnesium carbonate, magnesium oxide, cellulose and derivatives, such as powdered cellulose, microcrystalline or silicified microcrystalline cellulose, cellulose acetate, sugars and derivatives such as confectioner's sugar, fructose, sucrose, dextrates, dextrin, D-sorbitol sulfobutylether β-cyclodextrin, dextrose, polydextrose, trehalose, maltose, maltitol, mannitol, maltodextrin, sorbitol, inulin, xylitol, erythritol, isomalt, kaolin and lactitol.

Possible chelating agents which may be added are edetic acid, dipotassium edetate, disodium edetate, edetate calcium disoidium, trisodium edetate, maltol and the like.

It is a matter of course that an additive may have more than one functionality so that they may be categorized among more than one type of additive. For example corn starch or pregelatinized starch may impart several functions at the same time such as swelling polymer, filler, glidant, and the like. However, the skilled person knows the several functions and is able to select the additive according to the intended use thereof.

The resulting extended release system may finally be coated with a coating preferably of a pharmaceutically conventional film forming agent, and optionally additives. This may be done by conventional methods. Coating serves to mask the taste of the drug, make e.g. a tablet easier to swallow, to reduce any increased abrasion during packing, e.g. into capsules, to increase the shelf life and/or as further diffusion barrier, in some cases, it may improve the appearance of the dosage form.

The extended release system can be sugar coated according to procedures well known in the art, or can be coated with any one of numerous polymeric film-forming agents frequently employed by formulation chemists. Suitable film-forming agents include for example ammonium alginate, chitosan, chlorpheniramine maleate, copovidone, phthalate such as dibutyl phthalate, diethyl phthalate, dimethyl phthalate, cellulose acetate phthalate, polyvinyl acetate phthalate, dibutyl sebacate, ethyl lactate, alkylcelluloses and derivatives thereof such as ethylcelluloses, methylcelluloses, gelatin, hydroxyalkyl celluloses and derivatives thereof such as hydroxyethyl cellulose, hydroxypropyl cellulose, hydroxyalkyl alkylcellulose and derivatives thereof such as hypromelloses (hydroxypropyl methylcellulose), hydroxypropyl methylcellulose acetate succinate, hydroxypropyl methylcellulose phthalate, cellulose acetate trimellitate, cellulose acetate phthalate, maltodextrin, calcium carbonate, polydextrose, polyethylene glycols (all types at different molecular weigths of PEGs), polyethylene oxide, polymers and copolymers of acrylic and methacrylic acid and the esters thereof, or combinations of these polymers such as polymethacrylates, poly(methylvinyl ether/maleic anhydride), polyvinyl acetate phthalate, triethyl citrate, vanillin, shellac as well as derivatives and mixtures thereof.

Particularly preferred film-forming agents are hydroxypropyl cellulose, hydroxypropyl methylcellulose, methylcelluloses, polymers and copolymers of acrylic and methacrylic acid and the esters thereof, or combinations of these polymers. Preferably polymers are poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); hydroxypropyl methylcellulose acetate succinate, hydroxypropyl methylcellulose phthalate, cellulose acetate trimellitate, cellulose acetate phthalate (Aquacoate® CPD), polyvinyl acetate phthalate (Sureteric®), and shellac.

Further suitable additives, excipients, diluents, carriers, technological adjuvants, if desired, may be present.

The present extended release system of the present invention may be prepared by methods which are well known to those skilled in the art, for example wet granulation, direct compression or roller compaction process can be applied to the manufacturing of the extended release system. The roller compaction process is particularly preferred.

The pH-dependent polymer employed in the present extended release system may be incorporated into the formulation at different stages in the process. The pH-independent polymer may be added, for example in form of a finely divided powder, to the active substance and a part or all of the pH-dependent polymer along with suitable excipients or additives as desired. Then, the ingredients may be thoroughly mixed to obtain a pre-mixture which is subsequently subjected to a compacting in a suitable apparatus. Thereafter further powdery additives may be added and sieved to obtain a final mixture from which e.g. a tablet may be pressed.

Alternatively, all or a part of the pH-dependent polymer may also be added after the pre-mixture has been obtained and/or after compaction have been completed. The skilled person is readily able to produce a formulation without undue burden.

It is also possible to have a bilayer tablet with one immediate release layer and one extended release layer of Flibanserin.

Thus, subject of the present invention is an oral to take pharmaceutical extended release system, in particular tablets, like tablets for swallowing, bilayer tablets, sugar-coated tablets, coated tablets, chewable tablets, matrix tablets, pills or capsules. Among these tablets are most preferred according to the present invention. Among the latter coated tablets and/or swallowable tablets are preferred.

The extended release system of the present invention can be of any suitable size and shape, for example round, oval, polygonal or pillow-shaped, and optionally bear non-functional surface markings.

If the extended release system which is subject of the present invention is a tablet, preferably it shall have a round or oval shape. The size thereof preferably shall be between 5 mm and 12 mm diameter in case of round shape and between 6×12 mm and 10×20 mm in case of oval shape. The weight thereof preferably shall be between 50 and 1000 mg.

If the extended release system which is subject of the present invention is a capsule, preferably it shall be of the capsule size of between 5 and 0. The capsule then comprises the pharmaceutical extended releases system in form of granules which correspond in their chemical and physical composition to the core of the tablet but which are smaller in size.

The extended release system may be packed in bottles or blisters well known in the art. Among such blisters are such being made of polyvinylchloride or polyvinylidene chloride. Aluminum-blisters are also possible. Bottles may be made of poylpropylene or polyethylene for example. Optionally desiccants like silica gel or molecular sieves can be used in the bottles. Other conventional packaging materials are possible, too.

The extended release systems of the invention can be packaged in a container, accompanied by a package insert providing pertinent information such as, for example, dosage and administration information, contraindications, precautions, drug interactions and adverse reactions.

The advantages of the extended release systems of the present invention are manifold:

The extended release system according to the present invention is able to suppress the immediate dissolution and release of the active substance in acidic environment whereas the continuous release of the active substance in intestinal fluids can be reliably achieved. The desired blood level of the active substance can be realized for a long period of time resulting in a reduced potential to cause undesirable side effects.

The extended release system of the present invention remains sufficiently stable when stored. Only after the administration of the formulation system does the pH modifier dissolve and produce a micro climate in which the active substance can dissolve.

According to the present invention it is provided a virtually pH-independent release for the active substance flibanserin which is a weak base and which in the range from pH 1 to pH 7.5 would exhibit pH-dependent solubility characteristics. That is flibanserin usually has greater solubility under acidic conditions and lesser solubility under neutral and basic conditions. As a result the present invention provides a change of the release characteristics of flibanserin resulting in a significantly improved bioavailability which is independent on the pH in the gastrointestinal tract when administered orally.

Not only extended release systems as described above but also with pharmaceutical controlled release systems as described below may a pharmacokinetic profile as defined in accordance with the present invention be achieved.

As a further example according to the invention a specific build-up of a controlled release system makes it possible to readily control and adjust the desired release profile, the formulation principles allow a release profile which is independent from the pH value.

Therefore, the present invention provides a pharmaceutical controlled release system for administration, particularly oral administration, of flibanserin, comprising
  a) a core material containing or consisting of one or more pharmaceutically acceptable pH modifiers;
  b) optionally an insulating layer,
  c) a first layer, particularly for protection of the layer(s) beneath and/or for further controlling of the release of the pH-modifier, containing or consisting of one or more pharmaceutically acceptable water-insoluble polymers;
  d) a second layer containing or consisting of flibanserin;
  e) a third layer, which preferably represents a further controlled release layer, containing or consisting of one or more pharmaceutically acceptable polymers having anionic or no ionic groups; and
  f) optionally a fourth layer, for example in form of a secondary controlled release outer coating, preferably for controlling release in the stomach or a non-functional coating.

Accordingly, the present invention provides an pharmaceutical controlled release system, characterized in that said composition exhibits a pharmacokinetic profile that is characterized by an average maximum flibanserin plasma concentration $C_{max}$ lower than 300 ng/mL, preferably lower than 200 ng/mL, after administration of a single dose to healthy volunteers in fasted state or directly after a meal; and comprises or essentially consists of
  a) a core material containing or consisting of one or more pharmaceutically acceptable pH modifiers;
  b) optionally an insulating layer,
  c) a first layer, particularly for protection of the layer(s) beneath and/or for further controlling of the release of the pH-modifier, containing or consisting of one or more pharmaceutically acceptable water-insoluble polymers;
  d) a second layer containing or consisting of flibanserin;
  e) a third layer, which preferably represents a further controlled release layer, containing or consisting of one or more pharmaceutically acceptable polymers having anionic or no ionic groups; and
  f) optionally a fourth layer, for example in form of a secondary controlled release outer coating, preferably for controlling release in the stomach or a non-functional coating.

Furthermore, the present invention provides an pharmaceutical controlled release system, characterized in that said composition exhibits a pharmacokinetic profile that is characterized by an average maximum flibanserin plasma concentration $C_{max}$ lower than 300 ng/mL, preferably lower than 200 ng/mL, and an average total systemic exposure between 500 and 5000 ng·h/mL after administration of a single dose to healthy volunteers in fasted state or directly after a meal; and comprises or essentially consists of
  a) a core material containing or consisting of one or more pharmaceutically acceptable pH modifiers;
  b) optionally an insulating layer,
  c) a first layer, particularly for protection of the layer(s) beneath and/or for further controlling of the release of the pH-modifier, containing or consisting of one or more pharmaceutically acceptable water-insoluble polymers;
  d) a second layer containing or consisting of flibanserin;
  e) a third layer, which preferably represents a further controlled release layer, containing or consisting of one or more pharmaceutically acceptable polymers having anionic or no ionic groups; and
  f) optionally a fourth layer, for example in form of a secondary controlled release outer coating, preferably for controlling release in the stomach or a non-functional coating.

Furthermore, the present invention provides an pharmaceutical controlled release system, characterized in that said composition exhibits a pharmacokinetic profile that is characterized by an average maximum flibanserin plasma concentration $C_{max}$ lower than 300 ng/mL, preferably lower than 200 ng/mL, and an average total systemic exposure between 1300 and 3000 ng·h/mL after administration of a single dose to healthy volunteers in fasted state or directly after a meal; and comprises or essentially consists of
  a) a core material containing or consisting of one or more pharmaceutically acceptable pH modifiers;
  b) optionally an insulating layer,
  c) a first layer, particularly for protection of the layer(s) beneath and/or for further controlling of the release of the pH-modifier, containing or consisting of one or more pharmaceutically acceptable water-insoluble polymers;
  d) a second layer containing or consisting of flibanserin;
  e) a third layer, which preferably represents a further controlled release layer, containing or consisting of one or more pharmaceutically acceptable polymers having anionic or no ionic groups; and
  f) optionally a fourth layer, for example in form of a secondary controlled release outer coating, preferably for controlling release in the stomach or a non-functional coating.

Furthermore, the present invention provides an pharmaceutical controlled release system, characterized in that said composition exhibits a pharmacokinetic profile that is characterized by an average maximum flibanserin plasma concentration $C_{max}$ lower than 300 ng/mL, preferably lower than 200 ng/mL, and an average total systemic exposure between 1500 and 2500 ng·h/mL after administration of a single dose to healthy volunteers in fasted state or directly after a meal; and comprises or essentially consists of
  a) a core material containing or consisting of one or more pharmaceutically acceptable pH modifiers;
  b) optionally an insulating layer,
  c) a first layer, particularly for protection of the layer(s) beneath and/or for further controlling of the release of the pH-modifier, containing or consisting of one or more pharmaceutically acceptable water-insoluble polymers;
  d) a second layer containing or consisting of flibanserin;
  e) a third layer, which preferably represents a further controlled release layer, containing or consisting of one or more pharmaceutically acceptable polymers having anionic or no ionic groups; and
  f) optionally a fourth layer, for example in form of a secondary controlled release outer coating, preferably for controlling release in the stomach or a non-functional coating.

Furthermore, the present invention provides an pharmaceutical controlled release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; and comprises or essentially consists of a) a core material containing or consisting of one or more pharmaceutically acceptable pH modifiers;
b) optionally an insulating layer,
c) a first layer, particularly for protection of the layer(s) beneath and/or for further controlling of the release of the pH-modifier, containing or consisting of one or more pharmaceutically acceptable water-insoluble polymers;
d) a second layer containing or consisting of flibanserin;
e) a third layer, which preferably represents a further controlled release layer, containing or consisting of one or more pharmaceutically acceptable polymers having anionic or no ionic groups; and
f) optionally a fourth layer, for example in form of a secondary controlled release outer coating, preferably for controlling release in the stomach or a non-functional coating.

Furthermore, the present invention provides an pharmaceutical controlled release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; a pharmacokinetic profile that is characterized; by an average maximum flibanserin plasma concentration $C_{max}$ lower than 300 ng/mL, preferably lower than 200 ng/mL; and comprises or essentially consists of
a) a core material containing or consisting of one or more pharmaceutically acceptable pH modifiers;
b) optionally an insulating layer,
c) a first layer, particularly for protection of the layer(s) beneath and/or for further controlling of the release of the pH-modifier, containing or consisting of one or more pharmaceutically acceptable water-insoluble polymers;
d) a second layer containing or consisting of flibanserin;
e) a third layer, which preferably represents a further controlled release layer, containing or consisting of one or more pharmaceutically acceptable polymers having anionic or no ionic groups; and
f) optionally a fourth layer, for example in form of a secondary controlled release outer coating, preferably for controlling release in the stomach or a non-functional coating.

Furthermore, the present invention provides an pharmaceutical controlled release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; a pharmacokinetic profile that is characterized; by an average maximum flibanserin plasma concentration $C_{max}$ lower than 300 ng/mL, preferably lower than 200 ng/mL, and an average total systemic exposure between 500 and 5000 ng·h/mL after administration of a single dose to healthy volunteers in fasted state or directly after a meal; and comprises or essentially consists of
a) a core material containing or consisting of one or more pharmaceutically acceptable pH modifiers;
b) optionally an insulating layer,
c) a first layer, particularly for protection of the layer(s) beneath and/or for further controlling of the release of the pH-modifier, containing or consisting of one or more pharmaceutically acceptable water-insoluble polymers;
d) a second layer containing or consisting of flibanserin;
e) a third layer, which preferably represents a further controlled release layer, containing or consisting of one or more pharmaceutically acceptable polymers having anionic or no ionic groups; and
f) optionally a fourth layer, for example in form of a secondary controlled release outer coating, preferably for controlling release in the stomach or a non-functional coating.

Furthermore, the present invention provides an pharmaceutical controlled release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; a pharmacokinetic profile that is characterized; by an average maximum flibanserin plasma concentration $C_{max}$ lower than 300 ng/mL, preferably lower than 200 ng/mL, and an average total systemic exposure between 1300 and 3000 ng·h/mL after administration of a single dose to healthy volunteers in fasted state or directly after a meal; and comprises or essentially consists of
a) a core material containing or consisting of one or more pharmaceutically acceptable pH modifiers;
b) optionally an insulating layer,
c) a first layer, particularly for protection of the layer(s) beneath and/or for further controlling of the release of the pH-modifier, containing or consisting of one or more pharmaceutically acceptable water-insoluble polymers;
d) a second layer containing or consisting of flibanserin;
e) a third layer, which preferably represents a further controlled release layer, containing or consisting of one or more pharmaceutically acceptable polymers having anionic or no ionic groups; and
f) optionally a fourth layer, for example in form of a secondary controlled release outer coating, preferably for controlling release in the stomach or a non-functional coating.

Furthermore, the present invention provides an pharmaceutical controlled release system, characterized in that said composition exhibits an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured as by method described in example 3; a pharmacokinetic profile that is characterized; by an average maximum flibanserin plasma concentration $C_{max}$ lower than 300 ng/mL, preferably lower than 200 ng/mL, and an average total systemic exposure 1500 and 2500 ng·h/mL after administration of a single dose to healthy volunteers in fasted state or directly after a meal; and comprises or essentially consists of
a) a core material containing or consisting of one or more pharmaceutically acceptable pH modifiers;
b) optionally an insulating layer,
c) a first layer, particularly for protection of the layer(s) beneath and/or for further controlling of the release of the pH-modifier, containing or consisting of one or more pharmaceutically acceptable water-insoluble polymers;
d) a second layer containing or consisting of flibanserin;
e) a third layer, which preferably represents a further controlled release layer, containing or consisting of one or more pharmaceutically acceptable polymers having anionic or no ionic groups; and f) optionally a fourth layer, for example in form of a secondary controlled release outer coating, preferably for controlling release in the stomach or a non-functional coating.

It is therefore provided a controlled release system, particularly for oral administration, of flibanserin which guarantees largely pH-independent bioavailability of flibanserin and which exhibit the desirable pharmacokinetic profiles (e.g. by allowing once-daily dosing regimen and/or reducing side effects).

In the frame of the present invention the term "controlled release" should be understood in contrast to an immediate release, the active ingredient is gradually, continuously liberated over time, sometimes slower or faster, but independent from the pH value. In particular, the term indicates that the system does not release the full dose of the active ingredient immediately after oral dosing and that the formulation allows a reduction of peak plasma concentration and/or in dosage frequency. The controlled release is a pH-controlled release either triggered by the pH of the absorption side and/or the pH-modifier of the core, whichever applies first.

The term "system" as used for the expression "controlled release system" should be understood in its broadest meaning comprising any type of formulation, preparation or pharmaceutical dosage form providing a number of layers as required according to the present invention. The controlled release system may be in form of pellets, tablets, matrix tablet, mini-tablets, micro capsules or granules. The system may be administered directly or filled in another form such as a capsule or compressed into tablets together with suitable fillers.

The structure, composition and build-up of the combination of layers of the controlled release system make it possible to provide an improved control of the release system avoiding the disadvantages of prior art.

Since the pH modifier is spatially separated from flibanserin in the formulation of the controlled release system of the present invention it remains stable when stored, undesirable interactions between pH modifier and flibanserin are prevented. Only after the oral administration of the controlled release system of the present invention the pH modifier does dissolve and produces a micro environment in which flibanserin can dissolve.

In the following the optional and obligatory layers of the controlled release system will be described in detail.

a) Core Material

The core material contains at least one pH modifier. The pH modifier is not limited according to the present invention but any known chemical substance capable of providing a modified pH value may be used. Usually the pH modifier may be selected from one or more organic acids and/or organic bases and/or buffers or mixtures thereof. The pH modifier is selected to control the solubility of flibanserin, i.e. the type(s) of pH modifier selected and the amount of pH modifier adjusted has an impact on or triggers the release of flibanserin. Therefore, the choice of the pH modifier strongly depends from the active substance(s) to be used. The pH modifier controls the pH to be adjusted for flibanserin; in contrast to prior art the pH modifier of the present invention has no influence on the permeability of any outer layer.

The organic acids, bases or buffers are not limited according to the frame of the present invention but any acid, base or buffer usable in pharmaceuticals may be employed. Therefore, the pH modifier is selected from the group consisting of one or more pharmacologically acceptable organic acids, one or more pharmaceutically acceptable bases, one or more pharmaceutically acceptable buffers, derivatives and mixtures thereof.

The term "one or more" or "at least one" as used in the present invention stands for 1, 2, 3, 4, 5, 6, 7, 8, 9, 10 compounds or even more. Preferred embodiments comprise 1, 2 or 3 such compounds. More preferred embodiments comprise 1 or 2 such compounds and even more preferred are embodiments comprising one of such compounds.

The pH modifier may be in solid or liquid form. The pH modifier is not necessarily used in the form of a solid or mixture of solids but it may be employed in form of a liquid or mixtures of liquids, for example, by firstly adhering or coating the pH modifier onto a carrier or carrier particles and then forming the core containing the pH modifier. For instance, the adhering or coating can be carried out by a conventional coating method which is usually used in the preparation of pharmaceutical preparations, such as fluidized bed coating, pan coating, or the like. The inert carrier may include particles of a carrier substance, such as sucrose, lactose, starches, crystalline cellulose, calcium phosphates, silicium dioxide and derivatives thereof, and the like.

The pharmaceutically acceptable organic acids and/or bases to be contained in the core may be preferably selected from the group consisting of acetic acid, adipic acid, ascorbic acid, l-alanine, arginine, asparagines, aspartic acid, benzenesulphonic acid (besylate), benzoic acid, p-bromophenylsulphonic acid, camphorsulphonic acid, carbonic acid, gamma-carboxyglutamic acid, citric acid, cysteine, ethanesulphonic acid, fumaric acid, particularly cis-fumaric acid and/or trans-fumaric acid, gluconic acid, glutamic acid, glutaric acid, l-glutamine, hydrobromic acid, hydrochloric acid, hydroiodic acid, isethionic acid, isoleucine, lactic acid, l-leucine, lysine, maleic acid, malic acid, malonic acid, mandelic acid, methanesulphonic acid (mesylate), methionine, mucinic acid, nitric acid, ornithine, oxalic acid, pamoic acid, pantothenic acid, phosphoric acid, serine, sorbic acid, succinic acid, sulphuric acid, tartaric acid, p-toluenesulphonic acid, tyrosine glutamic acid, valine and derivatives and mixtures thereof. The above listing is not intended to be of limitative character, the skilled person is familiar with further examples.

Particularly preferred organic acids are acetic acid, ascorbic acid, tartaric acid, glutaric acid, malic acid, fumaric acid, citric acid, lactic acid, adipic acid and succinic acid or combinations thereof.

As derivatives e.g. the hydrates or the salts of the acids may be used such as alkali and earth alkali salts or ammonium salts. The preferred type depends on the intended use of the controlled release system. Particularly preferred are salts of weak organic acids such as succinic acid, fumaric acid, malic acid, tartaric acid, glutaric acid, citric acid, formic acid, acetic acid, adipic acid, ascorbic acid, maleic acid, or lactic acid. Particularly suitable salts are sodium succinate, sodium citrate, and sodium acetate.

The buffer is preferably selected from one or more pharmaceutically acceptable or compatible buffers or buffering agents for example McIlvaine buffers (for example citric acid phosphate buffer, pH 2.2-7.0), ammonia solution, calcium carbonate, tribasic calcium phosphate, citric acid monohydrate, dibasic sodium or potassium phosphate (for example pH 5.0-8.0), diethanolamine, malic acid, monobasic sodium phosphate, monoethanolamine, monosodium glutamate, phosphoric acid, potassium citrate, sodium acetate, sodium bicarbonate, sodium borate, sodium citrate dihydrate, sodium hydroxide, sodium lactate, triethanolamine and derivatives and mixtures thereof.

The core material used is preferably a pharmaceutically acceptable pH modifier to which 0 to 50% by weight, preferably 0.1 to 25% by weight, more preferably 1 to 10% by weight, even more preferably 2 to 8% by weight, and most preferably 3 to 6% by weight of a suitable binder is optionally added.

The content of the pharmaceutically acceptable pH modifier(s) is usually between 30 and 100% in the core material. However, it is also possible to use pure (100%) pH modifier as the starting material, then it may be advantageous to use a sufficiently narrow range of particle sizes.

It should be noted that the ranges of values given herein expressly include all the numerical values, both whole numbers and fractions, within the ranges as specified. The numerals given are always the percent by weight values. Percent by weight value means the percentage with respect to an individual part of the dosage form like the core or the coating.

As binder, it is possible to use any binder usually employed in pharmaceuticals. Exemplarily mentioned are naturally occuring or partially or totally synthetic polymers selected from among acacia, agar, gum arabic, alginic acid, carbomers, carrageenan, ceratonia, chitosan, confectionar's sugar, copovidone, povidone, cottonseed oil, dextrate, dextrin, dextrose, polydextrose, maltodextrin, maltose, cellulose and derivatives thereof such as microcrystalline cellulose, methylcelluloses, hydroxypropyl methyl celluloses, ethylcelluloses, hydroxyethyl celluloses, hydroxyethyl methylcelluloses, hydroxypropyl celluloses, carboxymethylcelluloses, carmellose sodium, hypromelloses (cellulose hydroxypropyl methylether), cellulose acetate phthalate, starch and derivatives thereof, such as pregelatinized starch, hydroxypropylstarch, corn starch, gelatin, glyceryl behenate, guar gum, hydrogenated vegetable oils, inulin, lactose, glucose, magnesium aluminium silicate, poloxamer, polycarbophils, polyethylene oxide, polyvinylpyrrolidone, copolymers of N-vinylpyrrolidone and vinyl acetate, polymethacrylates, alginates auch as sodium alginate, stearic acid, sucrose, sunflower oil, zein as well as derivatives and mixtures thereof.

The term "derivatives" according to the present invention is meant to include any compound derived from the mentioned compounds as basic system, for example by substitution with one or more functional groups. This belongs to the general knowledge of the skilled person.

Particularly preferred binders are gum arabic, hydroxypropyl celluloses, hydroxypropyl methylcelluloses, methylcelluloses, hydroxyethyl celluloses, carboxymethylcelluloses, carmellose sodium, povidone, corn starch, polyvinylpyrrolidone, the copolymers of N-vinylpyrrolidone and vinyl acetate, or combinations of these polymers. The above listing is not intended to be of limitative character, the skilled person is familiar with further examples.

As a matter of course also other additives, excipients, carriers, technological adjuvants suitable in pharmaceutical formulations may be present such as as lubricants, glidants, agents to improve flowability, granulating agents, anti-caking agents, agglomeration inhibitors, pore formers, anti-adherents, anti-tacking agent, anti-sticking agent, flavors, aromatiziers, dyes or colorants, preservatives, plasticizers, diluents, wetting agents, sweeteners, disintegrants, tonicity agents, chelating agents, stabilizers, solubilizers, antioxidants, fillers, pigments and the like. These pharmaceutically acceptable formulating agents are e.g. present in order to promote the manufacture, compressibility, appearance and/or taste of the preparation. Other conventional additives known in the art can also be included. The above listing is not intended to be of limitative character, the skilled person is familiar with further examples.

The core material which may be spherical, has preferably an average diameter of 0.1-5 mm, more preferably 0.2-2 mm and most preferably 0.4-1.5 mm. Actually, the core to be coated may be in any suitable form such as crystals, microparticulates, beads, tablets, capsules, pills, pellets, granules, or fine granules.

The core can be manufactured by techniques generally known in the art such as direct pressing, extrusion and followed by forming to preferably rounded shape, moist or dry granulation or direct pelleting, for example on plates or rotor pelletizers, or by binding of powders, such as powder layering on spherules (nonpareils). The core which is free of flibanserin can be homogeneous or can have a layered structure or any other build-up known by those skilled in the art.

b) Optional Insulating/Mobiliy Decreasing Layer

To coat the core material before the application of the further layer(s) with an insulating/mobility decreasing layer based on a water-soluble, pharmaceutically acceptable polymer may be advantageous for two reasons:

I) To increase the durability of the finished core product material.

II) To decrease the mobility of the pH modifier and control interactions between the pH modifier and the following layer (first layer), especially if the first layer contains Eudragit® RS.

Examples of such water-soluble polymers include gum arabic or a partially or totally synthetic polymer selected from the alkyl celluloses and derivatives thereof such as methylcelluloses, hydroxyalkyl celluloses and derivatives thereof such as hydroxyethyl celluloses, hydroxypropyl celluloses, hydroxyalkyl alkylcelluloses and derivatives thereof such as the hydroxypropylmethyl celluloses, carboxyalkylcelluloses such as carboxymethylcelluloses, polyvinylpyrrolidones, copolymers of N-vinylpyrrolidone and vinyl acetate or combinations of said polymers and derivatives and mixtures thereof. Gum arabic or a hydroxyalkyl alkylcellulose such as hydroxypropyl methylcellulose is preferably used. If desired, the coating with the water-soluble, pharmaceutically acceptable polymer may be carried out with the addition of excipients, preferably one or more suitable plasticizers, one or more separating agents and/or one or more pigments.

Exemplarily mentioned plasticizers are citrates such as acetyltributyl citrate, acetyltriethyl citrate, tributyl citrate, triethyl citrate, benzyl benzoate, castor oil, phthalates such as dibutyl phthalate, diethyl phthalate, dimethyl phthalate, dimeticon, fractionated coconut oil, chlorbutanol, dextrin, sebacate such as dibutyl sebacate, glycerine, glycerine derivatives such as glycerine monostearate, glycerol triacetate (triacetin), acetylated monoglyceride, mannitol, mineral oil, lanolin alcohols, palimitic acid, 2-pyrrolidone, sorbitol, stearic acid, triethanolamin, polyethyleneglycols (all types at different molecular weights of PEGs), and propylene glycol, and derivatives and mixtures thereof. Preferred plasticizers which may be used are acetylated monoglyceride, acetyltributyl citrate, acetyltriethyl citrate, dibutyl phthalate, dibutyl sebacate, diethyl phthalate, dimethyl phthalate, tributyl citrate, triethyl citrate, polyethylene glycols (all types at different molecular weigths of PEGS), and propylene glycol. Particularly preferred are triethyl citrate, tributyl citrate, polyethyleneglycols (all types at different molecular weights of PEGs), and propylene glycol.

Exemplarily mentioned separating agents are talc, silicic acid and glycerol monostearate.

Examples of pigments which are especially useful are titanium dioxide, iron oxide pigments, and some of the aluminium lakes as well as pigment black, pigment white, pigment yellow, sunset yellow, sunset yellow lake, quinoline yellow lake and the like.

Other additives, excipients, carriers, technological adjuvants, if desired, may be present.

The application quantity of the optional (first) insulating layer based on the specific surface area of the starting core is for case I): in the range from 0.05 to 5.0 mg/cm$^2$, preferably 0.1 to 3.0 mg/cm$^2$, more preferably 0.15 to 2.5 mg/cm$^2$, particularly 0.2 to 2.0 mg/cm$^2$ and more particularly 0.2 to 1.5 mg/cm$^2$, for case II): in the range from 0.1 to 30.0 mg/cm$^2$, preferably 0.2 to 20 mg/cm$^2$, more preferably 0.5 to 15 mg/cm$^2$, particularly 0.7 to 12 mg/cm$^2$ and more particularly 1 to 10 mg/cm$^2$.

c) First Layer

The first layer is provided directly on the core or on the optional insulating layer or another intermediate layer being applied on the core or the insulating layer and preferably serves as a control layer in order to support the controlled release desired. In addition, the first layer may also serve as a protective layer of the layer(s) beneath, particularly the core material. The first layer is based on a water-insoluble polymer. The water-insoluble polymer is not limited according to the present invention. Any type of pharmaceutically acceptable water-insoluble polymer may be used. The term "water-insoluble" may be understood that the compound has a solubility in water which is below 0.1 mg/ml at room temperature.

Preferably the water-insoluble polymer contained in the first layer is selected from the group consisting of an acrylic and/or methacrylic polymer which may contain a low content of quaternary ammonium groups in the alkyl moiety such as trimethylammonium-groups, alkylcelluloses such as ethylcelluloses, methylcelluloses, cellulose acetate, and polyvinyl acetate and derivates and mixtures thereof.

Preferably, the water-insoluble polymer may comprise polymers or coplymers of acrylic acid, methyl acrylate, ethyl acrylate, methacrylic acid, methyl methacrylate, ethyl methacrylate and the like which may contain quaternary ammonium groups such as ammonio (meth)acrylate copolymers. Preferred examples are copolymers of ethyl acrylate, methyl methacrylate and trimethylammonioethyl methacrylate chloride. Such an acrylic polymer is available under the name Eudragit® RS which is a water-insoluble copolymer (poly(ethyl acrylate, methyl methacrylate, trimethylammonioethyl methacrylate chloride) 1:2:0.1, manufactured by Rhöm Pharma, Germany) e.g. in form of organic-based polymeric solutions or aqueous-based polymeric dispersions thereof which may be used for coating, for example Eudragit® RS 30D. Another acrylic polymer may be Eudragit® RL which consists of the same components as Eudragit® RS but has a different molar ratio (Eudragit® RL: poly(ethylacrylate, methyl methacrylate, trimethylammonioethyl methacrylate chloride; 1:2:0.2) e.g. in form of organic-based polymeric solutions or aqueous-based polymeric dispersions thereof, for example Eudragit® RL 30D. The presence of quaternary ammonium groups appears to take advantage of ionic interactions for the release of flibanserin. This interaction can be additionally altered in an advantageous way exchanging the originally counter cation (chloride) of Eudragit® RS or RL against anions which display a higher attraction towards the quaternary ammonium group than chloride (R. Grützmann, Thesis 2005, University of Tübingen, Germany, "Zum Mechanismus der Anionenwirkung auf die Permeabilität kationischer Polymethacrylatüberzüge"). This effect can be used in an advantageous way at any step poly(ethyl acrylate, methyl methacrylate, trimethylammonioethyl methacrylate chloride) is used in this invention without being mentioned again. Not being bound by any theory it is assumed that an ion induced transport may occur wherein ionic interactions between solved anions released from the core and the cationic quaternary ammonium ions of the first layer take place. The release rate depends among other things from the anion species and the ratio of anions/cations present.

Also preferably used are, for example, poly(ethyl acrylate, methyl methacrylate) 2:1 (Eudragit® NE) e.g. in form of aqueous-based polymeric dispersions thereof, for example Eudragit® NE 30D, Kollicoat® EMM 30D; and ethylcelluloses e.g. in form of organic-based polymeric solutions or aqueous-based polymeric dispersions thereof, for example, ethylcellulose N10, N20 or N45, Aquacoate® ECD, and Surelease®.

Furthermore preferably mentioned are cellulose acetate e.g. in form of organic-based polymeric solutions thereof and/or polyvinyl acetate e.g. in form of aqueous-based polymeric dispersions thereof, for example Kollicoat® SR 30D.

The mentioned polymers may be used alone or in combination of two or more polymers. The selection of the water-insoluble (co-)polymer or mixtures of (co)polymers have an influence on the release of flibanserin in order to establish the desired release profile. Although flibanserin has a pH-dependent solubility it is possible to adjust a release profile which is independent from the pH value resulting in an improved bioavailability. Depending on the further structure of the release system the profiles may be further adjusted. For example, if the viscosity of the water-insoluble polymer used is enhanced, the retardation of the release of flibanserin may be increased (for example the viscosity is enhanced from ethylcellulose N10→N20→N40).

Other additives including but not limited to, plasticizers, glidants, anti tacking agents, surfactans, pigments and other coloring agents and/or pore formers may be present in an amount up to 70% of the entire layer, depending on the polymer used which belongs to the general knowledge of the skilled person. Preferably one or more plasticizers are present, particularly those as already described. Preferably used plasticizers are selected from the group consisting of acetylated monoglyceride, acetyltributyl citrate, acetyltriethyl citrate, castor oil, dibutyl phthalate, dibutyl sebacate, diethyl phthalate, dimethyl phthalate, fractionated coconut oil, glycerine, glycerine triacetate (triacetin), tributyl citrate, triethyl citrate, polyethylenen glycols (all types at different molecular weights of PEGs), and propylene glycol.

Therefore, the first layer may be obtained using organic-based polymeric solutions or aqueous-based polymeric solutions or dispersions to be sprayed onto the starter core, which preferably contain or consist of one or more water-insoluble polymer as above-described and preferably excipients, e.g. with or without plasticizer(s), with or without anti-tacking agent(s), with or without pore-former(s) and/or solvent(s) and/or vehicle(s).

An anti-tacking agent, anti-sticking agent or glidant or agent to improve flowability can be used to improve powder flow properties prior to and during the manufacturing process and to reduce caking. A lubricant and agglomeration inhibitor can be used to enhance release of the dosage form from the apparatus on which it is formed, for example by preventing adherence to the surface of an upper punch ("picking") or lower punch ("sticking"). Among this group of excipients may be exemplarily mentioned boric acid, calcium silicate, cellulose, particularly powdered cellulose, colloidal silicon dioxide (e.g. Aerosil®, Cab-O-Sil®), DL-leucine, magnesium silicate, magnesium trisilicate, talc, silicon dioxide, starch, tribasic calcium phosphate, glyceryl behenate (e.g. Compritol® 888), magnesium oxide, mineral oil, poloxamer, polyvinyl alcohol, hydrogenated oils such as hydrogenated vegetable oils (e.g. Sterotex®), hydrogenated castor oil, kaolin, (light) mineral oil, canola oil, triglycerides, such as medium-chain triglycerides, myristic acid, palmitic acid, polyethylene glycols (all types at different molecular weights of PEGs), benzoate such as sodium or potassium benzoate, sodium chloride, sodium lauryl sulfate, magnesium lauryl sulphate, sodium acetate, sodium benzoate, sodium fumarate, sodium oleate, sodium stearyl fumarate, talc, stearic acid and salts including magnesium, calcium, sodium and zinc stearate, glycerol monostearate, glyceryl palmitostearate, macrogol, like macrogol 400 or 6000, polyoxyl-40-stearate, waxes and the like.

Possible surfactants are lecithin, polysorbate 80, sodium lauryl sulfate, poloxamers, polyethylene glycol, sucrose fatty acid esters, polyoxyethylene hardened castor oil, polyoxyethylene fatty acid ester, polyoxyethylene glycol, polyoxyethylene sorbitan fatty acid ester, alkylbenzene sulfonate, sulfosuccinate ester salts, hydroxypropylcellulose, ammonium lauryl sulfate, and other alkyl sulfate salts, sodium laureth sulfate, cetyl trimethylammonium bromide (CTAB), hexadecyl trimethyl ammonium bromide, and other alkyltrimethylammonium salts, cetyl pyridinium chloride, polyethoxylated tallow amine (POEA) benzalkonium chloride, dodecyl betaine, dodecyl dimethylamine oxide, cocamidopropyl betaine, coco ampho glycinate, alkyl polyglucosides, including octyl glucoside and decyl maltoside, cetyl alcohol, oleyl alcohol and cocamide or mixtures thereof.

The application quantity of the of the surfactants based on the whole amount of the first layer is in the range from 0 to 10% by weight, preferably from 0.5 to 5.0% by weight, and more preferably from 1 to 3% by weight.

Possible pore formers are methylcellulose, hydroxypropyl methylcelluloses, hydroxypropyl cellulose, hydroxyethyl cellulose, povidone (e.g. Kollidon 17), Eudragit® E (Poly (butyl methacrylate, (2-dimethylaminoethyl)methacrylate, methyl methacrylate) 1:2:1), alginic acid and salts thereof including calcium, potassium, propylene glycol, and sodium alginate, gelatin, povidone, and polyvinyl alcohol.

The application quantity of the first layer based on the specific surface area of the starting core is in the range from 0.1 to 15 mg/cm$^2$, preferably 0.5 to 12 mg/cm$^2$, more preferably 1.0 to 10 mg/cm$^2$, particularly 1.5 to 8.0 mg/cm$^2$ and more particularly 2.0 to 6.0 mg/cm$^2$.

In a preferred embodiment of the present invention the first layer comprises a polymer selected from the group consisting of Eudragit® RS, Eudragit® RL, Eudragit® NE, ethylcellulose (N10, N20 or N45) and/or mixtures thereof in an amount of 2.0 to 4.5 mg/cm$^2$ (calculated as dry matter of the polymer or polymer mixture), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

It is also possible to control the release of flibanserin based on the quantity of the applied layer. For example if the application amount is increased, the retardation effect will be increased. However, increased layer thickness is not desired due to increasing costs and increasing weight of the application form. Further the ratio flibanserin/excipients will be unfavourable resulting in a poor compliance of the patient. As a result, it is a better way to control release by the composition and structure of the layers used.

d) Second Layer

The second layer contains flibanserin. The controlled release system containing flibanserin can be used for the treatment of the same diseases as already described for the extended release system.

As for the extended release system flibanserin is contained in an amount suitable for exhibiting the desired pharmacological activities. Also the dosis range applicable per day as well as the dose regimen is the same as for the extended release system.

The preferred flibanserin content is not more than 60%, preferably not more than 50% of the whole controlled release system.

Unless otherwise stated, percentages specified are always percent by weight.

The active substance layer contains flibanserin as well as preferably one or more binders and/or optionally one or more separating agents and/or other excipients. The term "excipients" or "additives" or "adjuvants" as understood for the controlled release system shall mean any known suitable auxiliary compound which may be used in pharmaceuticals in order to provide one or more functionalities to the controlled release system according to the present invention.

For example suitable binders may be those as described in connection with the core material. Preferably used are cellulose and derivatives thereof such as hydroxypropyl celluloses (e.g. Klucel EF), hydroxypropylmethyl celluloses, methylcelluloses, hydroxyethyl celluloses, carboxymethylcelluloses, cellulose acetate phthalate, polyvinylpyrrolidone (PVP), copolymers of N-vinylpyrrolidone, gelatin, shellac, hydroxypropyl methylcellulose phthalate, for example HP 55® or HP 50®, polymers and copolymers of acrylic and methacrylic acid and the esters thereof, or combinations of these polymers such as polymethacrylates, starches and derivatives thereof, sugars, vinyl acetate or combinations of these polymers and derivatives thereof. Most preferably used are hydroxypropyl cellulose or copolymers of N-vinylpyrrolidone and vinyl acetate.

The addition of suitable separating agents such as e.g. talc, magnesium stearate or silicic acid serves to prevent the particles from aggregating during the manufacturing process.

Beside binding agents and separating agents, the second layer may also incorporate various other conventional additives, excipients, carriers, technological adjuvants such as fillers, diluents, lubricants, glidants, agents to improve flowability, pore formers, anti-adherents, anti-tacking agents, flavors, preservatives, sweetening agents, disintegrants, dyes and the like. The above listing is not intended to be of limitative character, other conventional additives known in the art can also be included.

As further excipients which may be present the following non limitative groups are given preservatives, preferably antimicrobial preservatives such as benzalkonium chloride, benzoic acid, methyl parahydroxybenzoate, propyl parahydroxybenzoate, sodium benzoate, and sorbic acid;

sweetening agents such as acesulfame potassium, alitame, aspartame, compressible sugar, confectioner's sugar, dextrose, erythritol, fructose, glycerin, inulin, isomalt, lactitol, liquid glucose, maltitol, maltose, mannitol, neospheridin dihydrochalcone, polydextrose, saccharin, saccharin sodium, sodium cyclamate, sorbitol, sucralose, sucrose, thaumatin, trehalose, xylitol; and disintegrants such as alginic acid and salts thereof including calcium, sodium, magnesium, carboxymethylcellulose calcium, carboxymethylcellulose sodium, powdered cellulose, chitosan, colloidal silicon dioxide, crospovidone, croscarmellose sodium, docusate sodium, guar gum, hydroxypropyl cellulose, particularly low-substituted hydroxypropyl cellulose, hydroxypropyl starch, magnesium aluminum silicate, methylcellulose, micocrystalline cellulose, polacrilin potassium, povidone, sodium starch glycolate, starch, particularly pregelatinized starch, and corn starch.

Suitable fillers may be selected from, for example, lactose, in particular lactose monohydrate, talc, sunflower oil, tragacanth, starches and derivatives such as pregelatinized starch or sterilizable maize, alginate such as ammonium alginate, sodium alginate, sodium chloride, calcium carbonate, dibasic calcium phosphate, calcium sulphate, dicalcium or tricalcium phosphate, magnesium carbonate, magnesium oxide, cellulose and derivatives, such as microcrystalline or silicified microcrystalline cellulose, cellulose acetate, ethylcellulose, sugars and derivatives such as confectioner's sugar, fructose, sucrose, dextrate, dextrin, sulfobutylether β-cyclodextrin, dextrose, polydextrose, trehalose, maltose, maltitol, mannitol, maltodextrin, sorbitol, inulin, xylitol, erythritol, fumaric acid, glyceryl palmitostearate, tablettose, hydrogenated vegetable oils, isomalt, kaolin, lactitol, triglycerides, particularly medium-chain triglycerides, polymethacrylate, and simethicone as well as derivatives or mixtures thereof.

It is a matter of course that an additive may have more then one functionality so that they may be categorized among more than one type of additive. For example corn starch or pregelatinized starch may impart several functions at the same time such as swelling polymer, filler, glidant, and the like. However, the skilled person knows the several functions and is able to select the additive according to the intended use thereof. The selection of additives depends from a variety of factors such as the desired application field, dose form and the like. Such requirements are known by the skilled person.

The application quantity of the second layer based on the specific surface area of the starting core is in the range from 0.1 to 20 mg/cm$^2$, preferably 1.0 to 18 mg/cm$^2$, more preferably 5.0 to 15 mg/cm$^2$, particularly 7.0 to 13 mg/cm$^2$, more particularly 8.0 to 12.0 mg/cm$^2$.

According to an alternative embodiment of the controlled release system of the present invention it is also possible to provide an optional insulating layer applied on the second layer containing flibanserin. Said insulating layer may be provided additionally or alternatively to the first insulating layer b) described above. The second insulating layer may have the same structure and composition as already described above for the first insulating layer.

The application quantity of the optional (second) insulating layer based on the specific surface area of the starting core is in the range from 0.05 to 5.0 mg/cm$^2$, preferably 0.1 to 3.0 mg/cm$^2$, more preferably 0.15 to 2.5 mg/cm$^2$, particularly 0.2 to 2.0 mg/cm$^2$ and more particularly 0.2 to 1.5 mg/cm$^2$.

e) Third Layer

The third layer which may be a controlled release outer coating layer comprises or consists of one or more polymers having anionic or no ionic groups. This polymer is not limited according to the present invention. Any type of pharmaceutically acceptable polymer having anionic or no ionic groups may be used.

The polymer having anionic or no ionic groups contained in the third layer may be selected from polymers and/or copolymers comprising acrylic and/or methacrylic acids or derivatives thereof (having no cationic groups such as quaternary ammonium groups, particularly no trimethylammonium-ethyl groups), alkylcelluloses and derivatives thereof, such as ethylcelluloses, hydroxyalkyl celluloses and derivatives thereof, hydroxyalkyl alkylcelluloses, like hydroxypropyl methylcellulose (e.g. Hypromellose E5), and derivatives thereof such as hydroxypropylmethyl cellulose phthalates (e.g. HP 55® or HP 50®), hydroxypropyl methylcellulose acetate succinate, cellulose acetates and derivatives thereof such as cellulose acetate phthalate, cellulose acetate trimellitate, polyvinyl acetates and derivatives thereof such as polyvinyl acetate phthalate, shellac, derivatives and mixtures thereof. Particularly preferred polymers are ethylcelluloses in different grades such as varying ethoxyl content and molecular weight, e.g. in form of organic-based polymeric solutions or aqueous-based polymeric dispersions thereof, for example, ethylcellulose N10, N20 or N45, Aquacoat® ECD, Surelease®, Chitosan, Shellac, and Zein.

Also preferably used are, for example, poly(ethyl acrylate, methyl methacrylate) 2:1 (Eudragit® NE), e.g. in form of aqueous-based polymeric dispersions thereof, for example Eudragit® NE 30D, Kollicoat® EMM 30D; poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); hydroxypropyl methylcellulose acetate succinate, for example organic-based polymeric solutions or aqueous-based polymeric dispersions thereof; hydroxypropyl methylcellulose phthalate, for example organic-based polymeric solutions or aqueous-based polymeric dispersions thereof; cellulose acetate trimellitate, for example organic-based polymeric solutions thereof; hydroxypropyl methylcellulose phthalate, for example HP 55® or HP 50®, cellulose acetate phthalate, for example organic-based polymeric solutions or aqueous-based polymeric dispersions thereof such as Aquacoat® CPD; polyvinyl acetate phthalate, for example aqueous-based polymeric dispersions thereof such as Sureteric® and shellac, for example organic-based polymeric solutions or aqueous-based polymeric dispersions thereof.

Furthermore preferably mentioned are cellulose acetate and derivatives thereof such as organic-based polymeric solutions thereof and/or polyvinyl acetate and derivatives thereof such as aqueous-based polymeric dispersions thereof, for example Kollicoat® SR 30D.

The mentioned polymers may be used alone or in combination of two or more polymers.

Eudragit® RS, or Eudragit RL® having cationic groups are excluded to be present in the third layer.

According to a preferred embodiment the polymer(s) present in the third layer is (are) identical or different from the polymer(s) present in the first layer. For example the polymer(s) of the first and second layer may be the same.

Preferably one or more plasticizers are present in the third layer. The plasticizers may be selected from the plasticizers already described in connection with the optional insulating layer. More preferably the plasticizer is selected from the group consisting of acetylated monoglyceride, acetyltributyl citrate, acetyltriethyl citrate, dibutyl phthalate, dibutyl sebacate, diethyl phthalate, dimethyl phthalate, tributyl citrate, triethyl citrate, polyethylene glycols (all types at different molecular weigths of PEGs), and propylene glycol.

Preferably one or more pore formers are present in the third layer. Possible pore formers are methylcellulose, hydroxypropyl methylcelluloses (e.g. hypromellose E5), hydroxypropyl cellulose, hydroxyethyl cellulose, Eudragit® E (Poly (butyl methacrylate, (2-dimethylaminoethyl)methacrylate, methyl methacrylate) 1:2:1), alginic acid and salts thereof including calcium, potassium, propylene glycol, and sodium alginate, gelatin, povidone (e.g. Kollidon 17), and polyvinyl alcohol.

Other additives may be used such as lubricants, antiadherents, anticaking agents, fillers and the like.

In a preferred embodiment of the controlled release system of the present invention the third layer comprises a polymer selected from the group consisting of Eudragit® NE, ethylcellulose (N10, N20 or N45) Kollicoat®EMM 30D; poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); and/or mixtures thereof in an amount of 0.2 to 3.0 mg/cm$^2$ (calculated as dry matter of the polymer or polymer mixture), a pore former selected from the group consisting of methylcellulose, hydroxypropyl methylcelluloses, hydroxypropyl cellulose, hydroxyethyl cellulose, povidone (e.g. Kollidon 17) and Eudragit® E (Poly(butyl methacrylate, (2-dimethylaminoethyl)methacrylate, methyl methacrylate) 1:2:1) in an amount of 30 to 300% (w/w, based on the dry polymer/polymer-mixture matter of the layer), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and optionally an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

In a further preferred embodiment of the present invention the third layer comprises a polymer selected from the group consisting of Eudragit® NE, ethylcellulose (N10, N20 or N45) Kollicoat®EMM 30D; poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); and/or mixtures thereof in an amount of 0.2 to 3.0 mg/cm$^2$ (calculated as dry matter of the polymer or polymer mixture), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and optionally an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

Preferably, the polymers used in the third layer are selected from the group consisting of selected from the group consisting of ethylcellulose, hydroxypropyl methylcellulose phthalate, and poly(methacrylic acid, ethylacrylate) 1:1 (Eudragit® L 100-55 or Eudragit® L 30D-55); and/or mixtures thereof, more preferably from the group consisting of ethylcellulose and poly(methacrylic acid, ethylacrylate) 1:1 (Eudragit® L 100-55 or Eudragit® L 30D-55); and/or mixtures thereof.

The application quantity of the third layer based on the specific surface area of the starting core is in the range from 0.1 to 15 mg/cm$^2$, preferably 0.2 to 12 mg/cm$^2$, more preferably 0.5 to 10 mg/cm$^2$, particularly 0.7 to 8.0 mg/cm$^2$, more particularly 0.8 to 5.0 mg/cm$^2$.

f) Optional Fourth Layer

The optional fourth layer may preferably be an outer coating layer. Said optional outermost layer, which may serve to reduce any increased abrasion during packing, e.g. into capsules and/or to increase the shelf life and/or as further diffusion barrier, comprises or consists of one or more pharmaceutically conventional film-forming agents and optionally excipients, particularly preferred are plasticizers and pigments.

Suitable film-forming agents to reduce increased abrasion and/or can serve as further diffusion barrier include for example ammonium alginate, chitosan, chlorpheniramine maleate, copovidone, phthalate such as dibutyl phthalate, diethyl phthalate, dimethyl phthalate, cellulose acetate phthalate, polyvinyl acetate phthalate, dibutyl sebacate, ethyl lactate, alkylcelluloses and derivatives thereof such as ethylcelluloses, methylcelluloses, gelatin, hydroxyalkyl celluloses and derivatives thereof such as hydroxyethyl cellulose, hydroxypropyl cellulose, hydroxyalkyl alkylcellulose and derivatives thereof such as hypromelloses (hydroxypropyl methylcellulose), hydroxypropyl methylcellulose acetate succinate, hydroxypropyl methylcellulose phthalate, cellulose acetate trimellitate, cellulose acetate phthalate, maltodextrin, calcium carbonate, polydextrose, polyethylene glycols (all types at different molecular weigths of PEGs), polyethylene oxide, polymers and copolymers of acrylic and methacrylic acid and the esters thereof, or combinations of these polymers such as polymethacrylates, poly(methylvinyl ether/maleic anhydride), polyvinyl acetate phthalate, triethyl citrate, vanillin, shellac, Zein, as well as derivatives and mixtures thereof.

Particularly preferred film-forming agents are hydroxypropyl cellulose, hydroxypropyl methylcellulose, methylcelluloses, polymers and copolymers of acrylic and methacrylic acid and the esters thereof, or combinations of these polymers, for example used in form of organic-based polymeric solutions or aqueous-based polymeric dispersions thereof. Also preferred polymers are poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); hydroxypropyl methylcellulose acetate succinate, for example organic-based polymeric solutions or aqueous-based polymeric dispersions thereof; hydroxypropyl methylcellulose phthalate, for example organic-based polymeric solutions or aqueous-based polymeric dispersions thereof; cellulose acetate trimellitate, for example organic-based polymeric solutions thereof; cellulose acetate phthalate, for example organic-based polymeric solutions or aqueous-based polymeric dispersions thereof such as Aquacoate® CPD; polyvinyl acetate phthalate, for example aqueous-based polymeric dispersions thereof such as Sureteric® and shellac, for example organic-based polymeric solutions or aqueous-based polymeric dispersions thereof.

The compounds are partly commercially available in form of organic-based solutions or dispersions or aqueous-based solutions or dispersions. It is also possible to produce such solutions or dispersions. The expressions "organic-based" and "aqueous-based" systems shall be understood to be directed to the solvents or dispergants mainly present in the liquid system to be used. Also mixtures of solvents and/or dispergants may be included.

Suitable plasticizers are already described, preferably are used inter alia triethyl citrate, tributyl citrate, triacetin or polyethyleneglycols. Preferred pigments used may be e.g. titanium dioxide or iron oxide pigments. Also fillers may be contained, possible fillers are described above. Other known additives may be present, if desired.

It is particularly preferred if the optional fourth layer is omitted in the controlled release system according to the present invention. However, the controlled release system of the invention may comprise this fourth layer as a type of non-functional coating in case intended as an abrasion protective layer or a functional coating in case the layer is intended as a diffusion barrier. The term "non-functional" in the present context means having no substantial effect on release properties of the controlled release system, and the coating serves another useful purpose. For example, such a coating can impart a distinctive appearance to the dosage form, provide protection against attrition during packaging and transportation, improve ease of swallowing, and/or have other benefits. A non-functional coating should be applied in an amount sufficient to provide complete coverage of the controlled release system. Typically an amount of about 1% to about 10%, more typically an amount of about 2% to about 5%, by weight of the controlled release system as a whole, is suitable.

In a preferred embodiment of the present invention where the fourth layer is intended to protect the drug product from abrasion the layer comprises a polymer selected from the group consisting of hydroxypropyl cellulose, hydroxypropyl methylcellulose, methylcelluloses, Eudragit® E (Poly(butyl methacrylate, (2-dimethylaminoethyl)methacrylate, methyl methacrylate) 1:2:1); and/or mixtures thereof in an amount of 0.2 to 1.5 mg/cm$^2$ (calculated as dry matter of the polymer or polymer mixture), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

In another preferred embodiment of the present invention where the fourth layer is intended as an additional diffusion barrier the layer comprises a polymer selected from the group consisting of Eudragit® NE, ethylcellulose (N10, N20 or N45), Kollicoat® EMM 30D, poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); and/or mixtures thereof in an amount of 0.5 to 2.5 mg/cm$^2$ (calculated as dry matter of the polymer or polymer mixture). Additionally the fourth layer comprises a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and optionally an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

In a further preferred embodiment of the present invention where the fourth layer is intended as an additional diffusion barrier the layer comprises a polymer selected from the group consisting of Eudragit® NE, ethylcellulose (N10, N20 or N45), Kollicoat® EMM 30D; poly(methacrylic acid, ethylacrylate) 1:1 (Eudragit® L 100-55 or Eudragit® L 30D-55); poly(methacrylic acid, methyl methacrylate) 1:1 (Eudragit® L 100); poly(methacrylic acid, methyl methacrylate) 1:2 (Eudragit® S); and/or mixtures thereof in an amount of 1.0 to 5.0 mg/cm$^2$ (calculated as dry matter of the polymer or polymer mixture), a pore former selected from the group consisting of methylcellulose, hydroxypropyl methylcelluloses, hydroxypropyl cellulose, hydroxyethyl cellulose, povidone (e.g. Kollidon 17) and Eudragit® E (Poly(butyl methacrylate, (2-dimethylaminoethyl)methacrylate, methyl methacrylate) 1:2:1) in an amount of 30 to 300% (w/w, based on the dry polymer/polymer-mixture matter of the layer), a plasticizer from the group consisting of acetyltributyl citrate, acetyltriethyl citrate, dibutyl phthalate, dibutyl sebacate, diethyl phthalate, dimethyl phthalate, glycerine triacetate (triacetin), tributyl citrate, triethyl citrate, polyethylenen glycols in an amount 10 to 30% (w/w, based on the dry polymer/polymer-mixture matter of the layer) and optionally an anti-tacking agent, anti-sticking agent or glidant from the group consisting of glycerol monostearate, talc or polyethylene glycol in an amount of 0 to 20% (w/w, based on the dry polymer/polymer-mixture matter of the layer).

Preferably, if the fourth layer is intended as an additional diffusion barrier, the layer comprises a polymer is selected from the group consisting of ethylcellulose, hydroxypropyl methylcellulose phthalate, and poly(methacrylic acid, ethylacrylate) 1:1 (Eudragit® L 100-55 or Eudragit® L 30D-55); and/or mixtures thereof, more preferably selected from the group consisting of hydroxypropyl methylcellulose phthalate, and poly(methacrylic acid, ethylacrylate) 1:1 (Eudragit® L 100-55 or Eudragit® L 30D-55); and/or mixtures thereof and most preferably the polymer is poly(methacrylic acid, ethylacrylate) 1:1 (Eudragit® L 100-55 or Eudragit® L 30D-55).

The application quantity of the fourth layer based on the specific surface area of the starting core is in the range from 0.1 to 15 mg/cm$^2$, preferably 0.2 to 12 mg/cm$^2$, more preferably 0.5 to 10 mg/cm$^2$, particularly 0.7 to 8.0 mg/cm$^2$, more particularly 0.8 to 5.0 mg/cm$^2$.

According to a preferred embodiment, the controlled release system of the present invention is characterized in that the application quantities for the layers present, based on the specific surface area of the starting core, are as follows:
optional (first) insulating layer:
in the range from 0.05 to 5.0 mg/cm$^2$;
first layer:
in the range from 0.1 to 15 mg/cm$^2$;
second layer:
in the range from 0.1 to 20 mg/cm$^2$;
third layer:
in the range from 0.1 to 15 mg/cm$^2$, and
optional fourth layer:
in the range from 0.1 to 15 mg/cm$^2$.

According to a more preferred embodiment, the controlled release system of the present invention is characterized in that the application quantities for the layers present, based on the specific surface area of the starting core, are as follows:
optional (first) insulating layer:
in the range from 0.1 mg/cm$^2$, to 3.0 mg/cm$^2$;
first layer:
in the range from 0.5 to 12 mg/cm$^2$;
second layer:
in the range from 1 to 18 mg/cm$^2$;
third layer:
in the range from 0.2 to 12 mg/cm$^2$, and
optional fourth layer:
in the range from 0.2 to 12 mg/cm$^2$.

According to a even more preferred embodiment, the controlled release system of the present invention is characterized in that the application quantities for the layers present, based on the specific surface area of the starting core, are as follows:
optional (first) insulating layer:
in the range from 0.15 mg/cm$^2$, to 2.5 mg/cm$^2$;
first layer:
in the range from 1 to 10 mg/cm$^2$;
second layer:
in the range from 5 to 15 mg/cm$^2$;
third layer:
in the range from 0.5 to 10 mg/cm$^2$, and
optional fourth layer:
in the range from 0.5 to 10 mg/cm$^2$.

According to an even more preferred embodiment, the controlled release system of the present invention is characterized in that the application quantities for the layers present, based on the specific surface area of the starting core, are as follows:
optional (first) insulating layer:
in the range from 0.2 mg/cm$^2$, to 2.0 mg/cm$^2$;
first layer:
in the range from 1.5 to 8 mg/cm$^2$;
second layer:
in the range from 7 to 13 mg/cm$^2$;
third layer:
in the range from 0.7 to 8 mg/cm$^2$, and
optional fourth layer:
in the range from 0.7 to 8 mg/cm$^2$.

According to a most preferred embodiment, the controlled release system of the present invention is characterized in that the application quantities for the layers present, based on the specific surface area of the starting core, are as follows:
optional (first) insulating layer:
in the range from 0.2 mg/cm$^2$, to 1.5 mg/cm$^2$;
first layer:
in the range from 2 to 6 mg/cm$^2$;
second layer:
in the range from 8 to 12 mg/cm$^2$;
third layer:
in the range from 0.8 to 5 mg/cm$^2$, and
optional fourth layer:
in the range from 0.8 to 5 mg/cm$^2$.

According to a further preferred embodiment, the controlled release system of the present invention is characterized in that the application quantities for the layers present, based on the specific surface area of the starting core, are as follows:
optional (first) insulating layer:
in the range from 0.05 to 30.0 mg/cm$^2$;
first layer:
in the range from 0.1 to 15 mg/cm$^2$;
second layer:
in the range from 0.1 to 20 mg/cm$^2$;
third layer:
in the range from 0.1 to 15 mg/cm$^2$, and
optional fourth layer:
in the range from 0.1 to 15 mg/cm$^2$.

According to a more preferred embodiment, the controlled release system of the present invention is characterized in that the application quantities for the layers present, based on the specific surface area of the starting core, are as follows:
optional (first) insulating layer:
in the range from 0.1 mg/cm$^2$, to 20.0 mg/cm$^2$;
first layer:
in the range from 0.5 to 12 mg/cm$^2$;
second layer:
in the range from 1 to 18 mg/cm$^2$;
third layer:
in the range from 0.2 to 12 mg/cm$^2$, and
optional fourth layer:
in the range from 0.2 to 12 mg/cm$^2$.

According to a even more preferred embodiment, the controlled release system of the present invention is characterized in that the application quantities for the layers present, based on the specific surface area of the starting core, are as follows:
optional (first) insulating layer:
in the range from 0.15 mg/cm$^2$, to 15 mg/cm$^2$;
first layer:
in the range from 1 to 10 mg/cm$^2$;
second layer:
in the range from 5 to 15 mg/cm$^2$;
third layer:
in the range from 0.5 to 10 mg/cm$^2$, and
optional fourth layer:
in the range from 0.5 to 10 mg/cm$^2$.

According to a even more preferred embodiment, the controlled release system of the present invention is characterized in that the application quantities for the layers present, based on the specific surface area of the starting core, are as follows:
optional (first) insulating layer:
in the range from 0.2 mg/cm$^2$, to 12 mg/cm$^2$;
first layer:
in the range from 1.5 to 8 mg/cm$^2$;
second layer:
in the range from 7 to 13 mg/cm$^2$;
third layer:
in the range from 0.7 to 8 mg/cm$^2$, and
optional fourth layer:
in the range from 0.7 to 8 mg/cm$^2$.

According to a most preferred embodiment, the controlled release system of the present invention is characterized in that the application quantities for the layers present, based on the specific surface area of the starting core, are as follows:
optional (first) insulating layer:
in the range from 0.2 mg/cm$^2$, to 10 mg/cm$^2$;
first layer:
in the range from 2 to 6 mg/cm$^2$;
second layer:
in the range from 8 to 12 mg/cm$^2$;
third layer:
in the range from 0.8 to 5 mg/cm$^2$, and
optional fourth layer:
in the range from 0.8 to 5 mg/cm$^2$.

In a further preferred embodiment, the layers of the controlled release systems having the above described application quantities comprises, preferably consists of:
optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm$^2$ to 1.5 mg/cm$^2$, based on the specific surface area of the starting core;
first layer: 82 to 84% (w/w) ethylcellulose (e.g. ethylcellulose N10) and 16 to 18% (w/w) triethyl citrate applied in the range from 2 mg/cm$^2$ to 6 mg/cm$^2$, based on the specific surface area of the starting core;
second layer: 13.5-15.5% (w/w) hydroxylpropyl cellulose (e.g.Klucel EF), 72-75% (w/w) flibanserin and 11-13% (w/w) talc applied in the range from 8 mg/cm$^2$ to 12 mg/cm$^2$, based on the specific surface area of the starting core;

third layer: 46-48.5% (w/w) ethylcellulose (e.g. ethylcellulose N10), 46-48.5% (w/w) hydroxypropyl methylcellulose (e.g. hypromellose E5) and 3-5.5% (w/w) triethyl citrate applied in the range from 0.8 mg/cm² to 1.5 mg/cm², based on the specific surface area of the starting core, fourth layer: 86-88% (w/w) Eudragit® L 100-55, 8-10% (w/w) talc and 3-5% (w/w) triethyl citrate applied in the range from 0.8 mg/cm² to 5 mg/cm², based on the specific surface area of the starting core.

In a further preferred embodiment, the layers of the controlled release systems having the above described application quantities comprises, preferably consists of:

optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm² to 1.5 mg/cm², based on the specific surface area of the starting core;

first layer: 82 to 84% (w/w) ethylcellulose (e.g. ethylcellulose N10) and 16 to 18% (w/w) triethyl citrate applied in the range from 2 mg/cm² to 6 mg/cm², based on the specific surface area of the starting core;

second layer: 13.5-15.5% (w/w) hydroxypropyl cellulose (e.g. Klucel EF), 72-75% (w/w) flibanserin and 11-13% (w/w) talc applied in the range from 8 mg/cm² to 12 mg/cm², based on the specific surface area of the starting core;

second insulating layer: 100% (w/w) hydroxypropyl methylcellulose (e.g. hypromellose E5), applied in the range from 0.2 mg/cm² to 1.5 mg/cm², based on the specific surface area of the starting core, third layer: 86-88% (w/w) Eudragit® L 100-55, 8-10% (w/w) talc and 3-5% (w/w) triethyl citrate applied in the range from 0.8 mg/cm² to 5.0 mg/cm², based on the specific surface area of the starting core.

In a further preferred embodiment, the layers of the controlled release systems having the above described application quantities comprises, preferably consists of:

optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm² to 1.5 mg/cm², based on the specific surface area of the starting core;

first layer: 82 to 84% (w/w) ethylcellulose (e.g. ethylcellulose N10) and 16 to 18% (w/w) triethyl citrate applied in the range from 2 mg/cm² to 6 mg/cm², based on the specific surface area of the starting core;

second layer: 13.5-15.5% (w/w) hydroxypropyl cellulose (e.g. Klucel EF), 72-75% (w/w) flibanserin and 11-13% (w/w) talc applied in the range from 8 mg/cm² to 12 mg/cm², based on the specific surface area of the starting core;

third layer: 46-48.5% (w/w) ethylcellulose (e.g. ethylcellulose N10), 46-48.5% (w/w) hydroxypropyl methylcellulose (e.g. hypromellose E5) and 3-5.5% (w/w) triethyl citrate applied in the range from 0.8 mg/cm² to 1.5 mg/cm², based on the specific surface area of the starting core, fourth layer: 70-72% (w/w) Eudragit® L 100-55, 15-20% (w/w) hydroxypropyl methylcellulose (e.g. hypromellose E5), 8-10% (w/w) talc and 3-5% (w/w) triethyl citrate applied in the range from 0.8 mg/cm² to 5 mg/cm², based on the specific surface area of the starting core.

In a further preferred embodiment, the layers of the controlled release systems having the above described application quantities comprises, preferably consists of:

optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm² to 1.5 mg/cm², based on the specific surface area of the starting core;

first layer: 82 to 84% (w/w) ethylcellulose (e.g. ethylcellulose N10) and 16 to 18% (w/w) triethyl citrate applied in the range from 2 mg/cm² to 6 mg/cm², based on the specific surface area of the starting core;

second layer: 13.5-15.5% (w/w) hydroxypropyl cellulose (e.g. Klucel EF), 72-75% (w/w) flibanserin and 11-13% (w/w) talc applied in the range from 8 mg/cm² to 12 mg/cm², based on the specific surface area of the starting core;

second insulating layer: 100% (w/w) hydroxypropyl methylcellulose (e.g. hypromellose E5), applied in the range from 0.2 mg/cm² to 1.5 mg/cm², based on the specific surface area of the starting core, third layer: 70-72% (w/w) Eudragit® L 100-55, 15-20% (w/w) hydroxypropyl methylcellulose (e.g. hypromellose E5), 8-10% (w/w) talc and 3-5% (w/w) triethyl citrate applied in the range from 0.8 mg/cm² to 5 mg/cm², based on the specific surface area of the starting core.

In a further preferred embodiment, the layers of the controlled release systems having the above described application quantities comprises, preferably consists of:

optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm² to 1.5 mg/cm², based on the specific surface area of the starting core;

first layer: 82 to 84% (w/w) ethylcellulose (e.g. ethylcellulose N10) and 16 to 18% (w/w) triethyl citrate applied in the range from 2 mg/cm² to 6 mg/cm², based on the specific surface area of the starting core;

second layer: 13.5-15.5% (w/w) hydroxypropyl cellulose (e.g. Klucel EF), 72-75% (w/w) flibanserin and 11-13% (w/w) talc applied in the range from 8 mg/cm² to 12 mg/cm², based on the specific surface area of the starting core;

third layer: 46-48.5% (w/w) ethylcellulose (e.g. ethylcellulose N10), 46-48.5% (w/w) hydroxypropyl cellulose (e.g. Klucel EF) and 3-5.5% (w/w) triethyl citrate applied in the range from 0.8 mg/cm² to 1.5 mg/cm², based on the specific surface area of the starting core, fourth layer: 70-72% (w/w) Eudragit® L 100-55, 15-20% (w/w) hydroxypropyl cellulose (e.g. Klucel EF), 8-10% (w/w) talc and 3-5% (w/w) triethyl citrate applied in the range from 0.8 mg/cm² to 5 mg/cm², based on the specific surface area of the starting core.

In a further preferred embodiment, the layers of the controlled release systems having the above described application quantities comprises, preferably consists of:

optional (first) insulating layer: 48 to 50% (w/w) hydroxypropyl methylcellulose (e.g. Pharmacoat 603), 48 to 50% (w/w) talc and 0.1 to 1.5% of anti-foaming agent (e.g. Dimeticon 350) applied in the range from 0.2 mg/cm² to 1.5 mg/cm², based on the specific surface area of the starting core;

first layer: 82 to 84% (w/w) ethylcellulose (e.g. ethylcellulose N10) and 16 to 18% (w/w) triethyl citrate applied in the range from 2 mg/cm² to 6 mg/cm², based on the specific surface area of the starting core;

second layer: 13.5-15.5% (w/w) hydroxypropyl cellulose (e.g. Klucel EF), 72-75% (w/w) flibanserin and 11-13% (w/w) talc applied in the range from 8 mg/cm² to 12 mg/cm², based on the specific surface area of the starting core;

second insulating layer: 100% (w/w) hydroxypropyl methylcellulose (e.g. hypromellose E5), applied in the range from 0.2 mg/cm² to 1.5 mg/cm², based on the specific surface area of the starting core, third layer: 70-72% (w/w) Eudragit® L 100-55, 15-20% (w/w) hydroxypropyl cellulose (e.g. Klucel EF), 8-10% (w/w) talc and 3-5% (w/w) triethyl citrate applied in the range from 0.8 mg/cm² to 5 mg/cm², based on the specific surface area of the starting core.

In a further preferred embodiment, the layers of the controlled release systems having the above described application quantities comprises, preferably consists of:

optional (first) insulating layer: 95 to 100% (w/w) hydroxypropyl methylcellulose (e.g. hypromellose E5) and 0 to 5% (w/w) applied in the range from 0.2 mg/cm² to 10.0 mg/cm², based on the specific surface area of the starting core;

first layer: 62 to 86% (w/w) Eudragit RS, 5 to 20% (w/w) triethyl citrate, 5 to 10% glycerol monostearate and 4 to 8% sodium sulphate applied in the range from 2 mg/cm² to 6 mg/cm², based on the specific surface area of the starting core;

second layer: 13.5-15.5% (w/w) hydroxylpropyl cellulose (e.g.Klucel EF), 72-75% (w/w) flibanserin and 11-13% (w/w) talc applied in the range from 8 mg/cm² to 12 mg/cm², based on the specific surface area of the starting core;

third layer: 63-72% (w/w) hydroxypropyl methylcellulose phthalate (e.g. HP 50), 20-25% (w/w) povidone (e.g. Kollidon 17), 4-6% glycerole monostearate and 4-6% (w/w) triethyl citrate applied in the range from 0.8 mg/cm² to 5 mg/cm², based on the specific surface area of the starting core.

The controlled release system of the present invention may be prepared according to conventionally known methods. The controlled release system may be prepared by the following method described hereinafter:

The core material containing the pH modifier may for example comprise crystals of the particular pH modifier(s) used or, more advantageously, roughly spherical particles of the desired size containing a defined amount of pH modifier(s), which can be produced by methods known and established in pharmaceutical technology. The core material may be produced, in particular, by pan methods, on pelleting plates or by extrusion/spheronisation. Then the core material thus obtained may be divided into fractions of the desired diameter by screening. Suitable core material has preferably an average diameter of 0.4 to 1.5 mm, preferably 0.6 to 0.8 mm.

Subsequently, the optional insulating layer may be applied to the core material. This can be done by conventional methods, e.g. by applying an aqueous solution or dispersion of the water-soluble, pharmaceutically acceptable polymer(s), optionally with the addition of plasticizers, separating agents and/or pigments and/or other suitable additives, in a fluidised bed, in coating pans or in a conventional layer coating apparatus. If necessary the product can then be screened again.

Thereafter, the first layer may be applied. This can be done by conventional methods, e.g. by applying a solution or dispersion (aqueous-based or organic-based) of the water-insoluble pharmaceutically acceptable polymer(s), optionally with the addition of suitable additives, in a fluidised bed, in a coating pans or in conventional layer coating apparatus. If necessary the product can then be screened again.

Then, flibanserin may be applied from a solution or dispersion preferably containing binder and optionally separating agent and/or other additives. The volatile solvent or dispersant is removed during or after the process by drying. The solvents or dispersants used in the process according to the present invention may be for example water, ethanol, isopropanol, acetone or mixtures of these solvents with one another. Emulsifiers or stabilizers may be present such as cetyl alcohol, Nonoxynol 100, oleic acid, polysorbates (polyethylene sorbitan fatty acid esters), sodium hydroxide, sodium lauryl sulphate, sorbic acid and the like.

The application of flibanserin to the core material may be carried out by established methods known in pharmaceutical technology, e.g. in coating pans, conventional layer coating apparatus or by the fluidised bed method. Then a further screening process may be carried out.

Subsequently a further optional (second) insulation layer may be provided on the second layer. Said insulating layer is composed as already described. This insulating layer may be present additionally or alternatively to the first insulating layer.

Afterwards the third layer can be produced by methods known and established in pharmaceutical technology. This can be done by conventional methods, e.g. by applying a dispersion of the pharmaceutically acceptable polymer(s) having anionic or no ionic groups, optionally with the addition of plasticizers and/or other suitable additives, in a fluidised bed, in coating pans or in a conventional layer coating apparatus. If necessary the product can then be screened again.

To reduce any increased abrasion during transfer into capsules and/or to increase the shelf life or in order to add a further diffusion barrier, the controlled release system may finally be coated with a coating (i.e. the optional fourth layer) preferably of a conventional pharmaceutical film forming agent, plasticizer and optionally pigment. This may be done by conventional methods.

The controlled release system of the present invention can be of any suitable size and shape, for example round, oval, polygonal or pillow-shaped, and optionally bear non-functional surface markings.

When core material with an average diameter of 0.4-1.5 mm is used, the process described above produces for example pellets containing flibanserin, which can then be packed into capsules. To do this, a number of these units corresponding to the required dosage may be packed into capsules in a standard capsule filling machine. Suitable hard capsules include, for example, hard gelatine capsules or hard capsules of hydroxypropyl methylcellulose (HPMC). Alternatively these units may be compressed together with suitable binders into tablets which disintegrate in the stomach releasing the coated pellets.

In case tablets or capsules are provided they may be packed in bottles or blisters well known in the art. Among such blisters are such being made of polyvinylchloride or polyvinylidene chloride. Aluminum-blisters are also possible. Bottles may be made of poylpropylene or polyethylene for example. Other conventional packaging materials are possible, too.

The controlled release systems of the invention, for example present in capsules or in another suitable dosage form, can be packaged in a container, accompanied by a package insert providing pertinent information such as, for example, dosage and administration information, contraindications, precautions, drug interactions and adverse reactions.

BRIEF DESCRIPTION OF THE DRAWINGS

In the drawings

FIG. 1 shows a schematic illustration of a preferred embodiment of the extended release system of the present invention, wherein the dosage form comprises or essentially consists of the active substance in form of flibanserin 20, at least one pH-dependent polymer 10, one or more pH modifier in form of at least one organic acid 30, and at least one pH-independent polymer 40. For the sake of clarity additives are omitted in FIG. 1. The extended release system according to the present invention may be considered to be a matrix type system which may be defined as well-mixed composite of ingredients fixed into a defined shape, preferably by tabletting. This intimate admixture of ingredients provides extended release of the active agent flibanserin 20 contained therein, although the pH value of the environment changes following administration.

FIGS. 2a and 2b show the function of a preferred embodiment of the extended release system of the present invention in schematic form after oral administration. FIG. 2a illustrates a low pH medium such as the environment in the stomach (pH about 1.2) and FIG. 2b illustrates a higher pH medium such as in the small intestine (pH 5-8), duodenum (pH 4-6.4), jejunum (pH 4-6.5) ileum (pH 6.5-8) and colon (pH 6-7.5).

"D" represents the diffusion layer and "DS" the drug substance, in the present case flibanserin. Usually, there exist two general flow directions, on one hand that of the aqueous medium, i.e. gastrointestinal juice, which diffuses into the extended release system of the present invention and on the other hand that of the drug substance which diffuses out of the extended release system. The dissolution of the drug substance is usually a function of the matrix porosity ($\epsilon$) and the drug substance solubility (L). If the matrix porosity and the solubility of the drug substance are raised the dissolution of the drug substance will increase.

Figure 1:
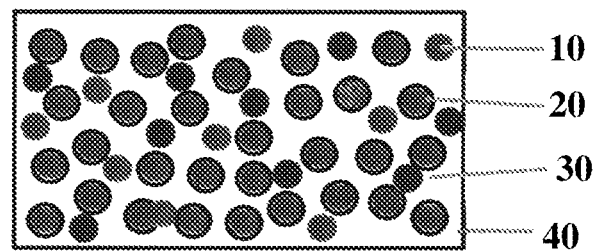
FIG. 1 shows a schematic illustration of a preferred embodiment of the extended release system according to the present invention.
Figure 2A:
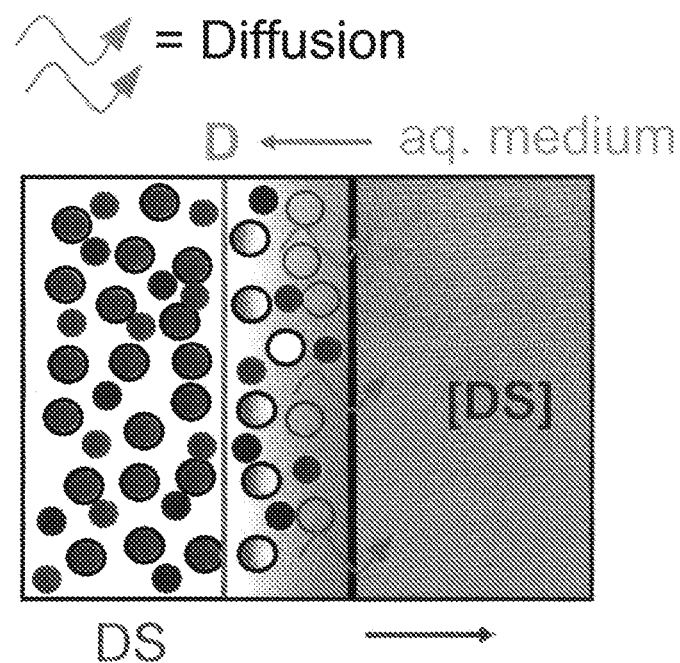
FIGS. 2a and 2b show the function of a preferred embodiment of the extended release system according to the present invention in schematic form.

In a low or acidic pH medium as shown in FIG. 2a (e.g. stomach) there exists a high solubility of the drug substance present so that a low porosity is desired. The pH-dependent polymer is insoluble in a low pH and represents a diffusion barrier for the aqueous media and the drug substance. The pH modifier being present is of less effectivity in an acidic pH medium.

Figure 2B:
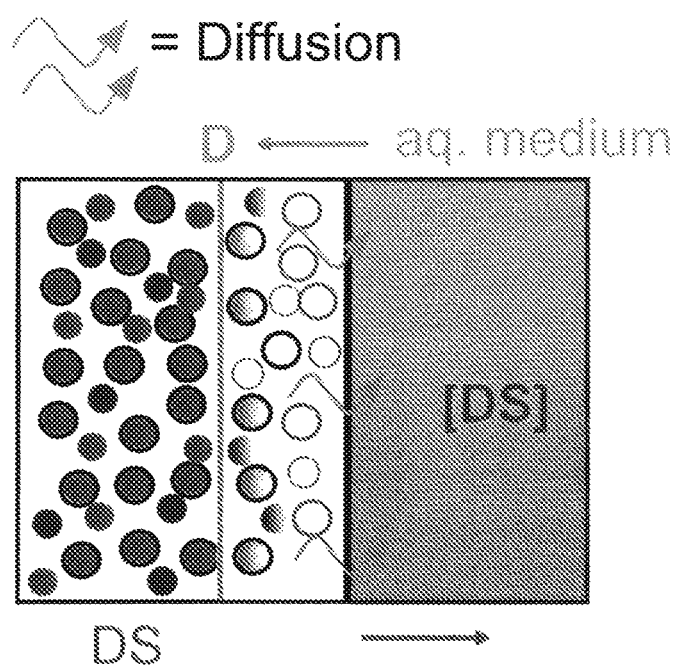

A higher pH medium as shown in FIG. 2b (e.g. intestine) provides a low solubility of the drug substance flibanserin. Therefore, the pH-dependent polymer which is soluble in the higher pH medium leads to a high porosity of the matrix system so that the release of the drug substance will be increased. Additionally the acid present supports the dissolution of the drug substance.

Therefore, the usual release capability of the aforementioned extended release matrix system is changed in such a manner to arrive at a practically independent pH release of the pH dependent soluble drug substance.

Figure 3:
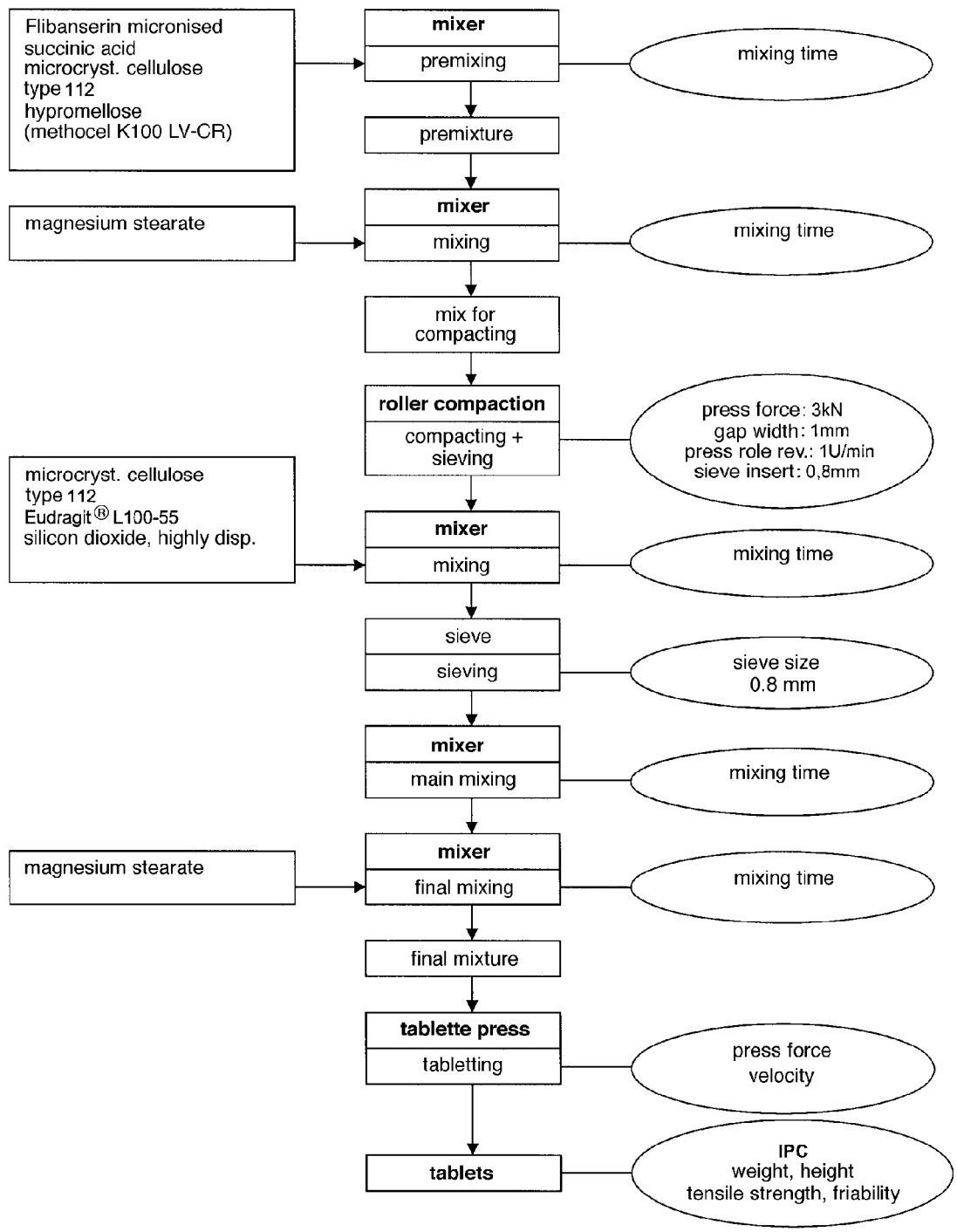
FIG. 3 represents a flow diagram illustrating a preferred method for the manufacturing of a preferred embodiment of the extended release system according to the present invention.

FIG. 3 will be described in detail in the Examples.

Figure 4:
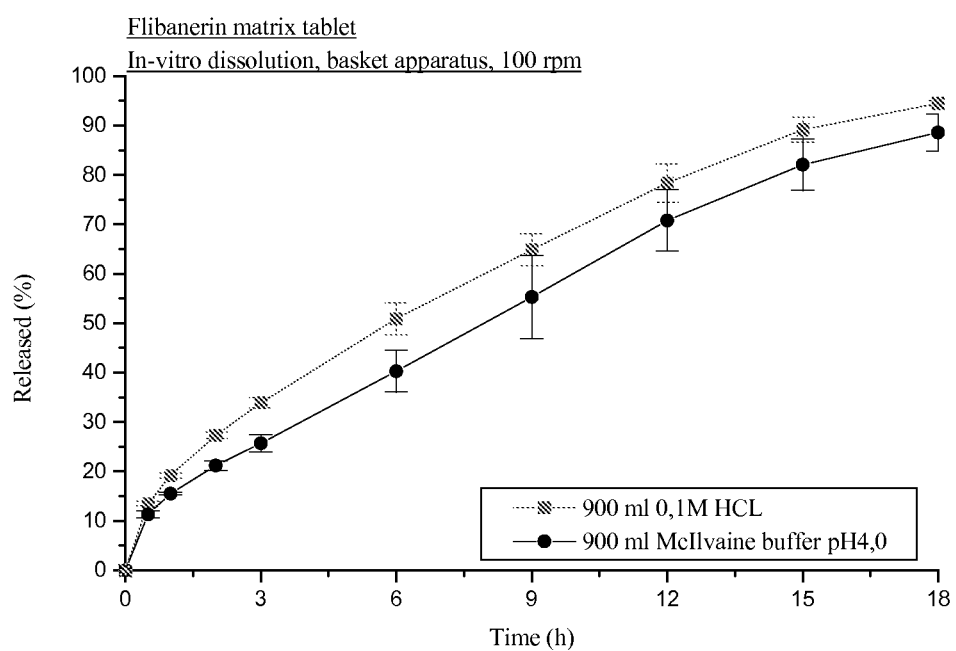
FIGS. 4 and 5 show in-vitro dissolution profiles of extended release formulations according to the present invention.

FIG. 4 shows in-vitro dissolution testing of example 1b conducted according to United States Pharmacopeia (USP) 28, chapter 711, using the same conditions and settings except for the composition and pH of the dissolution medium, which was varied between pH 1 and 4. Samples were taken after 0.5, 1, 2, 3, 6, 9, 12, 15 and 18 hours. In result, the average amount of drug released was comparable in both dissolution media at all time points.

Figure 5:
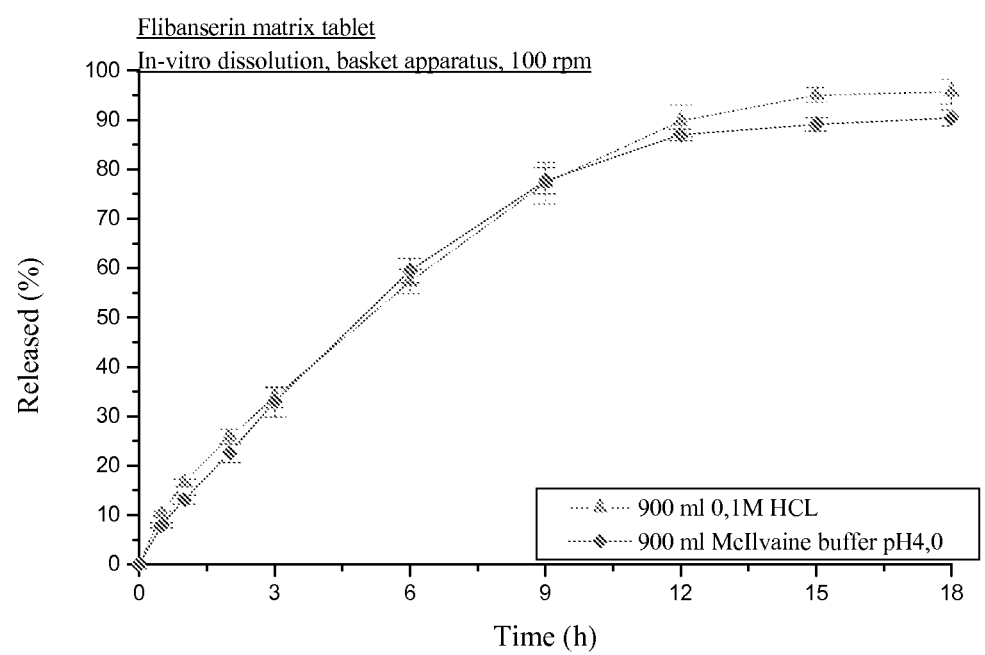

FIG. 5 shows in-vitro dissolution testing of example 1e conducted according to United States Pharmacopeia (USP) 28, chapter 711, using the same conditions and settings except for the composition and pH of the dissolution medium, which was varied between pH 1 and 4. Samples were taken after 0.5, 1, 2, 3, 6, 9, 12, 15 and 18 hours. In result, the average amount of drug released was comparable in both dissolution media at all time points.

Figure 6:
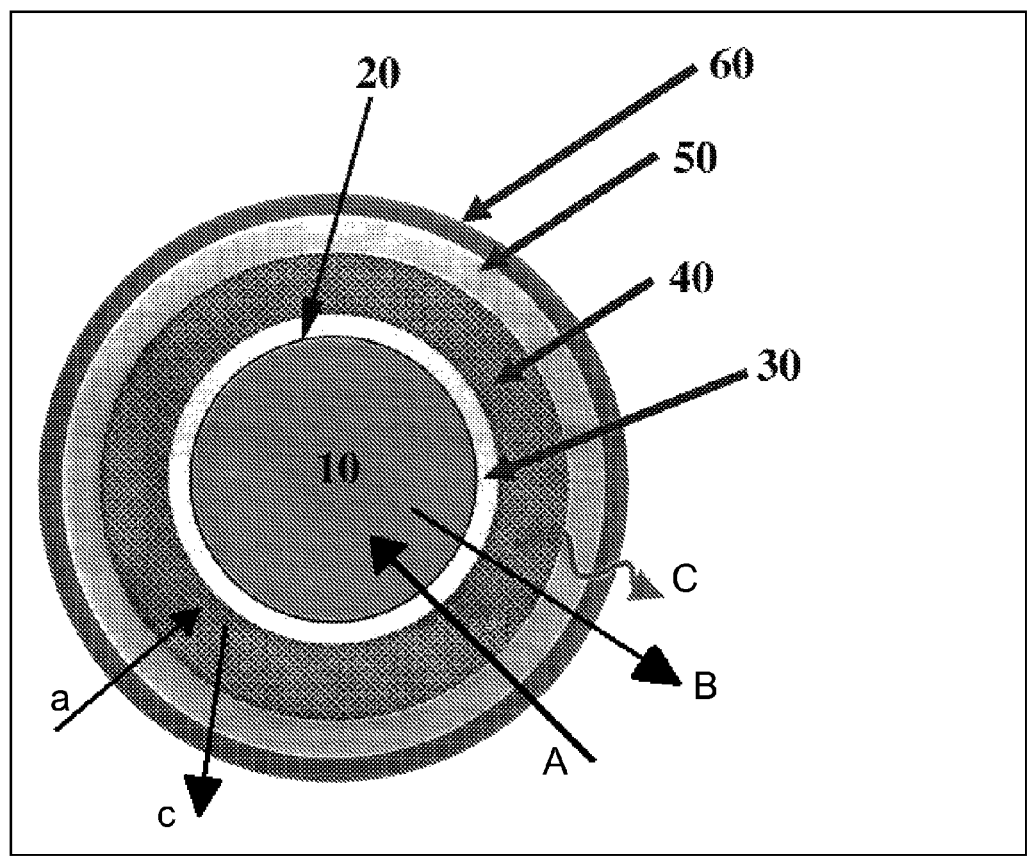
FIG. 6 shows a sectional schematic and enlarged view of a preferred embodiment of the controlled release system according to the present invention.

FIG. 6 shows a sectional schematic and enlarged view of a preferred embodiment of a controlled release system according to the present invention. The preferably bead-shaped/spherical core portion 10 contains or consists of one or more pharmaceutically acceptable organic acids and/or bases and/or buffers and optionally suitable excipients. This is optionally followed by a layer which separates the core 10 from the subsequent layers, the so-called insulating layer 20. The insulating layer 20 in turn, or the core material 10 in the absence of an insulating layer 20, is surrounded by a first layer 30 containing or consisting of one or more water-insoluble polymers and optional excipients, on which is applied the active substance layer 40, which are both preferably also spherical, which itself be surrounded by the third layer 50 containing or consisting of one or more polymers having no cationic groups in the molecules and optional excipients, on which one or more coatings 60 may be provided to increase the abrasion resistance and shelf life of the controlled release system of the present invention or to control the release of the active ingredient at low pH-values (e.g pH 1).

Further, the release of the controlled release system of the present invention is schematically represented in FIG. 6 by the gastric liquid (pH about 1), for example the fluid penetrates into the formulation (a) dissolving the active substance which for example might be a weak base. The release rate of the active substance is then controlled by the fourth layer (60) Moving into the small intestine the pH raises towards 6, thus for this example the fourth layer would be dissolved. The enteric liquid will penetrate the core hence, the dissolved pH modifier penetrates layer 1 (30) enhancing dissolution of the active substance at controlled pH (B), Finally, the third layer controls drug release.

FIGS. 7 to 19 will be described in detail in the Examples.

The invention described will now be illustrated by the following Examples. However, it is expressly pointed out that the Examples and description are intended solely as an illustration and should not be regarded as restricting the invention.

EXAMPLE 1

Extended Release Systems According to the Invention

In the following a preferably process to manufacture the extended release system of the present invention is exemplarily described. However, the process steps are not intended to be of limitative character at all.

The following process steps are illustrated in the flow chart shown in FIG. 3.

The preparation of the extended release system of the present invention in the following Example usually takes place over 7 steps:

step 1): preparation of the pre-mixture;
step 2): preparation of the mixture for compaction;
step 3): performing roller compaction;
step 4): preparation of the admixture;
step 5): preparation of the main mixture;
step 6): preparation of the final mixture; and
step 7): preparation of the tablets.

The steps will be described in the following in detail:

1. Pre-Mixture

To active substance flibanserin (200.00 g) pre-sieved (sieve size 0.5 mm) succinic acid (100.00 g), hypromellose (200.00 g) and microcrystalline cellulose (215.00 g) are added and mixed in a usual blender or mixer for 5 minutes.

2. Mixture for Compaction

To the pre-mixture obtained in above step 1 pre-sieved (sieve size 0.5 mm) magnesium stearate of herbal origin (5.00 g) is added and blended in a usual blender or mixer for 3 minutes.

3. Roller Compaction

The mixture obtained in above step 2 is subjected to a roller compaction process step as known to the skilled in the art.

4. Admixture

To the compacted mixture obtained in step 3, microcrystalline cellulose (215.00 g), Eudragit® L 100-55 (50.00 g) and highly disperse silicon dioxide (pre-sieved, sieve size 0.5 mm; 5.00 g) are added and blended for 5 minutes. Subsequently the obtained mixture is sieved (sieve size 0.8 mm).

5. Main Mixture

The admixture obtained in step 4 is again blended for further 5 minutes.

6. Final Mixture

To the main mixture obtained above in step 5 pre-sieved (sieve size 0.5 mm) magnesium stearate of herbal origin (10.00 g) is added and blended for 3 minutes.

7. Tablets

In a suitable tablet pressing apparatus the final mixture as obtained above in step 6 is pressed to obtain the desired tablets. In Process Controls (IPC) are employed as usual.

According to the aforementioned process the following tablets may be prepared:

EXAMPLE 1A

| Ingredient | [mg/tablet] |
| --- | --- |
| Flibanserin, micronised | 100.000 |
| Hydroxypropylcellulose | 100.000 |
| Microcrystalline cellulose | 215.000 |
| Succinic acid | 50.000 |
| Methacrylic acid-ethyl acrylate copolymer (1:1) | 25.000 |
| Silica, colloidal anhydrous | 2.500 |
| Magnesium stearate | 7.500 |
| Total | 500.000 |

EXAMPLE 1B

| Ingredient | [mg/tablet] |
| --- | --- |
| Flibanserin, micronised | 100.000 |
| Hypromellose 2208 | 100.000 |
| Microcrystalline cellulose | 215.000 |
| Succinic acid | 50.000 |
| Methacrylic acid-ethyl acrylate copolymer (1:1) | 25.000 |
| Silica, colloidal anhydrous | 2.500 |
| Magnesium stearate | 7.500 |
| Total | 500.000 |

EXAMPLE 1C

| Ingredient | [mg/tablet] |
| --- | --- |
| Flibanserin, micronised | 100.000 |
| Hypromellose 2208 | 100.000 |
| Microcrystalline cellulose | 115.000 |
| Tartaric acid | 100.000 |
| Fumaric acid | 50.000 |
| Methacrylic acid-ethyl acrylate copolymer (1:1) | 25.000 |
| Silica, colloidal anhydrous | 2.500 |
| Magnesium stearate | 7.500 |
| Total | 500.000 |

EXAMPLE 1D

| Ingredient | [mg/tablet] |
| --- | --- |
| Flibanserin, micronised | 100.000 |
| Hydroxypropylcellulose | 100.000 |
| Microcrystalline cellulose | 115.000 |
| Tartaric acid | 100.000 |
| Fumaric acid | 50.000 |
| Methacrylic acid-ethyl acrylate copolymer (1:1) | 25.000 |
| Silica, colloidal anhydrous | 2.500 |
| Magnesium stearate | 7.500 |
| Total | 500.000 |

EXAMPLE 1E

| Ingredient | [mg/tablet] |
|---|---|
| Flibanserin, micronised | 100.000 |
| Hydroxypropylcellulose | 100.000 |
| Hypromellose 2208 | 50.000 |
| Microcrystalline cellulose | 165.000 |
| Succinic acid | 50.000 |
| Methacrylic acid-ethyl acrylate copolymer (1:1) | 25.000 |
| Silica, colloidal anhydrous | 2.500 |
| Magnesium stearate | 7.500 |
| Total | 500.000 |

EXAMPLE 1F

| Ingredient | [mg/tablet] |
|---|---|
| Flibanserin, micronised | 100.000 |
| Hypromellose 2208 | 100.000 |
| Microcrystalline cellulose | 115.000 |
| Lactose monohydrate | 100.000 |
| Succinic acid | 50.000 |
| Methacrylic acid-ethyl acrylate copolymer (1:1) | 25.000 |
| Silica, colloidal anhydrous | 2.500 |
| Magnesium stearate | 7.500 |
| Total | 500.000 |

EXAMPLE 1G

| Ingredient | [mg/tablet] |
|---|---|
| Flibanserin, micronised | 100.000 |
| Hypromellose 2910 | 200.000 |
| Microcrystalline cellulose | 90.000 |
| Succinic acid | 50.000 |
| Carbomer 941 | 50.000 |
| Silica, colloidal anhydrous | 2.500 |
| Magnesium stearate | 7.500 |
| Total | 500.000 |

EXAMPLE 1H

| Ingredient | [mg/tablet] |
|---|---|
| Flibanserin, micronised | 100.000 |
| Hydroxypropylcellulose | 200.000 |
| Microcrystalline cellulose | 90.000 |
| Succinic acid | 50.000 |
| Carbomer 941 | 50.000 |
| Silica, colloidal anhydrous | 2.500 |
| Magnesium stearate | 7.500 |
| Total | 500.000 |

EXAMPLE 1I

| Ingredient | [mg/tablet] |
|---|---|
| Flibanserin, micronised | 100.000 |
| Hypromellose 2910 | 100.000 |
| Hydroxypropylcellulose | 100.000 |
| Microcrystalline cellulose | 90.000 |
| Succinic acid | 50.000 |
| Methacrylic acid-ethyl acrylate copolymer (1:1) | 50.000 |
| Silica, colloidal anhydrous | 2.500 |
| Magnesium stearate | 7.500 |
| Total | 500.000 |

EXAMPLE 1J

| Ingredient | [mg/tablet] |
|---|---|
| Flibanserin, micronised | 100.000 |
| Hypromellose 2208 | 100.000 |
| Microcrystalline cellulose | 215.000 |
| Succinic acid | 50.000 |
| Sodium alginate | 25.000 |
| Silica, colloidal anhydrous | 2.500 |
| Magnesium stearate | 7.500 |
| Total | 500.000 |

EXAMPLE 1K

| Ingredient | [mg/tablet] |
|---|---|
| Flibanserin, micronised | 100.000 |
| Hydroxypropylcellulose | 85.000 |
| Hypromellose 2208 | 42.500 |
| Microcrystalline cellulose | 117.750 |
| Succinic acid | 50.000 |
| Methacrylic acid-ethyl acrylate copolymer (1:1) | 21.250 |
| Silica, colloidal anhydrous | 2.125 |
| Magnesium stearate | 6.375 |
| Total | 425.000 |

EXAMPLE 1L

| Ingredient | [mg/tablet] |
|---|---|
| Flibanserin, micronised | 100.000 |
| Hydroxypropylcellulose | 85.000 |
| Methylcellulose | 42.500 |
| Microcrystalline cellulose | 117.750 |
| Succinic acid | 50.000 |
| Methacrylic acid-ethyl acrylate copolymer (1:1) | 21.250 |
| Silica, colloidal anhydrous | 2.125 |
| Magnesium stearate | 6.375 |
| Total | 425.000 |

EXAMPLE 1M

| Ingredient | [mg/tablet] |
| --- | --- |
| Flibanserin, micronised | 100.000 |
| Hydroxypropylcellulose | 85.000 |
| Methylcellulose | 42.500 |
| Microcrystalline cellulose | 117.750 |
| Tartaric acid | 50.000 |
| Methacrylic acid-ethyl acrylate copolymer (1:1) | 21.250 |
| Silica, colloidal anhydrous | 2.125 |
| Magnesium stearate | 6.375 |
| Total | 425.000 |

EXAMPLE 1N

| Ingredient | [mg/tablet] |
| --- | --- |
| Flibanserin, micronised | 100.000 |
| Hydroxypropylcellulose | 85.000 |
| Hypromellose 2208 | 42.500 |
| Microcrystalline cellulose | 117.750 |
| Tartaric acid | 50.000 |
| Methacrylic acid-ethyl acrylate copolymer (1:1) | 21.250 |
| Silica, colloidal anhydrous | 2.125 |
| Magnesium stearate | 6.375 |
| Total | 425.000 |

EXAMPLE 1O

| Ingredient | [mg/tablet] |
| --- | --- |
| Flibanserin, micronised | 75.000 |
| Hypromellose 2208 | 75.000 |
| Microcrystalline cellulose | 161.250 |
| Succinic acid | 37.500 |
| Methacrylic acid-ethyl acrylate copolymer (1:1) | 18.750 |
| Silica, colloidal anhydrous | 1.875 |
| Magnesium stearate | 5.625 |
| $1^{st}$ layer | 375.000 |
| Flibanserin micronised | 25.000 |
| Lactose fine sieved | 71.720 |
| Microcrystalline cellulose | 23.905 |
| Hypromellose 2910 | 1.250 |
| Croscarmellose sodium | 2.500 |
| Magnesium stearate | 0.625 |
| $2^{nd}$ layer | 125.000 |
| Total | 500.000 |

EXAMPLE 1P

| Ingredient | [mg/tablet] |
| --- | --- |
| Flibanserin, micronised | 75.000 |
| Hydroxypropylcellulose | 75.000 |
| Hypromellose 2208 | 37.500 |
| Microcrystalline cellulose | 123.750 |
| Succinic acid | 37.500 |
| Methacrylic acid-ethyl acrylate copolymer (1:1) | 18.750 |
| Silica, colloidal anhydrous | 1.875 |
| Magnesium stearate | 5.625 |
| $1^{st}$ layer | 375.000 |
| Flibanserin micronised | 25.000 |
| Lactose fine sieved | 71.720 |
| Microcrystalline cellulose | 23.905 |
| Hypromellose 2910 | 1.250 |
| Croscarmellose sodium | 2.500 |
| Magnesium stearate | 0.625 |
| $2^{nd}$ layer | 125.000 |
| Total | 500.000 |

EXAMPLE 2

Controlled Release Systems According to the Invention

EXAMPLE 2.1

In the following a preferable process to manufacture the controlled release system of the present invention is exemplarily described. However, the process steps are not intended to be of limitative character at all.

The preparation of the controlled release system of the present invention in the following Example usually takes place over 6 steps:

step a): preparation of core material containing pH modifier;
step b): preparation of the first layer;
step c): preparation of the second layer containing active substance;
step d): preparation of the third layer;
step e): preparation of the fourth layer; and
step f): packing into capsules.

The steps will be described in the following in detail:
Step a)
Preparation of Core Material Containing pH Modifier a1) 1 part by weight of gum arabic is dissolved with stirring in 4 parts by weight of purified water at 50° C. 5 parts by weight of tartaric acid are then dissolved in this solution with stirring.

8.3 parts by weight of tartaric acid crystals with an average particle size of 0.4 to 0.6 mm are placed in a suitable coating apparatus fitted with an air inlet and exhaust and the container is set rotating. At an air inlet temperature of 60°-80° C. The tartaric acid crystals are sprayed with the solution of tartaric acid-gum arabic in intermittent operation and sprinkled with a total of 6.7 parts by weight of powdered tartaric acid, so as to produce roughly spherical particles.

The spherical tartaric acid core material is then dried in the rotating container at an air inlet temperature of 60°-80° C.

The core material is fractionated using a tumbler screening machine with perforated plates having nominal mesh sizes of 0.6 and 0.8 mm. The product fraction of between 0.6 and 0.8 mm is used in subsequent processing.

a2) Isolation of the Core Material Containing Tartaric Acid 0.5 parts of hyprmellose are dissolved in 10.1 parts of 96% ethanol. Further 0.5 parts of talc together with 0.01 parts of polydimethylsiloxane are dispersed into the hypromellose/ethanol solution with stirring. This insulating dispersion is sprayed onto the tartaric acid cores (a1) in a fluidised bed processing plant, 21 parts by weight of tartaric acid-containing core material are sprayed with the hypromellose/talc dispersion at an air entry temperature of 35°-40° C. by the under-bed spraying method. The isolated tartaric acid-containing core material is then dried in the circulating air dryer at 40° C. for 8 hours. To remove lumps the dried isolated tartaric acid-containing core material is screened through a screen with a nominal mesh size of 1.0 mm. The fraction of material (particle size less than 1 mm) is further processed.

The other steps b) to f) are illustrated in flow diagrams shown in FIGS. 7 to 11.

Step b)

Preparation of the First Layer

Figure 7:
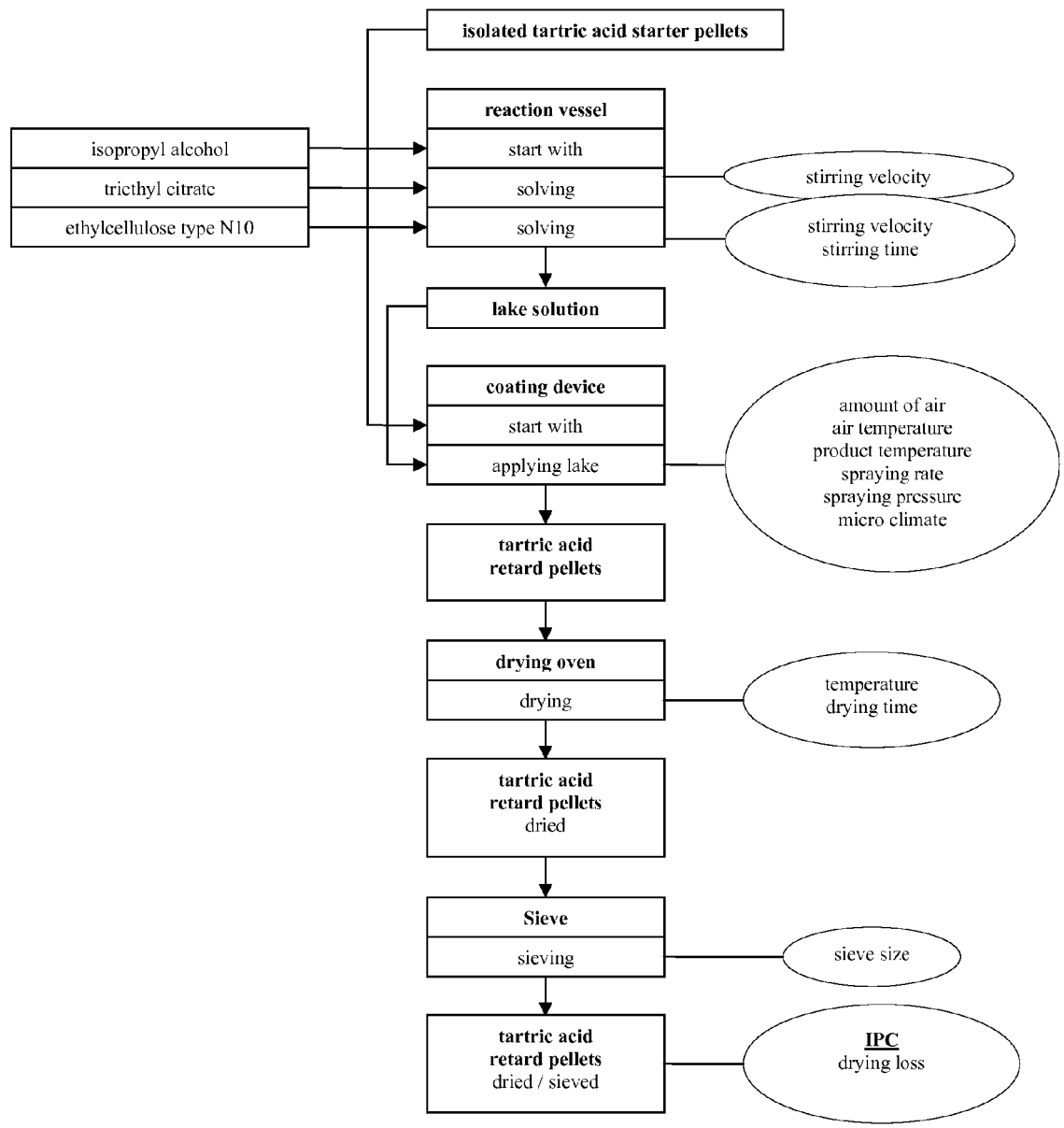
FIGS. 7 to 18 represent flow diagrams illustrating a preferred method for the manufacturing of the controlled release system according to the present invention.

As illustrated in FIG. 7 it may be started with a core material prepared as described above, for example a core material containing tartaric acid, the first layer was subsequently prepared as follows:

1. Preparation of the Lake Solution

Isopropyl alcohol (4730.00 g) was charged in a suitable reaction vessel and then triethyl citrate (45.00 g) and ethylcellulose type N10 (225.00 g) were added in portions and dispersed in this solution with stirring. The solution was stirred at room temperature overnight. It was obtained a lake solution.

2. Spraying of the Obtained Lake Solution

Then the obtained lake solution was sprayed onto 1500 g of tartaric starter pellets (insulated). To this purpose the pellets were placed in a suitable coating apparatus fitted with an air inlet and exhaust. At an air inlet temperature of about 45° C. the tartaric pellets were sprayed with the lake solution in continuous operation so as to produce roughly spherical particles. The following conditions were used:

| inlet air quantity | 100 m³/h |
|---|---|
| spraying rate | 2-18 g/min |
| spray pressure | 0.6 bar, |
| micro climate | 0.2 bar |
| nozzle diameter | 1.2 mm |
| spray time | about 7 h |
| product temperature | 30-40° C. |

The virtually spherical product obtained was then dried in a suitable drying device at 40° C. for 12 hours. The product was fractionated using a suitable screening machine with perforated plates having nominal mesh sizes of 1.0 mm.

Step c)

Preparation of the Second Layer Containing the Active Substance

1. Preparation of the Lake Solution

Figure 8:
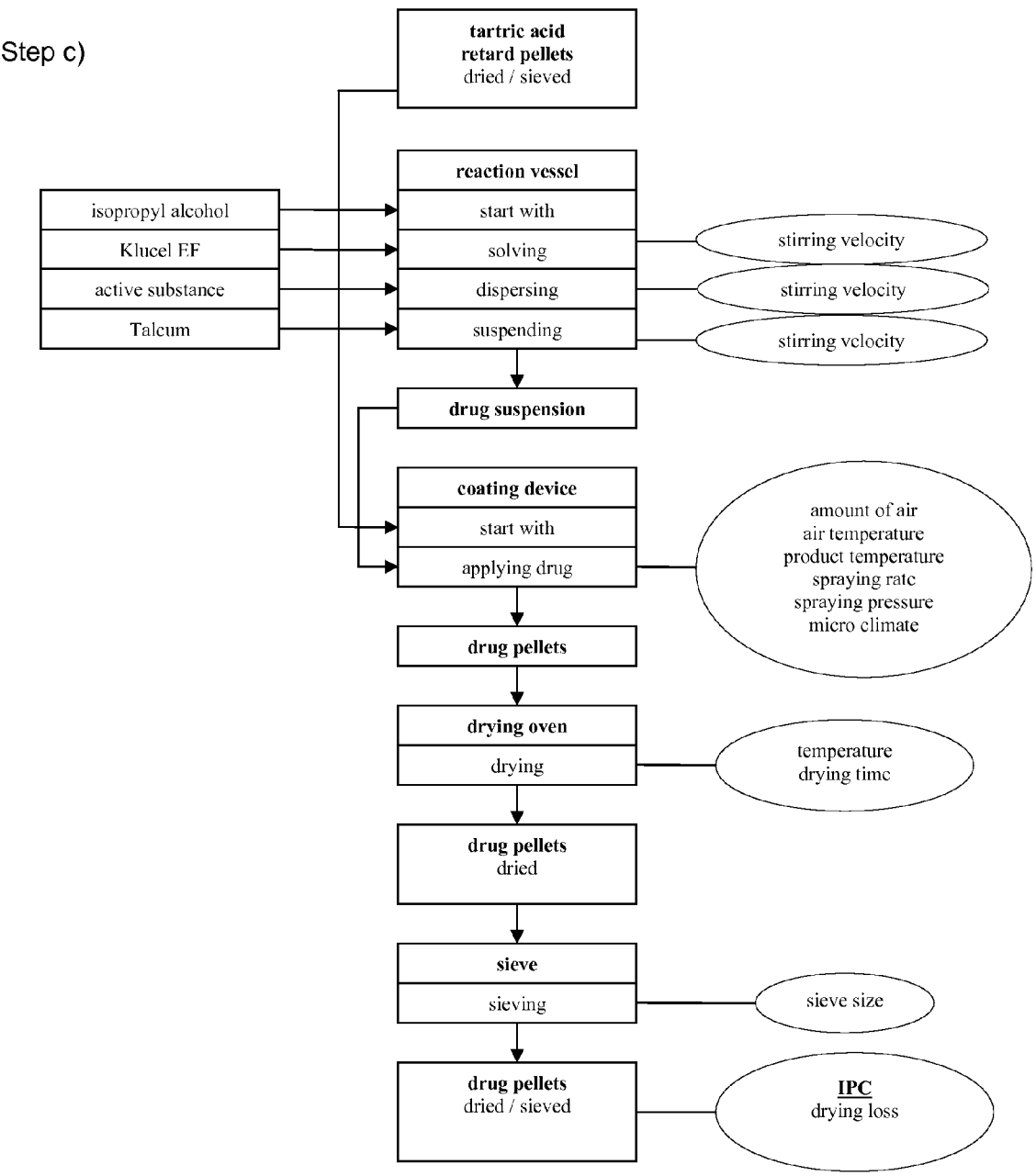

As illustrated in FIG. 8 isopropyl alcohol (1360.00 g) was charged in a suitable reaction vessel and then Klucel EF (binder; 50.00 g), and flibanserin (250.00 g) added in portions and talc (40.00 g) were dispersed in this solution with stirring. The solution was stirred at room temperature overnight. It was obtained a lake solution.

2. Spraying of the Obtained Lake Solution

Then the lake solution was sprayed onto 778 g of the product obtained in step b). To this purpose the product was placed in a suitable coating apparatus fitted with an air inlet and exhaust. At an air inlet temperature of about 25° C. the product was sprayed with the lake solution in continuous operation and sprinkled so as to produce roughly spherical particles. The following conditions were used:

| inlet air quantity | 100 m³/h |
|---|---|
| spraying rate | 1-10 g/min |
| spray pressure | 0.6 bar, |
| micro climate | 0.2 bar |
| nozzle diameter | 1.2 mm |
| spray time | about 5 h |
| product temperature | 20-25° C. |

The virtually spherical product obtained was then dried in a suitable drying device at 40° C. for 12 hours. The product was fractionated using a suitable screening machine with perforated plates having nominal mesh sizes of 1.25 mm.

Step d)

Preparation of the Third Layer

1. Preparation of the Lake Solution

Figure 9:
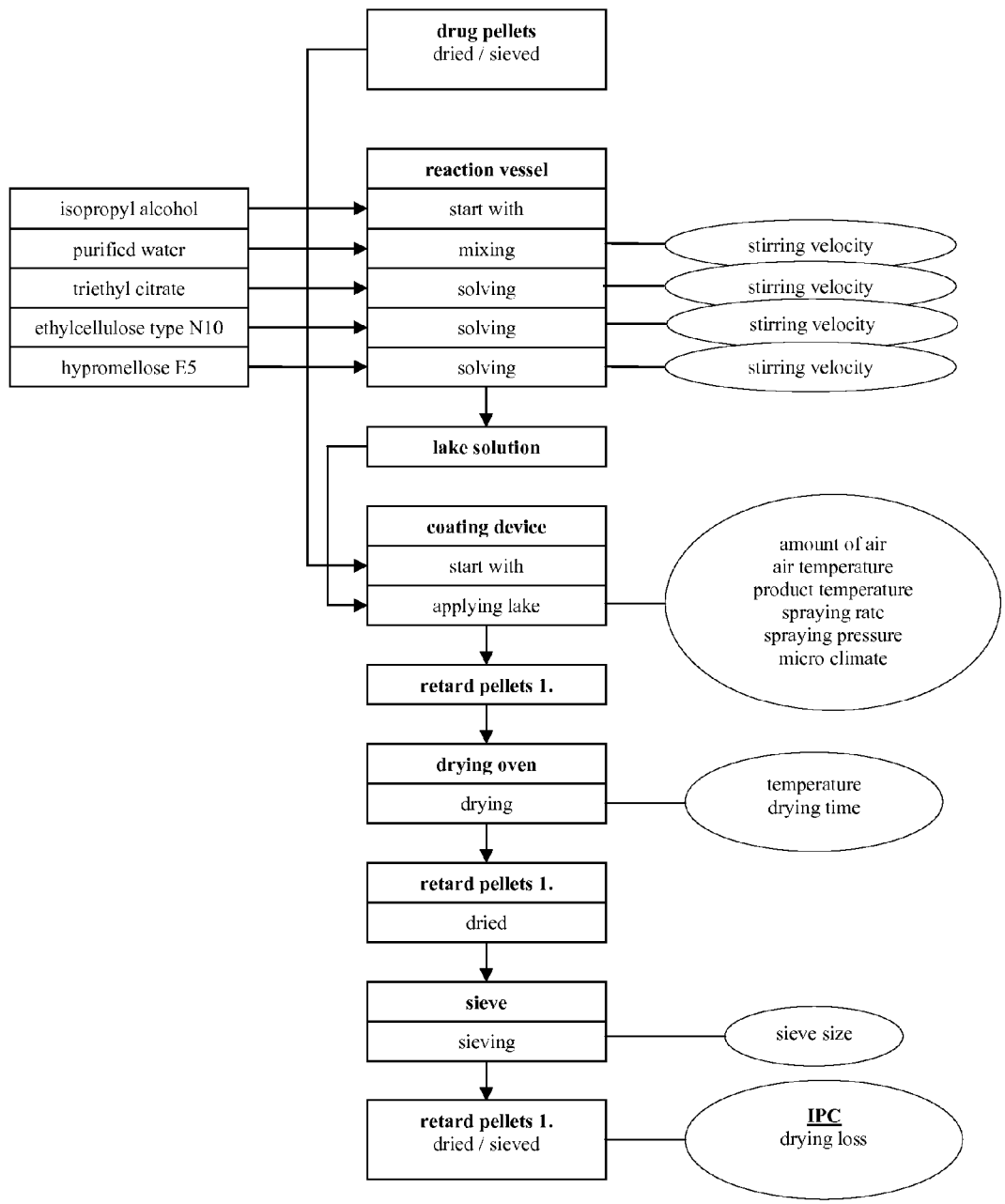

As illustrated in FIG. 9 isopropyl alcohol (421.70 g) was charged in a suitable reaction vessel and then purified water (74.42 g), triethyl citrate (1.65 g), ethylcellulose type N10 (16.50 g) and hypromellose (Methocel E5, 16.50 g) were added in portions and dispersed in this solution with stirring. The solution was stirred at room temperature overnight. It was obtained a lake solution.

2. Spraying of the Obtained Lake Solution

Then the lake solution was sprayed onto 1100 g of the product obtained in step c). To this purpose the pellets were placed in a suitable coating apparatus fitted with an air inlet and exhaust. At an air inlet temperature of about 35° C. the product was sprayed with the lake solution in continuous operation and sprinkled so as to produce roughly spherical particles. The following conditions were used:

| inlet air quantity | 70 m³/h |
|---|---|
| spraying rate | 2-6 g/min |
| spray pressure | 0.6 bar, |
| micro climate | 0.2 bar |
| nozzle diameter | 1.2 mm |
| spray time | about 4 h |
| product temperature | 30-35° C. |

The virtually spherical product obtained was then dried in a suitable drying device at 40° C. for 12 hours. The product was fractionated using a suitable screening machine with perforated plates having nominal mesh sizes of 1.25 mm.

Step e)

Preparation of the Fourth Layer

1. Preparation of the Lake Solution

Figure 10:
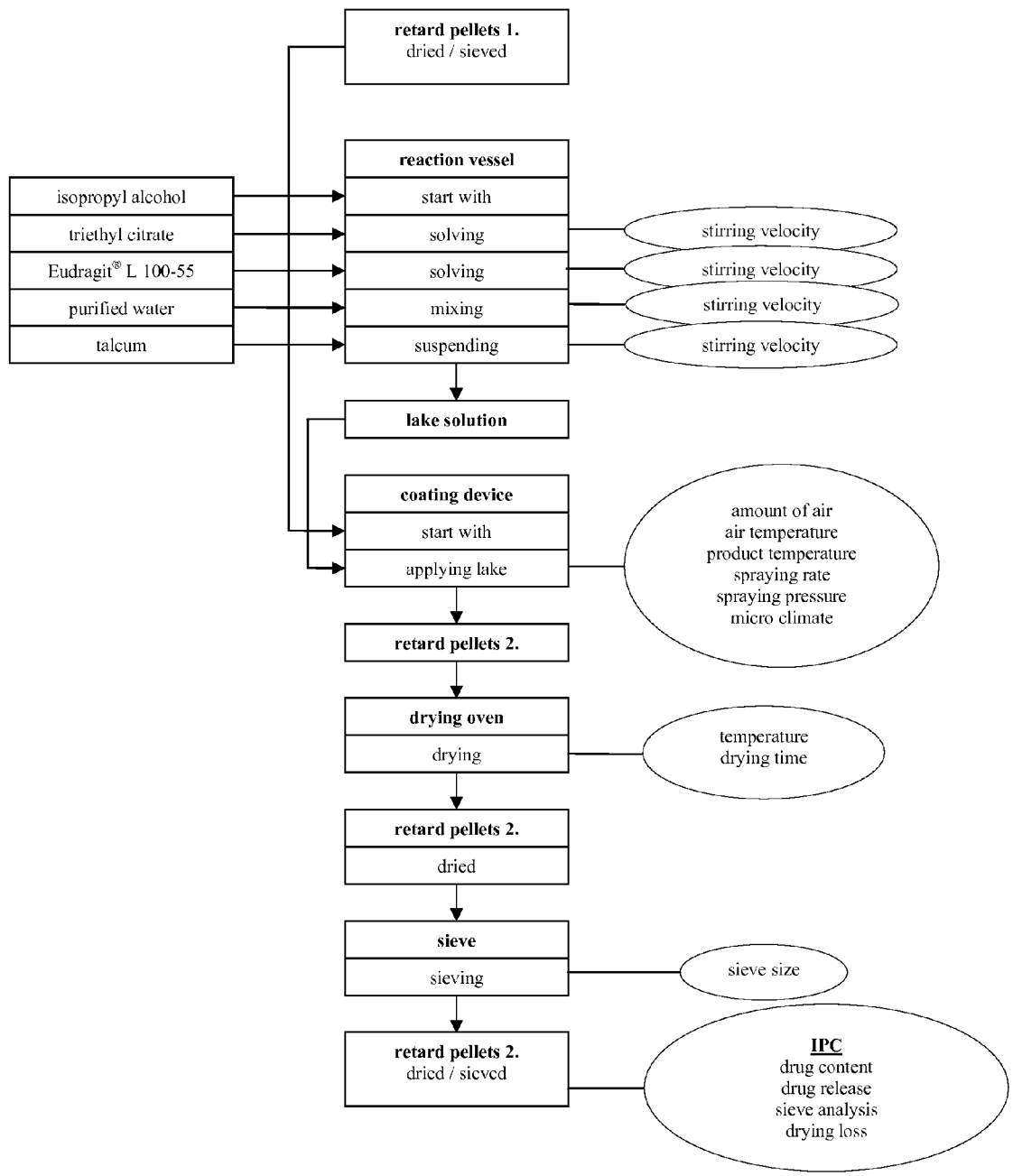

As illustrated in FIG. 10 isopropyl alcohol (341.36 g) was charged in a suitable reaction vessel and then triethyl citrate (1.25 g), Eudragit® L 100-55 (25.00 g) and purified water (46.550 g) were added in portions and dispersed in this solution with stirring. The solution was stirred at room temperature overnight. It was obtained a lake solution.

2. Spraying of the Obtained Lake Solution

Then talc (2.50 g) was suspended into the lake solution which was subsequently sprayed onto 1000.0 g of the product obtained in step d). To this purpose the pellets were placed in a suitable coating apparatus fitted with an air inlet and exhaust. At an air inlet temperature of about 35° C. the product was sprayed with the lake solution in continuous operation and sprinkled so as to produce roughly spherical particles. The following conditions were used:

| | |
|---|---|
| inlet air quantity | 70 m³/h |
| spraying rate | 2-6 g/min |
| spray pressure | 0.6 bar, |
| micro climate | 0.2 bar |
| nozzle diameter | 1.2 mm |
| spray time | about 3 h |
| product temperature | 30-35° C. |

The virtually spherical product obtained was then dried in a suitable drying device at 25° C. for 12 hours. The product was fractionated using a suitable screening machine with perforated plates having nominal mesh sizes of 1.25 mm.

Step f)

Packing into Capsules

Figure 11:
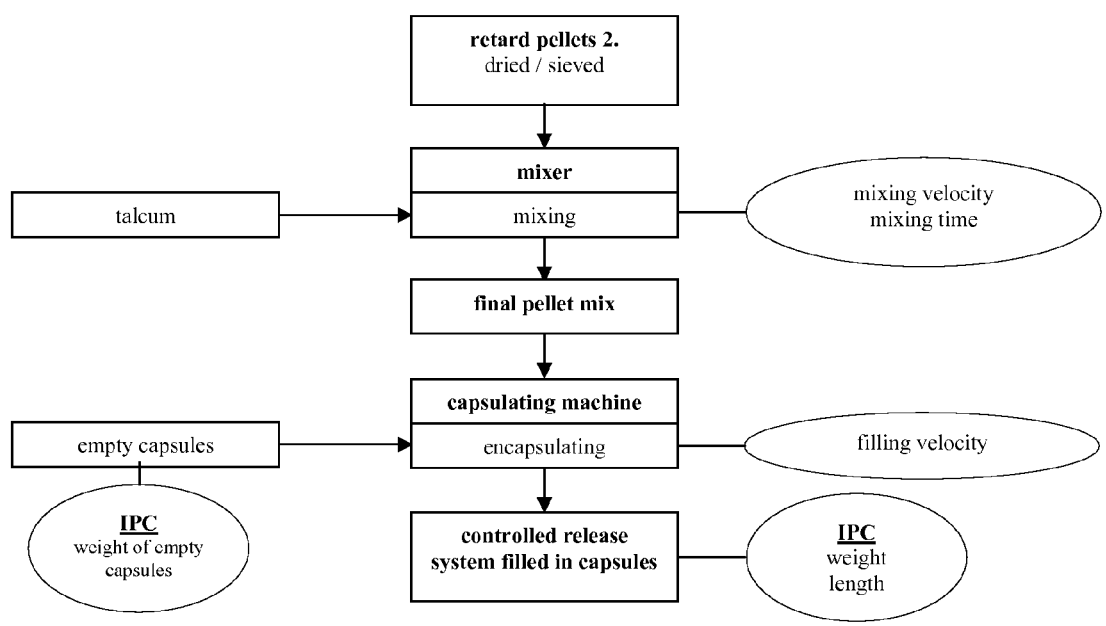

As illustrated in FIG. 11 a quantity of pellets containing active substance was mixed with talc to obtain the final mixture which was subsequently packed into size capsules such as hard gelatine capsules size 0 using a capsule filling machine.

During or after any step usual Internal Process Controls (IPC) were employed.

EXAMPLE 2.2

The preparation of the controlled release system of the present invention in the following Example usually takes place over 6 steps:

step a): preparation of core material containing pH modifier;

step b): preparation of the first layer;

step c): preparation of the second layer containing flibanserin;

step d): preparation of an insulating layer;

step e): preparation of the third layer; and step f): packing into capsules.

The same process steps a), b) and c) were performed as described above in Example 1. Then the process was continued as follows:

step d)

Insulating Layer

1. Preparation of the Lake Solution

Figure 12:
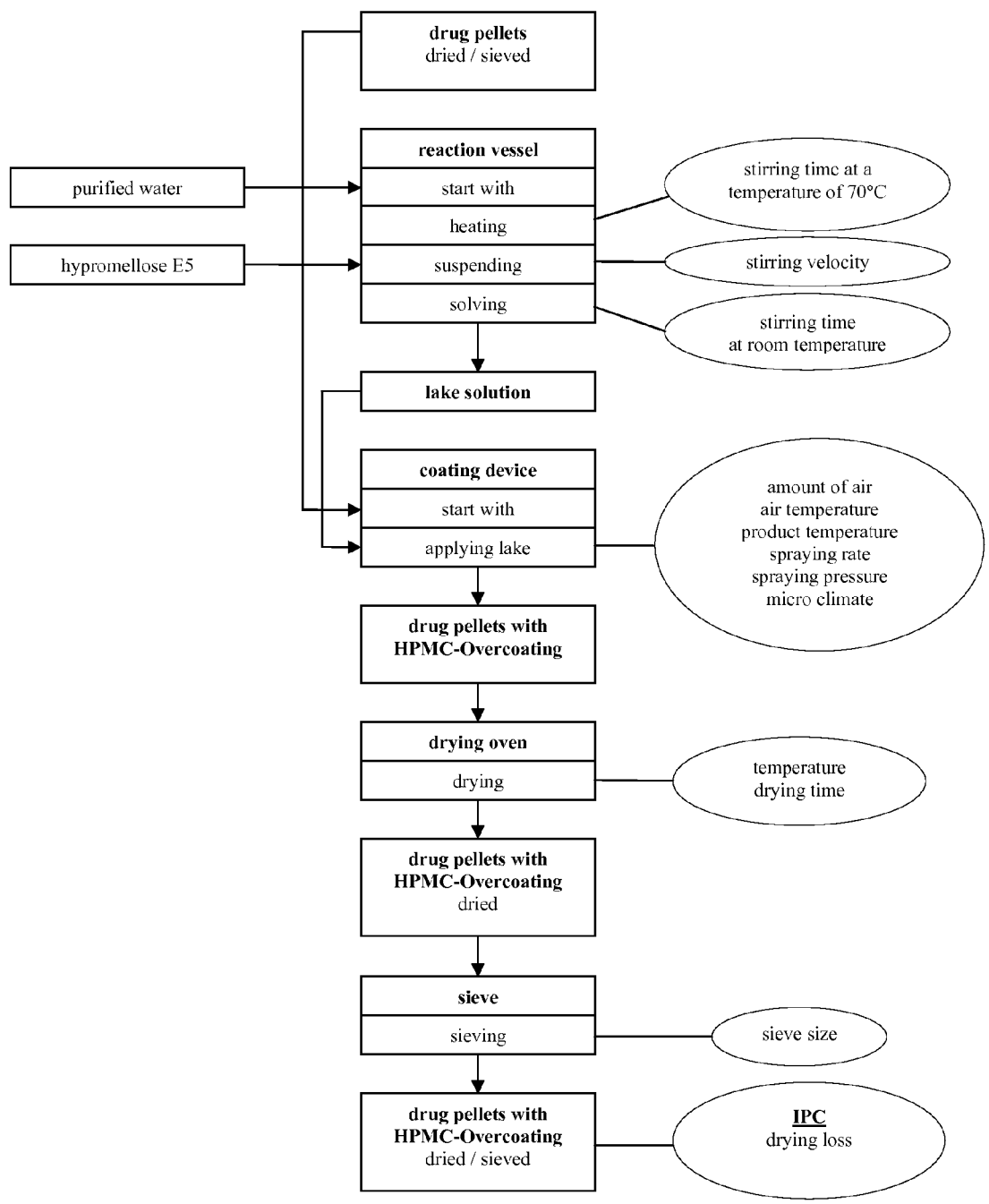

As illustrated in FIG. 12 purified water (466.88 g) was charged in a suitable reaction vessel and then hypromellose (Methocel E5) (22.00 g) at a temperature of 70 to 75° C. added in portions and dispersed in this solution with stirring. The solution was cooled and stirred at room temperature overnight. It was obtained a lake solution.

2. Spraying of the Obtained Lake Solution

Then the lake solution was sprayed onto 1100.0 g of the product obtained in step c). To this purpose the pellets were placed in a suitable coating apparatus fitted with an air inlet and exhaust. At an air inlet temperature of about 40° C. the product was sprayed with the lake solution in continuous operation and sprinkled so as to produce roughly spherical particles. The following conditions were used:

| | |
|---|---|
| inlet air quantity | 70 m³/h |
| spraying rate | 1-6 g/min |
| spray pressure | 0.6 bar, |
| micro climate | 0.2 bar |
| nozzle diameter | 1.2 mm |
| spray time | about 3 h |
| product temperature | 30-35° C. |

The virtually spherical product obtained was then dried in a suitable drying device at 40° C. for 12 hours. The product was fractionated using a suitable screening machine with perforated plates having nominal mesh sizes of 1.25 mm.

Step e)

Preparation of the Third Layer

1. Preparation of the Lake Solution

Figure 13:
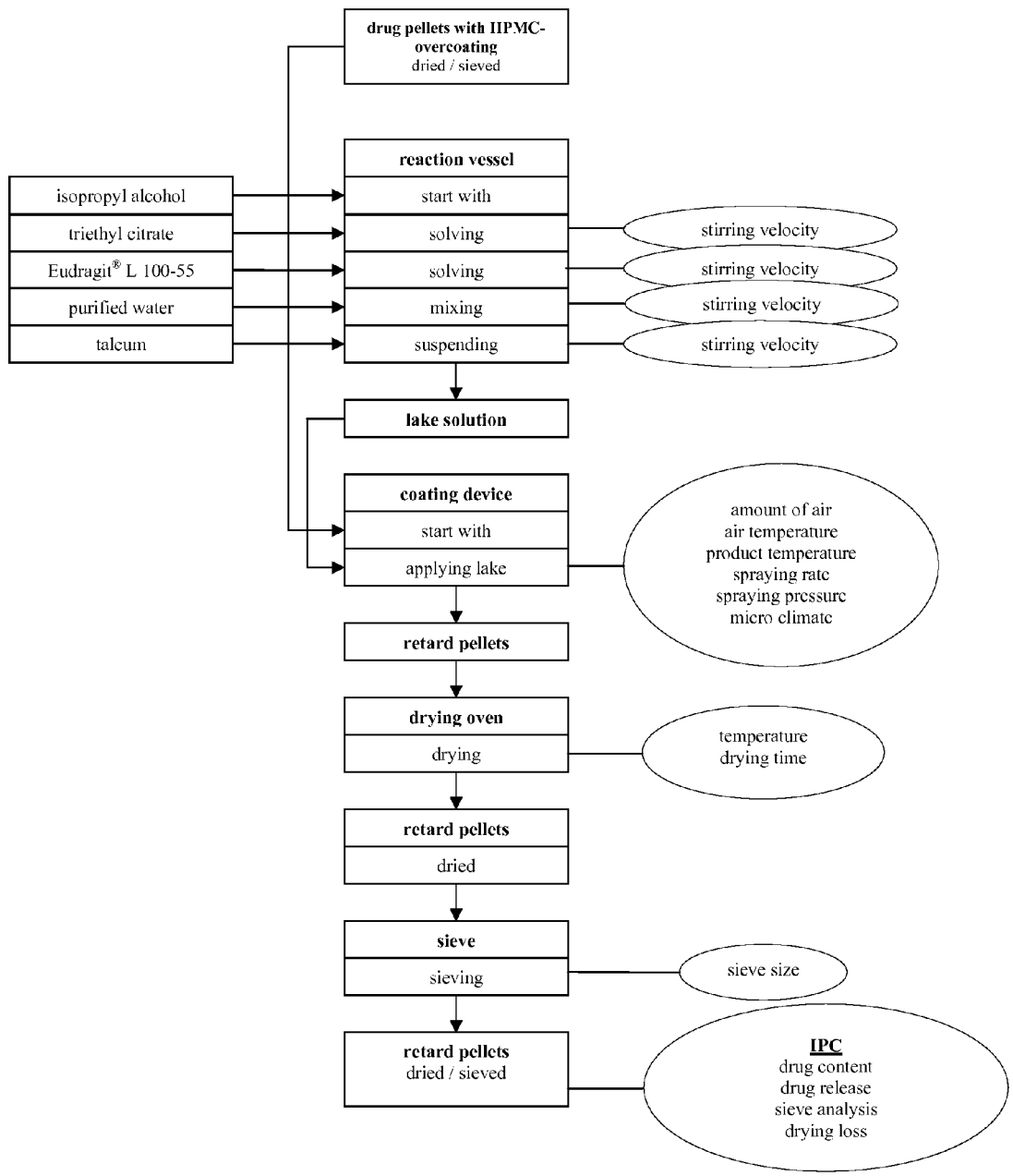

As illustrated in FIG. 13 isopropyl alcohol (341.36 g) was charged in a suitable reaction vessel and then triethyl citrate (1.25 g), Eudragit® L 100-55 (25.00 g) and purified water (46.55 g) were added in portions and dispersed in this solution with stirring. The solution was stirred at room temperature overnight. It was obtained a lake solution.

2. Spraying of the Obtained Lake Solution

Then talc (2.50 g) was suspended into the lake solution which was subsequently sprayed onto 1000.0 g of the product obtained in step d). To this purpose the pellets were placed in a suitable coating apparatus fitted with an air inlet and exhaust. At an air inlet temperature of about 35° C. the product was sprayed with the lake solution in continuous operation and sprinkled so as to produce roughly spherical particles. The following conditions were used:

| | |
|---|---|
| inlet air quantity | 70 m³/h |
| spraying rate | 2-6 g/min |
| spray pressure | 0.6 bar, |
| micro climate | 0.2 bar |
| nozzle diameter | 1.2 mm |
| spray time | about 3 h |
| product temperature | 30-35° C. |

The virtually spherical product obtained was then dried in a suitable drying device at 25° C. for 12 hours. The product was fractionated using a suitable screening machine with perforated plates having nominal mesh sizes of 1.25 mm.

Step f)

Packing into Capsules

Figure 14:
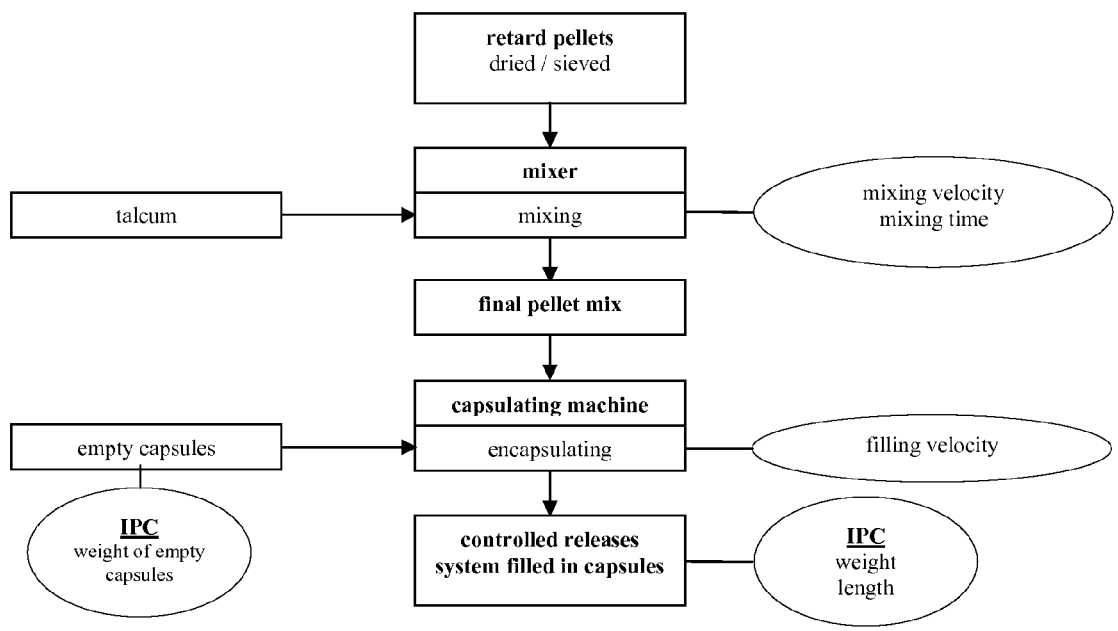

As illustrated in FIG. 14 a quantity of pellets containing active substance was mixed with talc to obtain the final mixture which was subsequently packed into size capsules such as hard gelatine capsules size 0 using a capsule filling machine.

During or after any step usual Internal Process Controls (IPC) were employed.

EXAMPLE 2.3

In the following a preferable process to manufacture the controlled release system of the present invention is exemplarily described. However, the process steps are not intended to be of limitative character at all.

The preparation of the controlled release system of the present invention in the following Example usually takes place over 6 steps:

step a): preparation of core material containing pH modifier;

step b): preparation of the first layer;

step c): preparation of the second layer containing active substance;

step d): preparation of the third layer;

step e): packing into capsules.

The steps will be described in the following in detail:

Step a)

Preparation of Core Material Containing pH Modifier a1) 1 part by weight of gum arabic is dissolved with stirring in 4 parts by weight of purified water at 50° C. 5 parts by weight of tartaric acid are then dissolved in this solution with stirring.

8.3 parts by weight of tartaric acid crystals with an average particle size of 0.4 to 0.6 mm are placed in a suitable coating apparatus fitted with an air inlet and exhaust and the container is set rotating. At an air inlet temperature of 60°-80° C. The tartaric acid crystals are sprayed with the solution of tartaric acid-gum arabic in intermittent operation and sprinkled with a total of 6.7 parts by weight of powdered tartaric acid, so as to produce roughly spherical particles.

The spherical tartaric acid core material is then dried in the rotating container at an air inlet temperature of 60°-80° C.

The core material is fractionated using a tumbler screening machine with perforated plates having nominal mesh sizes of 0.6 and 0.8 mm. The product fraction of between 0.6 and 0.8 mm is used in subsequent processing.

a2) Isolation of the Core Material Containing Tartaric Acid 1 part of hyprmellose is dispersed in 9 parts of water at 90° C. and further dissolved with stirring cooling the dispersion to 20° C. This insulating solution is sprayed onto the tartaric acid cores (a1) in a fluidised bed processing plant, 1 part by weight of tartaric acid-containing core material is sprayed with the hypromellose solution at an air entry temperature of 45°-49° C. by the Wurster spraying method. The isolated tartaric acid-containing core material is then dried in the circulating air dryer at 40° C. for 12 hours. To remove lumps the dried isolated tartaric acid-containing core material is screened through a screen with a nominal mesh size of 1.0 mm. The fraction of material (particle size less than 1 mm) is further processed.

The other steps b) to e) are illustrated in flow diagrams shown in FIGS. 15 to 19.

Step b)
Preparation of the First Layer

Figure 15:
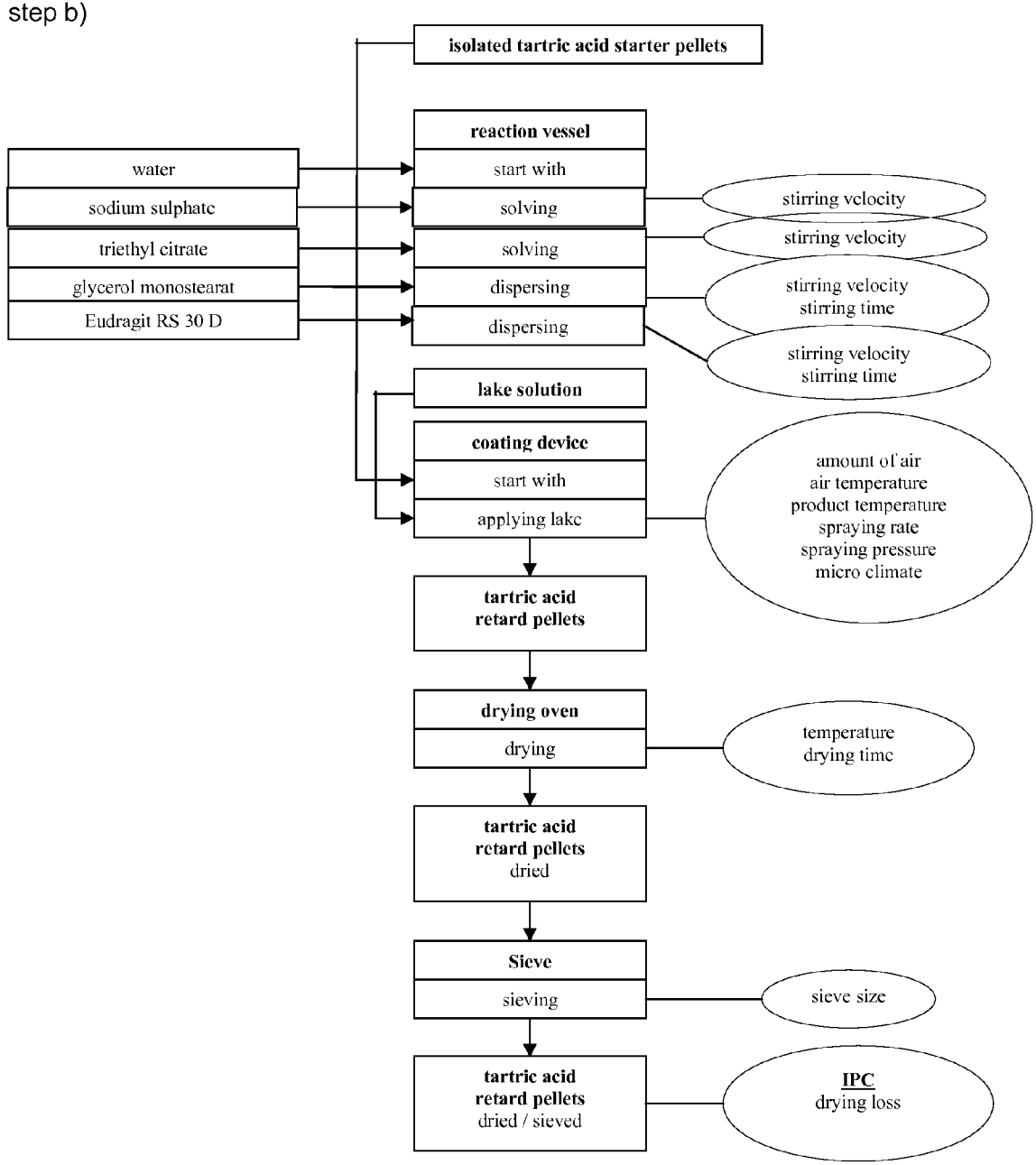
Figure 16:
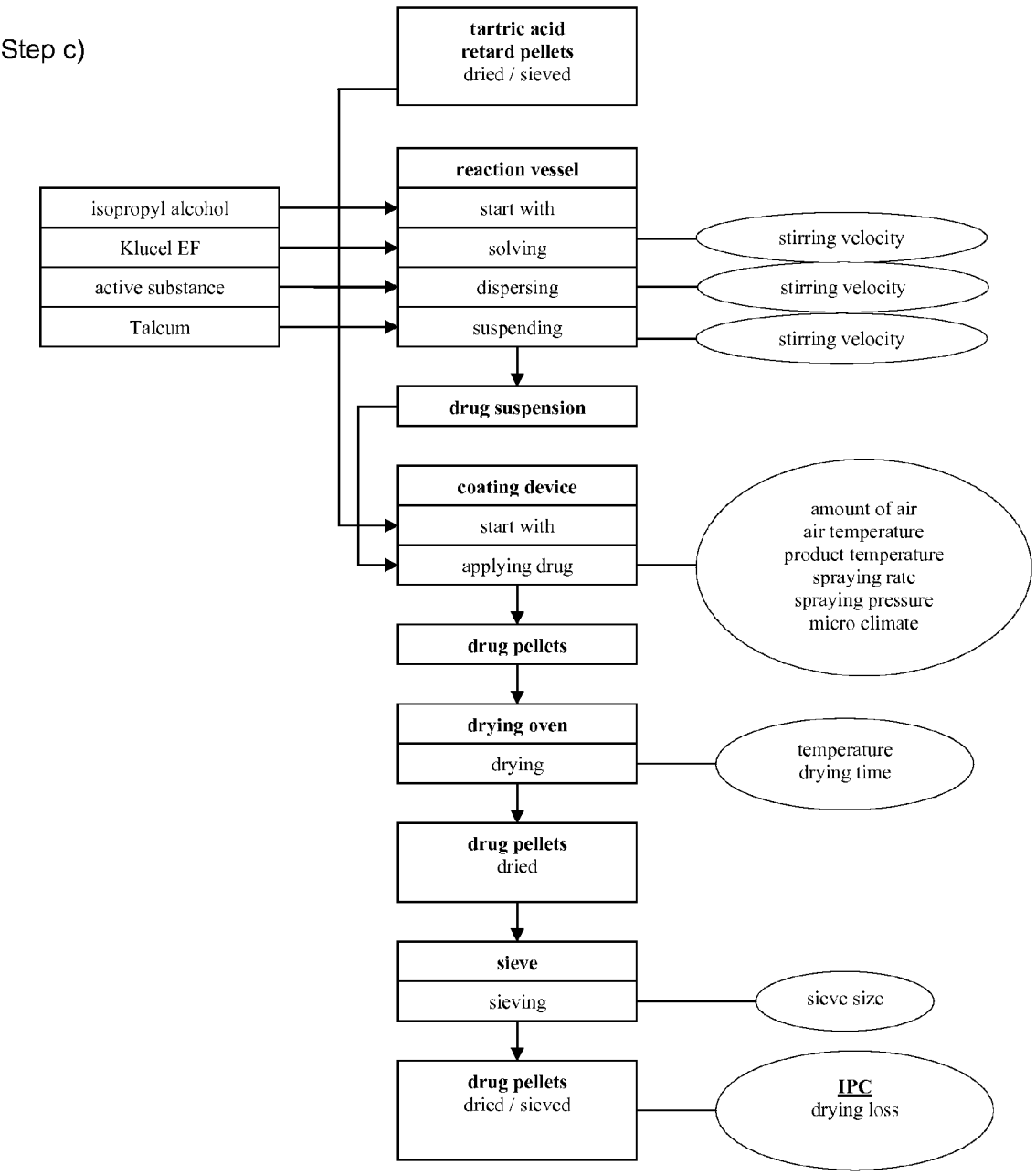

As illustrated in FIG. 15 it may be started with a core material prepared as described above, for example a core material containing tartaric acid, the first layer was subsequently prepared as follows:

1. Preparation of the Lake Solution

Purified water (1385.71 g) was charged in a suitable reaction vessel and then triethyl citrate (10.00 g), glycerol monostearate (10.00 g), sodium sulphate (8.83) and Eudragit RS 30 D (666.67 g) were added in portions and dispersed in this solution with stirring. The solution was stirred at room temperature overnight. It was obtained a lake solution.

2. Spraying of the Obtained Lake Solution

Then the obtained lake solution was sprayed onto 1000 g of tartaric starter pellets (insulated). To this purpose the pellets were placed in a suitable coating apparatus fitted with an air inlet and exhaust. At an air inlet temperature of about 40-48° C. the tartaric pellets were sprayed with the lake solution in continuous operation so as to produce roughly spherical particles. The following conditions were used:

| inlet air quantity | 90 m³/h |
| spraying rate | 2-10 g/min |
| spray pressure | 1.2 bar, |
| nozzle diameter | 1.0 mm |
| spray time | about 7 h |
| product temperature | 30-35° C. |

The virtually spherical product obtained was then dried in a suitable drying device at 40° C. for 24 hours. The product was fractionated using a suitable screening machine with perforated plates having nominal mesh sizes of 1.0 mm.

Step c)
Preparation of the Second Layer Containing the Active Substance

1. Preparation of the Lake Solution

As illustrated in FIG. 12 isopropyl alcohol (1360.00 g) was charged in a suitable reaction vessel and then Klucel EF (binder; 50.00 g), and flibanserin (250.00 g) added in portions and talc (40.00 g) were dispersed in this solution with stirring. The solution was stirred at room temperature overnight. It was obtained a lake solution.

2. Spraying of the Obtained Lake Solution

Then the lake solution was sprayed onto 778 g of the product obtained in step b). To this purpose the product was placed in a suitable coating apparatus fitted with an air inlet and exhaust. At an air inlet temperature of about 25° C. the product was sprayed with the lake solution in continuous operation and sprinkled so as to produce roughly spherical particles. The following conditions were used:

| inlet air quantity | 100 m³/h |
| spraying rate | 1-10 g/min |
| spray pressure | 0.6 bar, |
| micro climate | 0.2 bar |
| nozzle diameter | 1.2 mm |
| spray time | about 5 h |
| product temperature | 20-25° C. |

The virtually spherical product obtained was then dried in a suitable drying device at 40° C. for 12 hours. The product was fractionated using a suitable screening machine with perforated plates having nominal mesh sizes of 1.25 mm.

Step d)
Preparation of the Third Layer

1. Preparation of the Lake Solution

Figure 17:
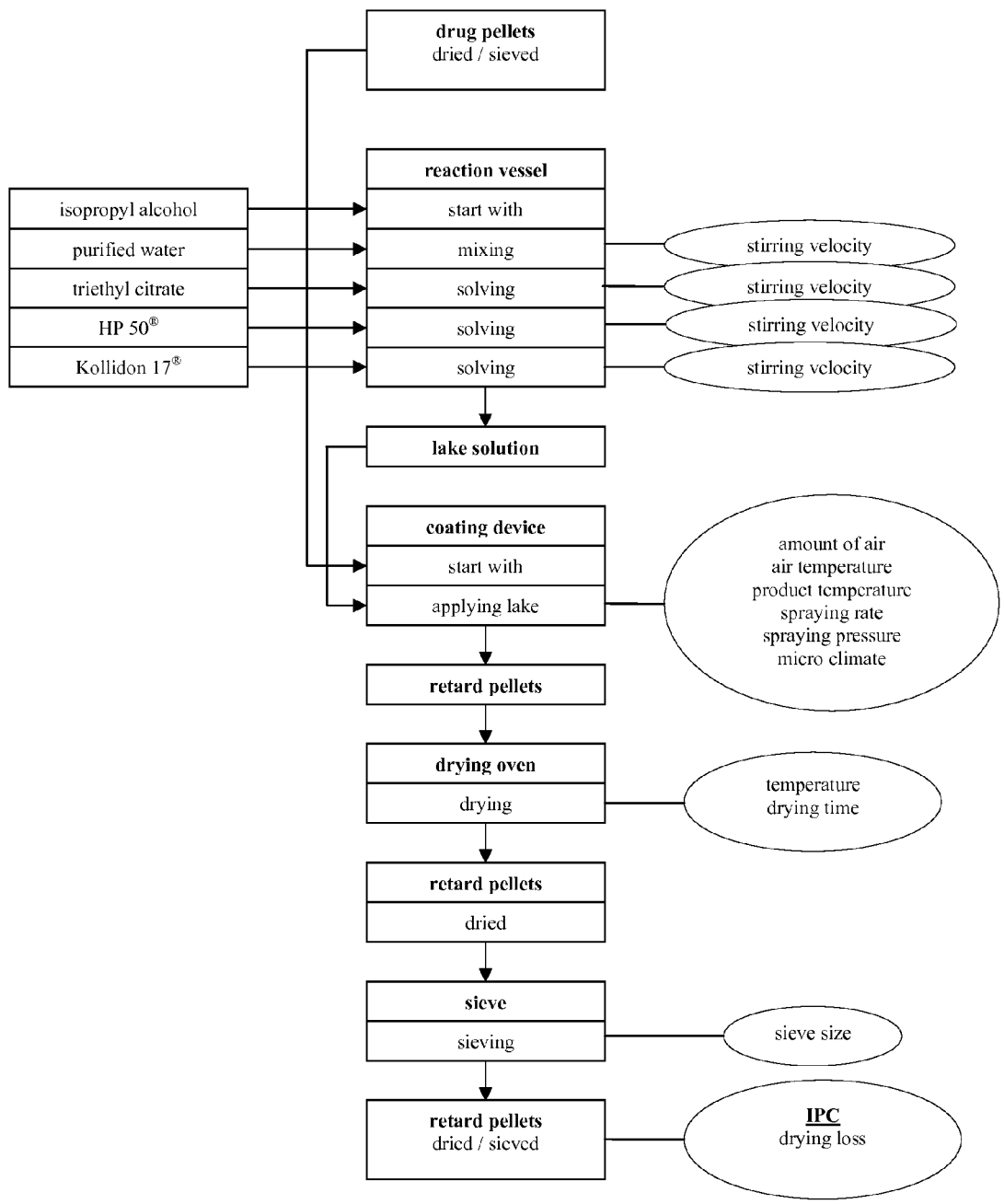
Figure 18:
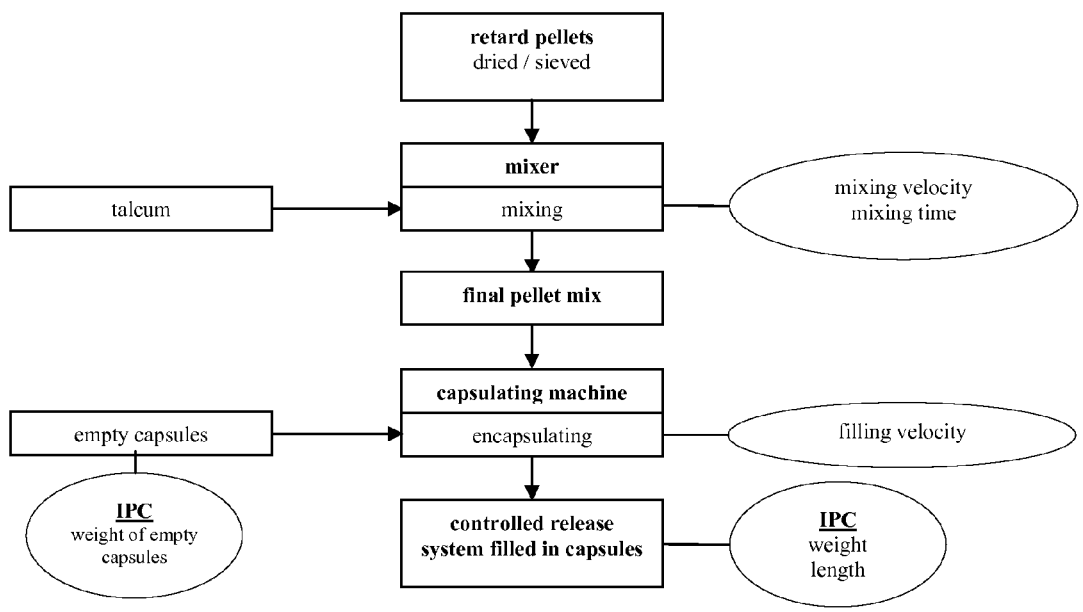

As illustrated in FIG. 17 isopropyl alcohol (33.09 g) was charged in a suitable reaction vessel and then purified water (7.79 g), triethyl citrate (0.12 g), glycerol monostearate (0.12 g), HP 50® (1.80 g) and Kollidon 17® (0.60 g) were added in portions and dispersed in this solution with stirring. The solution was stirred at room temperature overnight. It was obtained a lake solution.

2. Spraying of the Obtained Lake Solution

Then the lake solution was sprayed onto 30 g of the product obtained in step c). To this purpose the pellets were placed in a suitable coating apparatus fitted with an air inlet and exhaust. At an air inlet temperature of about 35° C. the product was sprayed with the lake solution in continuous operation and sprinkled so as to produce roughly spherical particles. The following conditions were used:

| inlet air quantity | 500 mbar |
| spraying rate | 0.3-0.5 g/min |
| spray pressure | 0.8 bar, |
| nozzle diameter | 0.3 mm |
| spray time | about 2 h |
| product temperature | 22-28° C. |

The virtually spherical product obtained was then dried in a suitable drying device at 40° C. for 12 hours. The product was fractionated using a suitable screening machine with perforated plates having nominal mesh sizes of 1.25 mm.

Step e)
Packing into Capsules

As illustrated in FIG. 11 a quantity of pellets containing active substance was mixed with talc to obtain the final mixture which was subsequently packed into size capsules such as hard gelatine capsules size 0 using a capsule filling machine.

During or after any step usual Internal Process Controls (IPC) were employed.

EXAMPLE 3

Dissolution profiles of modified release formulations of each of examples 1a, 1k, 2.1, 2.2, 2.3 were evaluated and compared to an immediate release formulation as described e.g. in WO 03/097058 (Example 3).

Dissolution testing was performed in apparatus 2 (USP 30) equipped with a pH-sensor and a titration apparatus. The drug product is placed in a biphasic dissolution medium with a lower phosphate buffered aqueous phase of 550 ml which is covered by an upper lipophilic phase of 100 ml n-octanol facilitating sink conditions in the lipophilic phase throughout the dissolution test. Drug release in the test apparatus is performed at 37° C. and 50 rpm for 24 hours in an apparatus 2 dissolution vessel. Quantification of drug release is performed online using a UV-DAD spectrophotometer for each phase. During the dissolution test pH-values are adjusted in 3 stages using a suitable titration system: stage 1 pH 2 (1 h), stage 2 pH 5.5 (2+2 h), stage 3 pH 6.8 (19 h). pH adjustment is performed using 5 M sodium hydroxide solution. In order to test the drug products ability to release the active ingredients at pH 5.5 in combination with the incorporated pH modifier, a decreased pH value in stage 2 (pH<5.5) is readjusted to the initial value after 2 hours. All dissolution profiles display the total drug dissolved in aqueous and organic phase together.

Figure 19:
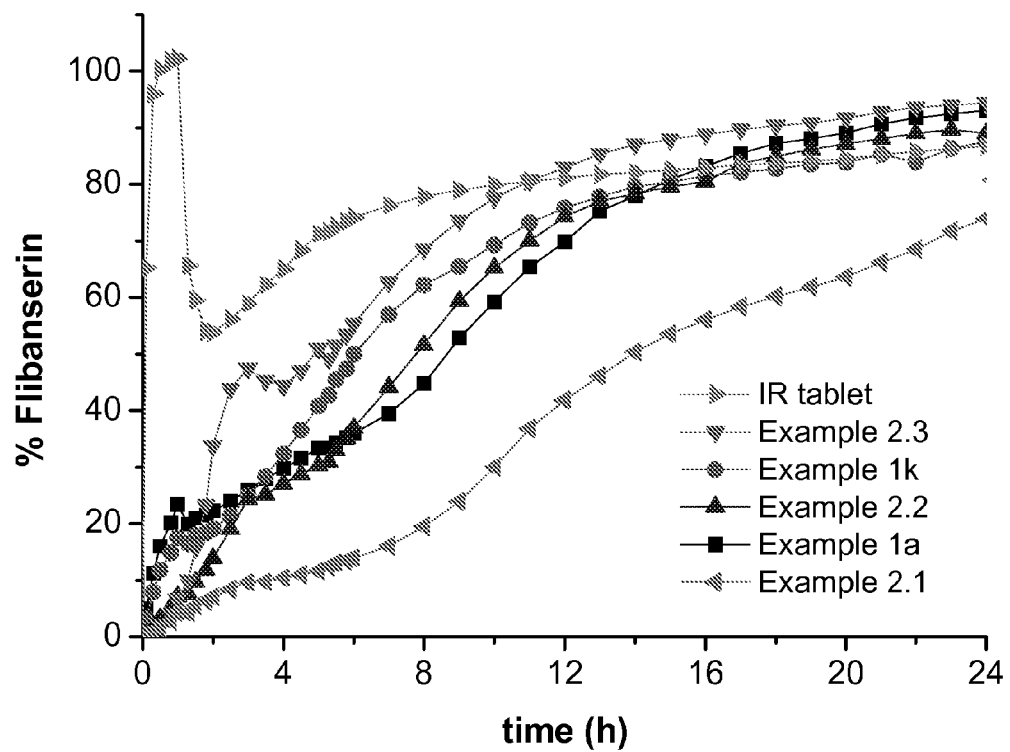
FIG. 19 shows the results of an in-vitro dissolution profiles of three different modified release formulations according to the invention compared to one non-modified release formulation as more fully described in Example 2.4.

Data are shown in FIG. 19. During the first hour in pH 2 at which the active ingredient displays good solubility, all examples proofed to prevent dose dumping. In contrast the IR tablet released the entire dose within 20 min at the first stage of pH 2 for 1 hour. At the beginning of the second stage (pH 5.5) the absorption of active ingredient dissolved in the aqueous phase at pH 2 (stage 1) into the octanol phase is not completed hence, the dissolved fraction of active ingredient in the aqueous phase is susceptible to precipitate at the pH change from 2 to 5.5. This phenomenon is highly pronounced for the IR tablet in the combined dissolution/absorption test however, is not of in vivo relevance for the IR tablet, for the AUC of the IR tablet is determined by the early drug release at low pH in the stomach. In contrast the advantageous modified release formulations showed various drug release rates controlled by the prototypes especially at pH values (5.5-6.8) where the aqueous solubility of the active ingredient is poor.

EXAMPLE 4

An in vivo study was conducted in healthy human volunteers to assess bioavailability of flibanserin formulated as the controlled or extended release systems of examples 1b, 2.1 and 2.2 in the fasted state and examples 1b and 2.1 after an high fat/high caloric meal by comparison with a reference treatment with immediate-release flibanserin tablets (flibanserin IR tablet 100 mg) as disclosed in WO 03/097058 (Example 3).

The study followed an open-label, 6-way, randomized crossover design and was conducted in healthy male and female subjects ranging from 21 to 50 years of age.

The subjects received each of the six treatments during the course of the study, which was conducted at a single center. A total of 24 subjects were enrolled. The subjects were either fasted overnight and then given a 100 mg oral dose of flibanserin or they received a single oral dose of 100 mg flibanserin directly after intake of a high fat/high caloric standard breakfast. Serial blood samples were taken over a 72 hour period for description of the controlled release profiles. Adverse events were recorded during the same 72 hour period.

Plasma flibanserin concentrations were quantitated by an HPLC-MS/MS method, validated over the assay range 1 to 1000 ng/ml. All runs met bioanalytical acceptance criteria for calibration standards and quality control.

Pharmacokinetic parameters for flibanserin were estimated by non-compartmental methods, using the nonlinear regression program WinNonlin™ (Professional, version 5.0.1, Pharsight Corporation, Mountain View, Calif.). Individual plasma concentration data and the actual time-points of blood sampling from each subject were used in the analysis. Plasma concentrations below the lower limit of quantitation at early time-points were set to zero, whereas those in the terminal phase were excluded from the analysis.

Results:

After single administration of 100 mg flibanserin with the example 1b to healthy male and female volunteers in the fasted state (N=24) and directly after a meal (N=24), maximum flibanserin plasma concentrations of 70 ng/mL and 189 ng/mL were reached. Corresponding systemic exposure after fasted and fed administration was 1540 ng·h/mL and 2380 ng·h/mL, respectively. Reported sedative adverse events were significantly reduced compared to the fasted administration of 100 mg flibanserin with an immediate release tablet were maximum plasma concentrations of 425 ng/mL and a total systemic exposure of 2130 ng·h/mL. Similar results were obtained after single administration of 100 mg flibanserin with the example 2.2 to healthy male and female volunteers in the fasted state (N=23), where maximum flibanserin plasma concentrations of 121 ng/mL were reached. Corresponding systemic exposure was 1670 ng·h/mL. Again, reported sedative adverse events were significantly reduced compared to the fasted administration of 100 mg flibanserin. Also after single administration of 100 mg flibanserin with the example 2.1 to healthy male and female volunteers in the fasted state (N=24) and directly after a meal (N=24), maximum flibanserin plasma concentrations of 53 ng/mL were reached. Corresponding systemic exposure after fasted and fed administration was 546 ng·h/mL and 629 ng·h/mL, respectively, which led to a significant reduction of reported sedative adverse events were if compared to the fasted administration of 100 mg flibanserin with an immediate release tablet.

What is claimed is:

1. A pharmaceutical release system comprising:
    (a) a therapeutically effective amount of flibanserin, or pharmaceutically acceptable salt thereof,
    (b) a pharmaceutically acceptable pH-dependent polymer;
    (c) a pharmaceutically acceptable pH-independent polymer; and
    (d) a pharmaceutically acceptable acid,
    wherein the composition exhibits a pharmacokinetic profile that is characterized by an average maximum flibanserin plasma concentration $C_{max}$ of less than 300 ng/mL and an average total systemic exposure between 1300 and 3000 ng·h/mL after administration of a single daily dose to healthy volunteers in fasted state or directly after a meal.

2. The pharmaceutical release system according to claim 1, characterized by an average maximum flibanserin plasma concentration $C_{max}$ of less than 300 ng/mL and an average total systemic exposure between 1500 and 2500 ng·h/mL after administration of a single daily dose to healthy volunteers in fasted state or directly after a meal.

3. The pharmaceutical release system according to claim 1, characterized by having an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured using a USP (Type II) apparatus.

4. The pharmaceutical release system according to claim 2, characterized by having an in vitro dissolution profile such that at least 1% w/w and no more than 60% w/w of the flibanserin is released at 1 hour; at least 5% w/w and up to 70% w/w of the flibanserin is released at 4 hours; at least 30% w/w and up to 100% w/w of the flibanserin is released at 12 hours, when dissolution is measured using a USP (Type II) apparatus.

5. The pharmaceutical release system according to claim 1, characterized by having an in vitro dissolution profile such that at least 1% w/w and no more than 50% w/w of the flibanserin is released at 1 hour; at least 5% w/w and up to 60% w/w of the flibanserin is released at 4 hours; at least 35% w/w and up to 95% w/w of the flibanserin is released at 12 hours, when dissolution is measured using a USP (Type II) apparatus.

6. The pharmaceutical release system according to claim 2, characterized by having an in vitro dissolution profile such that at least 1% w/w and no more than 50% w/w of the flibanserin is released at 1 hour; at least 5% w/w and up to 60% w/w of the flibanserin is released at 4 hours; at least 35% w/w and up to 95% w/w of the flibanserin is released at 12 hours, when dissolution is measured using a USP (Type II) apparatus.

* * * * *